(12) United States Patent
Yi et al.

(10) Patent No.: US 10,420,747 B2
(45) Date of Patent: Sep. 24, 2019

(54) CANCER TREATMENT METHOD USING AILANTHONE COMPOUNDS

(71) Applicant: East China Normal University, Shanghai (CN)

(72) Inventors: Zhengfang Yi, Shanghai (CN); Shihong Peng, Shanghai (CN); Yundong He, Shanghai (CN); Wenbo Zhou, Shanghai (CN); Yihua Chen, Shanghai (CN); Mingyao Liu, Shanghai (CN)

(73) Assignee: EAST CHINA NORMAL UNIVERSITY, Shanghai (CN)

( * ) Notice: Subject to any disclaimer, the term of this patent is extended or adjusted under 35 U.S.C. 154(b) by 49 days.

(21) Appl. No.: 15/346,743

(22) Filed: Nov. 9, 2016

(65) Prior Publication Data
US 2018/0125814 A1    May 10, 2018

(51) Int. Cl.
*A61K 31/352* (2006.01)

(52) U.S. Cl.
CPC .................................. *A61K 31/352* (2013.01)

(58) Field of Classification Search
CPC .................................................... A61K 31/352
See application file for complete search history.

(56) References Cited

FOREIGN PATENT DOCUMENTS

WO    WO 02062334 A2 * 8/2002 ........... A61K 31/366

OTHER PUBLICATIONS

Han, H. "Targeted Prodrug Design to Optimize Drug Delivery." AAPS Pharmsci. (2000), vol. 2 (1) article 6, pp. 1-11.*
Ettmayer, P., et al. "Lessons Learned from Marketed and Investigational Prodrugs." J. Med. Chem. (2004) 47(10), pp. 2393-2404.*
Testa, B. "Prodrug research: futile or fertile?" Biochem. Pharm. (2004) 68, pp. 2097-2106.*
Zhuo, Z., et al. "Ailanthone Inhibits Huh7 Cancer Cell Growth via Cell Cycle Arrest and Apoptosis In Vitro and In Vivo." Nature.com Scientific Reports. © Nov. 3, 2015, pp. 1-15.*
Murakami, C., et al. "Multidrug-resistant cancer cell susceptibility to cytotoxic quassinoids, and cancer chemopreventive effects of quassinoids and canthin alkaloids." Bioorganic & Medicinal Chemistry. (2004), vol. 12, pp. 4963-4968.*
American Pharmaceutical Review. "Pharmaceutical Excipients." © Mar. 19, 2015. Available from: < https://web.archive.org/web/20150319203101/https://www.americanpharmaceuticalreview.com/25335-Pharmaceutical-Raw-Materials-and-APIs/25283-Pharmaceutical-Excipients/ >.*
Thermo Fisher. "kb Cells." © 2018. Available from: < https://www.thermofisher.com/us/en/home/technical-resources/cell-lines/k/cell-lines-detail-494.html >.*
Quiaainoids: From Traditional Drugs to New Cancer Therapeutics. Curr. Med. Chem. (2011), vol. 18, No. 1, pp. 1-13.*
Quassinoids: From Traditional Drugs to New Cancer Therapeutics. Curr. Med. Chem. (2011), vol. 18, No. 1, pp. 1-13. (Year: 2011).*
American Pharmaceutical Review. "Pharmaceutical Excipients." © Mar. 19, 2015. Available from: < https://web.archive.org/web/20150319203101/https://www.americanpharmaceuticalreview.com/25335-Pharmaceutical-Raw-Materials-and-APIs/25283-Pharmaceutical-Excipients/ >. (Year: 2015).*
Tan, M., et al. "Androgen receptor: structure, role in prostate cancer and drug discovery." Acta Pharmacologica Sinica. (2015), vol. 36, pp. 3-23. (Year: 2015).*
Watson, R.W. and Fitzpatrick, J.M. "Targeting apoptosis in prostate cancer: focus on caspases and inhibitors of apoptosis proteins." BJU International. (2005), vol. 96, Supplement 2, pp. 30-34. (Year: 2005).*
He, Y., et al. "Ailanthone targets p23 to overcome MDV3100 resistance in castration-resistant prostate cancer." Nature Communications. (Dec. 13, 2016), pp. 1-14. (Year: 2016).*

* cited by examiner

*Primary Examiner* — Noble E Jarrell
*Assistant Examiner* — John S Kenyon
(74) *Attorney, Agent, or Firm* — Birch, Stewart, Kolasch & Birch, LLP

(57) ABSTRACT

A pharmaceutical composition comprising an ailanthone (AIL) compound or a derivative thereof, for the treatment of diseases or conditions caused by, dependent from, or associated with excessive androgen receptor activity. Ailantone compounds have been discovered to be a potent inhibitor of both full-length AR (AR-FL) and constitutively-active truncated AR splice variants (AR-Vs), and are found to possess favorable drug-like properties such as good bioavailability, high solubility, lack of CYP inhibition, and low hepatotoxicity. Methods of treatment are also provided.

10 Claims, 51 Drawing Sheets

Specification includes a Sequence Listing.

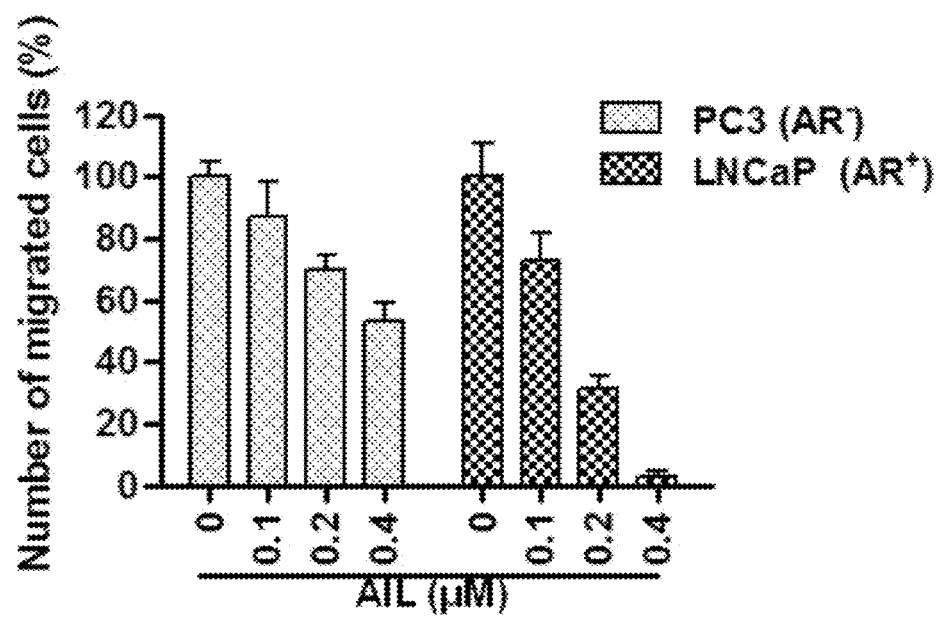
Fig. 7C (con't)

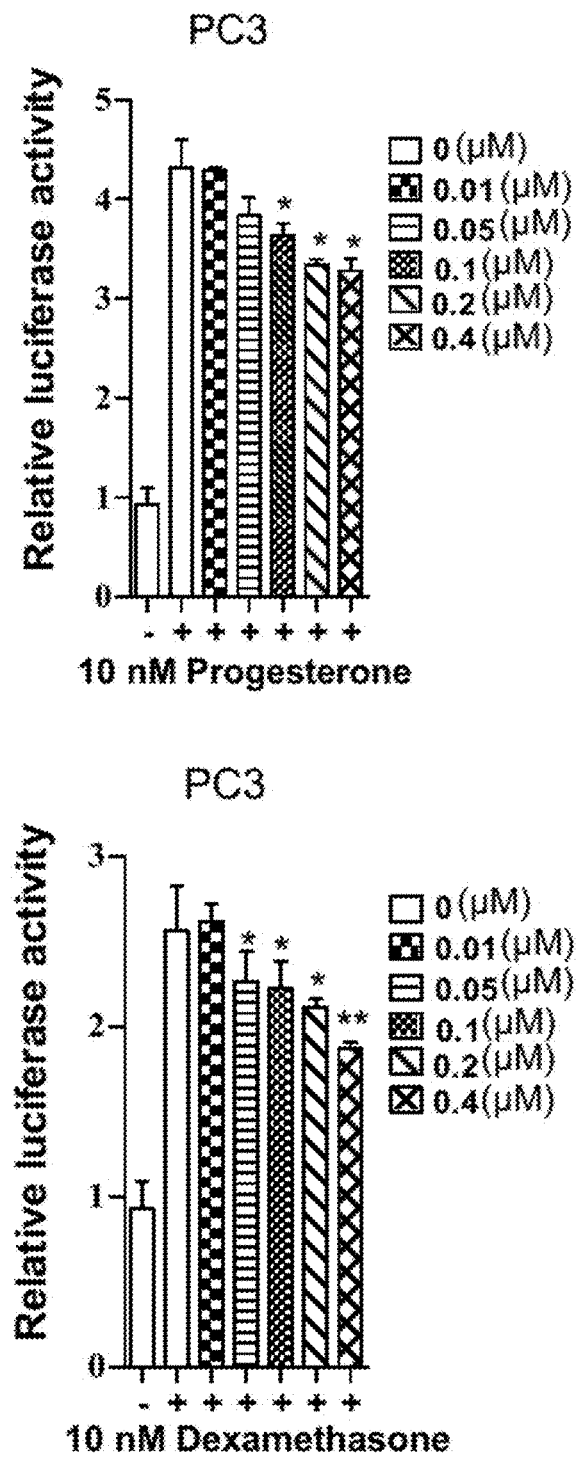
Fig. 13G (con't)

Fig. 16B (con't)

CANCER TREATMENT METHOD USING AILANTHONE COMPOUNDS

The present invention relates to the technical field of medicine, in particular to the application of medicine monomer ailanthone in treating prostate cancer.

BACKGROUND OF THE INVENTION

Prostate cancer (PCa) is the most common male cancer in many industrialized countries[1,2]. PCa initially depends on androgen receptor (AR) signaling for growth and survival. Androgen ablation therapy causes a temporary reduction in PCa tumor burden, but the tumor eventually develops into castration resistant prostate cancer (CRPC) with the ability to grow again in the absence of androgens[3]. Mechanisms of CRPC progression include AR amplification and overexpression[4,5], AR gene rearrangement promoting synthesis of constitutively-active truncated AR splice variants (AR-Vs)[6], and induction of intracrine androgen metabolic enzymes[3, 7].

The canonical human AR has 919 amino acids with a mass of 110 kDa, composed of four structurally and functionally distinct domains including the N-terminal domain (NTD, amino acids 1-537), DNA-binding domain (DBD, amino acids 537-625), hinge region (amino acids 625-669) and ligand binding domain (LBD, amino acids 669-919)[8]. When activated by endogenous androgens, AR translocates into the nucleus, associates with co-regulatory factors, and binds to specific genomic DNA sequences in the regulatory regions of AR target genes[9]. Previous clinical research showed that targeting AR was a valid therapeutic strategy for CRPC[10]. Indeed, recent clinical trials have shown that the AR antagonist MDV3100 (MDV)[11] and abiraterone, an inhibitor targeting androgen synthesis[12], are effective against CRPC. However, recent studies have reported that AR-Vs which lack the ligand binding domain (LBD) are resistant to anti-androgen therapy including MDV and abiraterone[13, 14, 15, 16, 17]. Since the major AR-Vs identified to date have an intact NTD and DBD, they display constitutive activity, which underlies the persistent AR signaling in CRPC expressing these variants[6, 18, 19, 20]. Collectively, both ligand-dependent full-length AR (AR-FL) and AR-Vs mediate distinct transcriptional programs in CRPC[21, 22, 23], but AR inhibitors currently in clinical use all target the LBD, and thus would not overcome cancer cell resistance driven by constitutively active AR-Vs.

AR is maintained in a ligand binding-competent state through its interaction with the foldosome, a protein complex consisting of the chaperones HSP40, HSP70 and HSP90 together with the co-chaperones HOP, p23 and the immunophilins FKBP51/52 and BAG-1[24]. Intriguingly, some inhibitors of HSP90 such as AT13387 decrease the expression of several HSP90 client proteins including wild-type AR and AR-V7 (an AR splice variant), and also disrupt nuclear localization of the AR. A phase I/II clinical trial of AT13387 alone or in combination with abiraterone acetate in patients with mCRPC is in progress[25]. Other HSP90 inhibitors that target the AR N-terminus including NVP-HSP990 and PF-04929113 have activity in preclinical studies[26, 27]. The co-chaperone p23 is over-expressed in multiple types of cancer, and protects cancer cells from HSP90 inhibitors[28]. p23 over-expression is induced upon treatment with either androgens or anti-androgens and facilitates PCa cell motility; p23 knockdown inhibits the invasiveness of the PCa cell line LNCaP, suggesting an important role of p23 in PCa metastasis independent of its role as an HSP90 co-chaperon[29]. The expression of p23 increases AR protein level, AR ligand binding activity, and AR's target promoter-binding activity; most importantly, p23 functions to promote AR activity in an HSP90-independent mechanism involving the direct binding to AR[30]. p23 is also associated with an increased resistance to etoposide and doxorubicin in breast cancer cells[31] along with elevated expression of a subset of estrogen-responsive genes[32]. p23 over-expression correlates with poor prognosis for breast cancer patients, implicating p23's role in breast cancer progression in addition to PCa, supporting the utility of p23 as a potential therapeutic target for cancer therapy.

Therefore there is a need for compounds that block the transcriptional activities of both ligand-dependent AR-FL and constitutively active AR-Vs.

SUMMARY OF THE INVENTION

The present invention discloses a pharmaceutical composition comprising an ailanthone (AIL) compound or a derivative thereof, for the treatment of diseases or conditions caused by, depending on, or associated with excessive androgen receptor activity. Ailantone compounds have been discovered to be a potent inhibitor of both full-length AR (AR-FL) and constitutively-active truncated AR splice variants (AR-Vs), and are found to possess favorable drug-like properties such as good bioavailability, high solubility, lack of CYP inhibition, and low hepatotoxicity.

Accordingly, in one embodiment, the present invention provides a method for treating cancer comprising administering to a subject in need thereof a compound of Formula I,

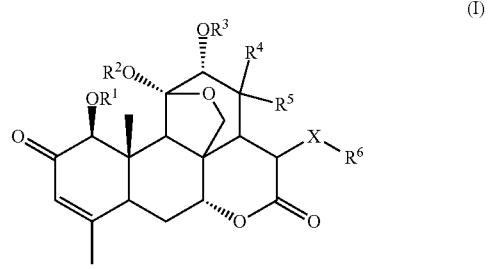

(I)

or a derivative, pharmaceutically acceptable salt, solvate, hydrate, polymorph, co-crystal, isotopically labeled derivative, or prodrugs thereof wherein, X is H; O; S or NH;

$R^1$, $R^2$ and $R^3$ is H; acyl; aliphatic; alkyl or alkenyl;

$R^4$ and $R^5$ is H; OH; $=CH_2$;

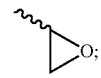

NH; acyl; aliphatic; alkyl or alkenyl; and when X is not H, $R^6$ is H; acyl; aliphatic; alkyl or alkenyl; wherein acyl refers to a group having a formula of —C(=O)$R^7$, —C(=O)O$R^7$, —C(=O)—O—C(=O)$R^7$, —C(=O)S$R^7$, —C(=O)N($R^7$)$_2$, —C(=S)$R^7$, —C(=S)N($R^7$)$_2$, —C(=S)S$R^7$, —C(=NR$^7$)$R^7$, —C(=NR$^7$)O$R^7$, —C(=NR$^7$)S$R^7$, or —C(=NR$^7$)N($R^7$)$_2$, wherein $R^7$ is hydrogen; halogen; substituted or unsubstituted hydroxyl; substituted or unsubstituted thiol; substituted or unsubstituted amino; substituted or unsubstituted acyl, cyclic or acyclic; substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; cyclic or acyclic, substituted or unsubstituted, branched or unbranched alkynyl; substituted or unsubstituted aryl; substituted or unsubstituted heteroaryl, aliphaticoxy, hetero-aliphaticoxy, alkyloxy, heteroalkyloxy, aryloxy, heteroaryloxy, aliphaticthioxy, heteroaliphaticthioxy, alkyloxy, heteroalkylthioxy, arylthioxy, or heteroarylthioxy.

In another embodiment, the present invention provides a method for treating cancer comprising administering to a subject in need thereof a compound of Formula (II):

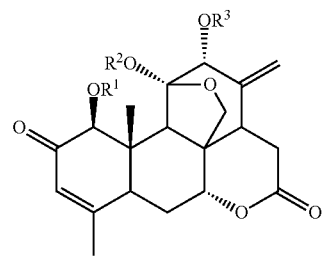

(II)

wherein $R^1$, $R^2$ and $R^3$ is H; acyl; aliphatic; alkyl or alkenyl.

In another embodiment, the present invention provides a method for treating cancer comprising administering to a subject in need thereof a compound of Formula (III);

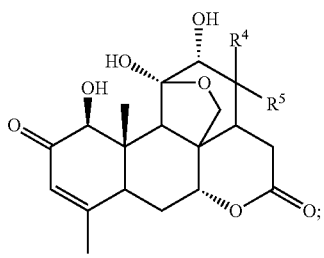

(III)

wherein $R^4$ and $R^5$ is H; OH; =CH$_2$;

NH; acyl; aliphatic; alkyl or alkenyl.

In another embodiment, the present invention provides a method for treating cancer comprising administering to a subject in need thereof a compound of Formula (IV);

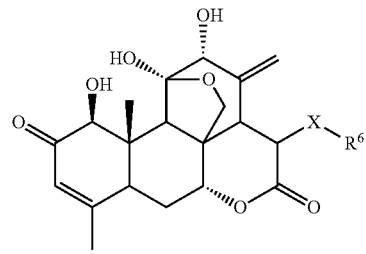

(IV)

wherein X is H; O; S or NH; and when X is not H, $R^6$ is H; acyl; aliphatic; alkyl or alkenyl.

In another embodiment, the present invention provides a method for treating cancer comprising administering to a subject in need thereof a compound of Formula (V):

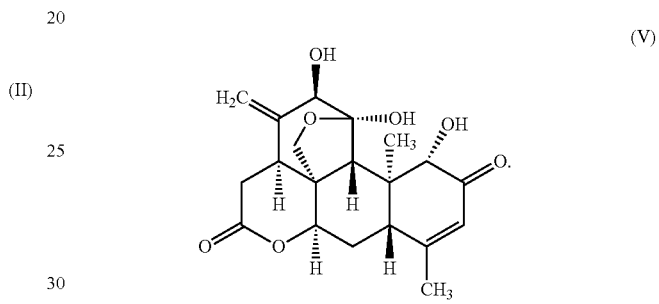

(V)

Cancers suitable for treatment with the method of the present invention include cancers associated with abnormal amplification or mutation of androgen receptor, such as but not limited to prostate cancer, breast cancer, lung cancer, colon cancer, brain cancer, skin cancer, bladder cancer, and renal cell carcinoma. Androgen-dependent prostate cancer, or a castration-resistant prostate cancer are specifically included, so are prostate cancers of the following type 22RV1, VCaP, LAPC4, C4-2B, LNCaP-MDV3100-R, PC3 and LNCaP.

The ailanthone compound or its derivatives inhibit the activity of androgen receptor, thereby inhibiting the proliferation, metastasis, growth, or cloning formation of prostate cancer cell, or promoting apoptosis of prostate cancer cell, or inducing the cycle arrest of prostate cancer cell.

In one embodiment, a therapeutically effective amount of the composition comprises 1.0 mg to 3.0 mg of the compound of Formula I per kg body weight daily of a subject in need thereof. In another embodiment, a therapeutically effective amount of the composition comprises 2.0 mg of the compound of Formula I per kg body weight daily of a subject in need thereof for a 21-day cycle.

The ailanthone compound induces androgen receptor ubiquitination by blocking the binding between an androgen receptor and a heat shock chaperones HSP90 complex, decreasing androgen receptor stability, resulting in degradation of the androgen receptor by proteasome and inhibition of the activity of androgen receptor. Specifica androgen receptor includes dihydrotestosterone DHT induced androgen receptor or androgen receptor AR1-651 lacking a ligand domain.

Also provided is a pharmaceutical composition, comprising a compound of Formula (I) according to Claim 1, or hydrate, or a pharmaceutically acceptable salt thereof, and a pharmaceutically excipient.

The present invention also provides a method for inhibiting androgen receptor activity, or inhibiting the proliferation, metastasis, growth, cloning formation of prostate cancer cells, or promoting apoptosis of prostate cancer cells, inducing the cycle arrest of prostate cancer cells in a subject in need thereof, cancer comprising administering to a subject in need thereof an ailanthone compound described above.

DETAILED DESCRIPTION OF THE INVENTION

Figure 1A:
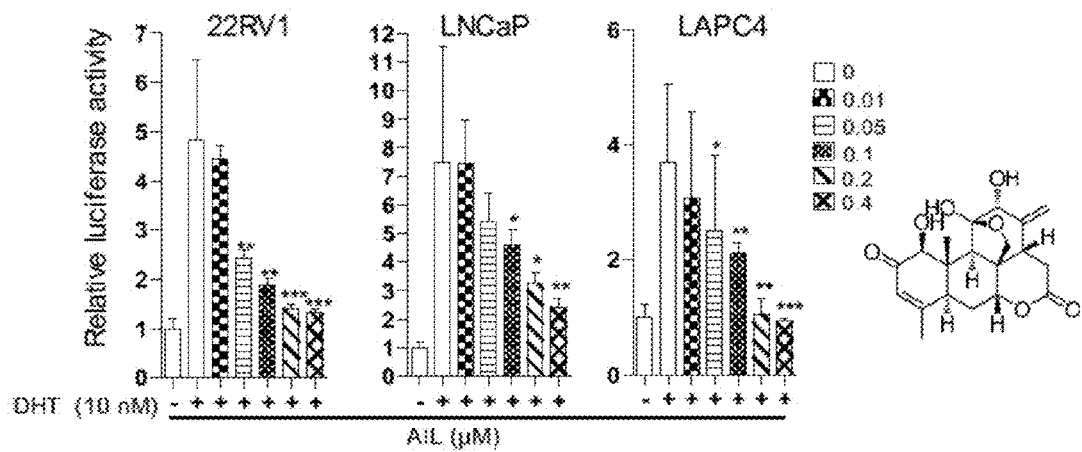
FIG. 1A-FIG. 1H. Inhibitory effects of AIL on AR activity and PCa cells proliferation. (A, B) PCa cells were treated with different concentrations of AIL for 12 hours and luciferase activities were measured. MMTV-luc reporter was stimulated by DHT (A) or exogenous $AR_{1-651}$ (B). (C) LNCaP cells were cultured in 5% c-FBS for 5 days and treated with 10 nM R1881 alone or 0.2 μM AIL with 10 nM R1881 for 12 hours. The genes expression was measured byquantitative-PCR. (D) PC3 cells were transfected with $AR_{1-651}$. MMTV-luc, Renilla-luc and treated with indicated concentrations of bicalutamide (BIC), MDV3100 (MDV) and AIL. After 12 hours, the MMTV-luc activities were detected (Left panel). 22RV1 cells were stimulated with or without 10 nM R1881 and treated with 10 μM MDV or 0.2 μM AIL. After 12 hours, total RNA was extracted and PSA MRNA was measured by quantitative-PCR (Right panel). (E,F) The AR negative cell lines PC3 and DU145 ($AR^-$), normal prostate cell lines RWPE-1 and WPMY-1 (N), and AR positive cell lines LNCaP, 22RV1, LAPC4 c4-2b, VcaP and LNCaP-MDV3100-R ($AR^+$) were treated with different concentrations of AIL for 48 hours. Cell proliferation was detected with the SRB assay (E). AR negative cell lines PC3 and DU145, and positive cell lines LNCaP, 22RV1 were treated with 0 or 0.1 μM AIL for 7 days, and the cell colonies were counted (F). Data was expressed as mean±s.d. of three independent assays; Two-way ANOVA followed by Bonferroni multiple comparison test; ***P<0.001. Scale bar, 200 μm. (G,H) Androgen-starved LNCaP, c4-2b and 22RV1 cells were treated with 10 μM BIC, 10 μM MDV and 0.1, 0.2, 0.4 μM AIL together with 0.1 nM R1881 stimulation for 96 hours (G). MDV3100-resistant LNCaP cells were treated with the indicated concentrations of BIC, MDV or AIL for 72 hours (H). Cell growth was determined by SRB assay. In panel A, B, C, D, G and H, data was expressed as mean±s.d. of three independent assays; Student's t-tests were performed; *P<0.05, P<0.01, *P<0.001.

The present inventors used the MMTV-luciferase (MMTV-luc) reporter system containing AR-binding elements[33] to screen compounds from various libraries of compounds (including compounds extracted from Traditional Chinese Medicine), and discovered that Ailanthone (AIL) and its derivatives[34, 35] potently reduce the transcriptional activities of both AR-FL and AR-Vs. In addition, we found that AIL and its derivatives decrease the levels of not only AR-FL proteins but also constitutively active AR-Vs, resulting in cell growth inhibition as well as suppression of MDV3100-resistant CRPC metastasis, by binding to p23 protein. The drug-like properties of AIL and its derivatives including solubility, pharmacokinetics, bioavailability, cytochrome P450 (CYP) inhibition and toxicity were evaluated. The findings herein showed that AIL is effective against CRPC and is suitable for further pharmaceutical applications Accordingly, the present invention provides a cancer treatment method using a compound of Formula (I),

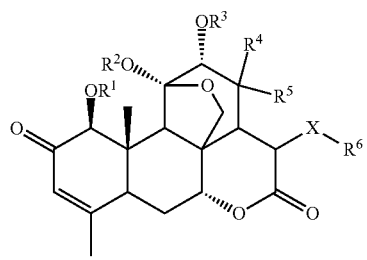
(I)

or a derivative, pharmaceutically acceptable salt, solvate, hydrate, polymorph, co-crystal, isotopically labeled derivative, and prodrugs thereof, wherein in Formula I, X is H; O; S or NH;

$R^1$, $R^2$ and $R^3$ is H; acyl; aliphatic; alkyl or alkenyl;

$R^4$ and $R^5$ is H; OH; =$CH_2$;

NH; acyl; aliphatic; alkyl or alkenyl; and when X is not H, $R^6$ is H; acyl; aliphatic; alkyl or alkenyl, the method comprising administering a pharmaceutical composition comprising a compound of Formula I and a pharmaceutically acceptable excipient, to a subject in need thereof.

In certain embodiments, the ailanthone compound of the invention and its derivatives may be described as Formula (II), which is Formula 1 where X is H; the $R^4$ and $R^5$ groups taken together may form =$CH_2$;

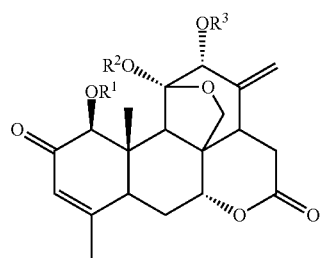
(II)

and pharmaceutically acceptable salts, solvates, hydrates, polymorphs, co-crystal, isotopically labeled derivatives, and prodrugs thereof.

wherein, $R^1$, $R^2$ and $R^3$ is H; acyl; aliphatic; alkyl or alkenyl.

In certain embodiments, the ailanthone and its derivatives are one of Formula (III);

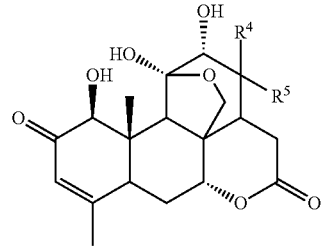
(III)

and pharmaceutically acceptable salts, solvates, hydrates, polymorphs, co-crystal, isotopically labeled derivatives, and prodrugs thereof.

wherein $R^4$ and $R^5$ is H; OH; =$CH_2$;

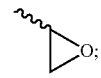

NH; acyl; aliphatic; alkyl or alkenyl.

In certain embodiments, the ailanthone and its derivatives are one of Formula (IV);

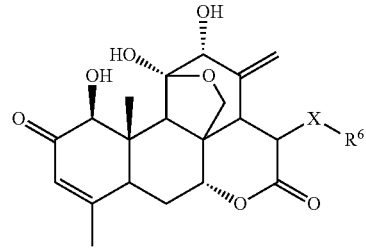
(IV)

and pharmaceutically acceptable salts, solvates, hydrates, polymorphs, co-crystal, isotopically labeled derivatives, and prodrugs thereof, wherein, X is H; O; S or NH; and when X is not H, $R^6$ is H; acyl; aliphatic; alkyl or alkenyl;

In certain embodiments, in Formula (I), the ailanthone and its derivatives are one of Formula (V)

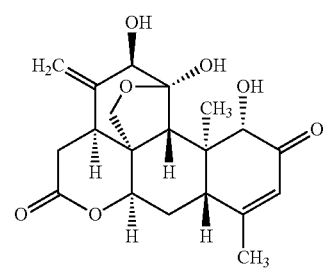
(V)

Formula (V) is also known as ailanthone, its chemical name is 11β,20-Epoxy-1β,11,12α-trihydroxypicrasa-3,13 (21)-diene-2,16-dione; molecular formula: $C_{20}H_4O_7$; molecular weight: 376.405, CAS number: 981-15-7.

The present invention provides a use of ailanthone and its derivatives in the preparation of medicine for treating prostate cancer, wherein said ailanthone and its derivatives are indicated as Formulae (I-V), said ailanthone inhibits the activity of androgen receptor, thereby inhibits the proliferation, metastasis, growth, cloning formation of prostate cancer cell, promotes apoptosis of prostate cancer cell, induces the cycle arrest of prostate cancer cell.

The present invention further provides a method of treating malignant tumor comprising administering a pharmaceutical composition comprising a therapeutically effective amount of a compound of Formula (I-V), or a hydrate, or a pharmaceutically acceptable salt thereof.

In the method of the present invention, said malignant tumors is selected from the group consisting of prostate cancer, breast cancer, lung cancer, colon cancer, brain cancer, skin cancer, bladder cancer, and renal cell carcinoma.

In the method of the present invention, said ailanthone and its derivatives inhibit the activity of androgen receptor, thereby inhibits the proliferation, metastasis, growth, cloning formation of prostate cancer cell, promotes apoptosis of prostate cancer cell, and induces the cell cycle arrest of prostate cancer cell.

In the method of the present invention, said prostate cancer is of abnormal amplification and/or mutation of androgen receptor.

In the method of the present invention, said prostate cancer is an androgen dependent prostate cancer.

In the method of the present invention, said prostate cancer is castration-resistant prostate cancer.

In the method of the present invention, said prostate cancer is of the type selected from the group consisting of 22RV1, VCaP, LAPC4, C4-2B, LNCaP-MDV3100-R, PC3 and LNCaP.

In the method of the present invention, the therapeutically effective amount of the composition comprises 1.0 mg to 3.0 mg ailanthone or its derivatives, or hydrate, or a pharmaceutically acceptable salt thereof per kg body weight daily of a subject in need thereof.

Preferably, in the method of the present invention, the therapeutically effective amount of the composition comprises 1.0 mg to 3.0 mg ailanthone or its derivatives, or hydrate, or a pharmaceutically acceptable salt thereof per kg body weight daily of a subject in need thereof for a 21-day cycle.

Preferably, the method of the present invention, the therapeutically effective amount of the composition comprises 2.0 mg ailanthone or its derivatives, or hydrate, or a pharmaceutically acceptable salt thereof per kg body weight daily of a subject in need thereof for a 21-day cycle.

In the method of the present invention, said ailanthone or its derivatives induce androgen receptor ubiquitination by blocking the binding between the androgen receptor and the heat shock chaperones HSP90 complex, then decreases the androgen receptor stability, resulting the degradation of the androgen receptor by proteasome, thereby inhibits the activity of androgen receptor.

In the method of the present invention, the androgen receptor is dihydrotestosterone DHT induced androgen receptor or androgen receptor AR1-651 lacking a ligand domain.

The present invention further provides a pharmaceutical composition, said pharmaceutical composition comprises a compound of Formula (I-V), or hydrate, or a pharmaceutically acceptable salt thereof and a pharmaceutically acceptable excipient.

In one embodiment, the therapeutically effective amount of the pharmaceutical composition comprises 1.0 mg to 3.0 mg ailanthone or its derivatives, or hydrate, or a pharmaceutically acceptable salt thereof per kg body weight daily of a subject in need thereof. In another embodiment, the therapeutically effective amount of the pharmaceutical composition comprises 1.0 mg to 3.0 mg ailanthone or its derivatives, or hydrate, or a pharmaceutically acceptable salt thereof per kg body weight daily of a subject in need thereof for a 21-day cycle.

In one embodiment, the therapeutically effective amount of the pharmaceutical composition comprises 2.0 mg ailanthone or its derivatives, or hydrate, or a pharmaceutically acceptable salt thereof per kg body weight daily of a subject in need thereof for a 21-day cycle.

The pharmaceutical composition of the present invention inhibits the activity of androgen receptor, thereby inhibiting the proliferation, metastasis, growth, cloning formation of prostate cancer cell, promoting apoptosis of prostate cancer cell, and induce the cycle arrest of prostate cancer cell, wherein said prostate cancer is of abnormal amplification and/or mutation of androgen receptor, or androgen receptor dependent prostate cancer, or castration-resistant prostate cancer. In one embodiment, the prostate cancer is selected from the group consisting of 22RV1, VCaP, LAPC4, C4-2B, LNCaP-MDV3100-R, PC3 and LNCaP.

Formula (I-V) ailanthone and its derivatives inhibit the proliferation, metastasis, growth and cloning formation of prostate cancer cells, promotes apoptosis of prostate cancer cell, induce cell cycle arrest of prostate cancer cell, and inhibit tumor growth and metastasis in CRPC animal models.

In the application of the present invention, Formula (I-V) ailanthone and its derivatives inhibit the transcriptional activity of androgen receptor. Formula (I) compounds inhibit the proliferation of androgen receptor mutated prostate cancer cells. It inhibits the proliferation of androgen receptor mutated 22RV1, VCaP, LAPC4, C4-2B, LNCaP-MDV3100-R and androgen dependent LNCaP prostate cancer cell in vitro and/or in vivo.

In the application of the present invention, Formula (I-V) ailanthone and its derivatives inhibit the androgen receptor activity and growth of prostate cancer cells; wherein, said prostate cancer cells are 22RV1, VCaP, LAPC4, C4-2B, LNCaP-MDV3100-R and LNCaP.

In the application of the present invention, Formula (I-V) ailanthone and its derivatives promote cell apoptosis of androgen receptor mutated VCaP, LAPC4, C4-2B, and LNCaP-MDV3100-R.

In the application of the present invention, Formula (I-V) ailanthone and its derivatives inhibit the androgen receptor protein expression significantly; Formula (I-V) ailanthone and its derivatives also inhibit the downstream gene expression of androgen receptor. Formula (I-V) ailanthone and its derivatives inhibit the proliferation and migration more obviously on androgen receptor positive prostate cancer cells; wherein, said androgen receptor positive prostate cancer cells are 22RV1, VCaP, LAPC4, c4-2b, LNCaP-MDV3100-R, and LNCaP.

In the application of the present invention, Formula (I-V) ailanthone and its derivatives inhibit tumor growth and metastasis in CRPC animal models; wherein, said CRPC prostate cancer are LNCaP, 22RV1 and VCaP.

In the application of the present invention, Formula (I-V) ailanthone and its derivatives significantly inhibit prostate cancer cells proliferation and metastasis in vitro at low concentration (<1 μM); in animal models such as mice, Formula (I-V) ailanthone and its derivatives inhibit the growth and metastasis of prostate cancer cells in vivo at the dose of 2.0 mg/kg/d effectively The present invention also provides for the use of Formulae I-V ailanthone and its derivatives in inhibiting proliferation of androgen receptor mutated prostate cancer cells. Formulae I-V ailanthone and its derivatives suppress androgen receptor mutated 22RV1 and VCaP prostate cancer which are resistant to Bicalutamide or MDV3100 treatment. Formula (I-V) ailanthone and its derivatives also can inhibit proliferation of androgen dependent LNCaP prostate cancer cell. Formula (I-V) ailanthone and its derivatives inhibit the growth of castration resistant prostate cancer cells in mice animal model; wherein, said castration resistant prostate cancer cells are 22RV1, VCaP, LAPC4, C4-2b and LNCaP-MDV3100-R.

The present invention provides a method of using Formula (I-V) ailanthone and its derivatives in inhibiting the migration or metastasis of prostate cancer cells in vitro/in vivo. Formula (I-V) ailanthone and its derivatives migration of LNCaP in vitro and 22RV1 in vivo. Formula (I-V) ailanthone and its derivatives inhibit the metastasis of castration resistant prostate cancer cells in mice animal model; wherein, said castration resistant prostate cancer cells are 22RV.

The present invention discloses the use of Formula (I-V) ailanthone and its derivatives in inhibiting the activity of androgen receptor and prostate cancer growth. Formula (I-V) ailanthone and its derivatives inhibit the dihydrotestosterone (DHT) induced androgen receptor activity and activity of androgen receptor splice variant lacking the LBD. Formula (I-V) ailanthone and its derivatives induce AR degradation by disrupting the interaction of AR with its chaperones HSP90 and HSP70, resulting in AR ubiquitination and degradation, and then inhibit the activity of androgen receptor and the growth of prostate cancer cells. Formula (I-V) ailanthone and its derivatives can also inhibit the growth of prostate cancer cells including 22RV1, VCaP, LAPC4, c4-2b, LNCaP-MDV3100-R, LNCaP.

In present invention, Formula (I-V) ailanthone and its derivatives significantly inhibit prostate cancer cells proliferation and metastasis in vitro at low concentration (<1 µM): in animal models in mice, Formula (I-V) ailanthone and its derivatives inhibit the growth and metastasis of prostate cancer cells in vivo at the dose of 2 mg/kg/d effectively The present invention provides a use and/or a method of Formula (I-V) ailanthone and its derivatives in inhibiting colony formation of prostate cancer cell. For colony formation assay, prostate cancer cells were incubated with indicated concentrations of AIL in complete RPMI 1640 for two weeks and then cells were fixed with 4% paraformaldehyde and stained with crystal violet. Colonies were visualized under a microscope, and all of the fields were imaged and counted. Colony formation as a % of vehicle control for each cell line is presented. Wherein, said prostate cancer cell is LNCaP or 22RV1.

The present invention provides a use and/or method of Formula (I-V) ailanthone and its derivatives promote apoptosis of prostate cancer cell. After treatment with different concentrations of AIL or its derivatives, cells were trypsinized, washed with PBS and stained with 20 µg/ml propidium iodide (PI) solution and Annexin V-FITC for 15 min at room temperature in the dark. The stained cells were analyzed using BD LSRII flow cytometry (BD Biosciences). Wherein said prostate cancer cell is LNCaP or 22RV1. Formula (I-V) ailanthone and its derivatives promote apoptosis of prostate cancer cell 22RV1 with androgen receptor mutation.

The present invention provides a use and/or a method of Formula (I-V) ailanthone and its derivatives in inhibiting the activity of androgen receptor. For dual luciferase screening assay, prostate cancer cells were transfected with MMTV-luc, *Renilla*-luc (phRL-TK, Promega), ARor AR1-651(vector: pFLAG-CMV-1) plasmids (provided by DrJie-Min Wong) 50 using lipofectamine 2000 (Invitrogen) according to the manufacturer's instructions. After transfection for 24 hours, the transfected cells were treated with DHT (Sigma, cat. no. A8380) or DHT with compounds for 12 hours. *Renilla* and firefly activities were then determined by luminometry using the Dual-Luciferase Reporter Assay System (Promega) and the ratio calculated. Results were expressed as the ratio of firefly to *Renilla* luciferase activity.

The present invention provides a use and/or a method of Formula (I-V) ailanthone and its derivatives in inhibiting the activity of androgen receptor protein expression. Cells were treated as described in the corresponding section of Results and then lysed by boiling for 10 min in sample buffer (2% SDS, 10% glycerol, 10% β-Mercaptoethanol, Bromphenol Blue and Tris-HCl, pH 6.8). Lysates were fractionated on polyacrylamide gels and transferred to nitrocellulose. The blots were probed with specific antibodies followed by secondary antibody then membranes were examined using the LI-COR Odyssey infrared imaging system (LI-COR Biotechnology, Lincoln Nebr.). The AR (N20, sc-816 and H280, sc-13062; 1:1000) antibodies were purchased from Santa Cruz Biotechnology (Santa Cruz, Calif.). The secondary antibody was conjugated with IRDye 680/800 (Millennium Science; 926-32221, 926-32210; 1:10000).

The present invention provides a use and/or a method of Formula (I-V) ailanthone and its derivatives in inhibiting the downstream gene expression mediated by androgen receptor. Cells were cultured with RPMI 1640 with 5% charcoal dextran treated FBS for 5 days prior to treatment with R1881 (Sigma, cat. no. R0908) alone or R1881 and AIL for 12 h. Total RNA was extracted using TRIzol (Takara, Japan) according to the manufacturer's instructions. 1 µg of total RNA was used for cDNA synthesis using a cDNA reverse transcription kit (Takara, Japan). Real-time PCR was performed in triplicate using gene-specific primers on a Stratagene Mx3005P PCR system (Agilent Technologies) machine. The mRNA expression levels were normalized to β-actin expression or GAPDH. All analysis was performed using Microsoft Excel 2010 and GraphPad Prism 5 software. The gene-specific primers are listed in Table 1.

The present invention provides a use and/or a method of Formula (I-V) ailanthone and its derivatives for blocking the androgen receptor signaling pathway.

The present invention provides a use and/or a method of Formula (I-V) ailanthone and its derivatives for treating early stage androgen dependent prostate cancer, late stage castration-resistant prostate cancer, and metastatic prostate cancer (Subcutaneous tumor-burdened experiments). BALB/c-nude mice (6-8 weeks old, male) were purchased from the Sino-British Sippr/BK Lab Animal Co., Ltd (Shanghai, China) and maintained under pathogen-free conditions. The animal use protocol was approved by the Institutional Animal Care and Use Committee of East China Normal University. The 22RV1, LNCaP and VCaP xenograft tumor models were developed by injecting 3×106 22RV1 cells or 5×106LNCaPorVCaP cells in suspension into the right flank of a BALB/c-nude mouse; cells were suspended in 100 µl PBS or 50% Matrigel (LNCaP and VCaP) respectively. Specifically for LNCaP and VCaP cells, continuous release testosterone pellets (15 mg testosterone per pellet, Sigma-Aldrich) were implanted subcutaneously to stimulate the growth of LNCaP and VCaP xenografts. Tumor nodules were allowed to grow to a volume about 100 mm3 before initiating treatment. Tumor-bearing BALB/c-nude mice were randomly assigned to three groups and treated with the indicated compound or drug. The tumor volume and mouse body weight were measured twice a week. The tumor volume was calculated using the following equation: tumor volume (V)=length×width×width×0.52.

In Situ Tumor-Burdened

For orthotopic castration resistant prostate cancer xenografts, male BALB/c-nude mice (8-9 weeks of age) were anesthetized using 150 mgkg$^{-1}$ 2,2,2-tribromethanol plus 350 mgkg$^{-1}$ tert-amyl alcohol and then 5×10$^5$ 22RV1-luc cells suspended in 30 µl 50% Matrigel were surgically injected into the dorsolateral prostate lobes. One week after injection, the tumor-bearing mice were castrated and randomly assigned to three groups. A week later, animals were intraperitoneally injected with AIL (2 mgkg$^{-1}$), MDV (10 mgkg$^{-1}$) or DMSO (as controls). Prostate tumor growth and local metastasis were monitored weekly using the IVIS Imaging System (Xenogen Corporation, Alameda, Calif.). Images and measurements of bioluminescent signals were acquired and analyzed using LivingImage and Xenogen software[52].

The treatment is referred to inhibiting proliferation, metastasis, growth and cloning formation of prostate cancer cells, promoting cell apoptosis of prostate cancer cell, inducing cell cycle arrest of prostate cancer cell, and inhibiting tumor growth and metastasis in CRPC animal models.

The present invention provides the application and method of inhibiting the androgen receptor by Formula (I-V) ailanthone and its derivatives. Formula (I-V) ailanthone and its derivatives induce androgen receptor ubiquitination by blocking the binding between the androgen receptor and the heat shock chaperones HSP90 complex, then decreases the androgen receptor stability, resulting the degradation of the androgen receptor by proteasome, and then down-regulate the transcriptional activity and inhibit its downstream gene expression.

The present invention provides Formula (I-V) ailanthone and its derivatives, through screening by luciferase assay, that can inhibit the proliferation, growth and migration of the prostate cancer cell in vitro and in vivo strongly, and also block the androgen receptor signal pathway effectively.

The present invention demonstrated the Formula (I-V) ailanthone and its derivatives and pharmaceutical composition containing said Formula (I-V) ailanthone and its derivatives could inhibit the proliferation, metastasis, growth, cloning formation of prostate cancer cell, promote apoptosis of prostate cancer cell, induce the cycle arrest of prostate cancer cell. And further demonstrates that prostate cancer cell expressing androgen receptor have high sensitivity to (I-V) ailanthone and its derivatives.

In the present invention, "castration-resistant prostate cancer (CRPC)" refers to a condition in which prostate cancer patients are relapsed after castration treatment (testicular or chemical castration), castration-refractory prostate cancer is called castration Resistant prostate cancer, it is the biggest killer of prostate cancer patients.

In the present invention, "androgen receptor (AR)" means that the androgen receptor (AR) belongs to a steroid receptor in the nuclear receptor superfamily. AR is generally composed of four domains: the N-terminal transcriptional activation domain (NTD), the DNA binding domain (DBD), the hinge domain and the ligand-binding domain (LBD). Androgen receptor closely related to the development and progression of prostate cancer. After androgen such as dihydrotestosterone (DHT) binding, androgen receptor enter to the nucleus and activate the downstream gene expression.

Currently, androgen receptor antagonists used in clinical such as bicalutamide and MDV3100 (Enzalutamide) are both through binding to the ligand binding domain (LBD) of the androgen receptor and inhibit its transcriptional activity.

In the present invention, "protein degradation" refers to a process in which the protein is degraded by the proteasome after being ubiquitinated.

In the present invention, "Luciferase assay" refers to a Luciferase system in which a luciferin is used as a substrate to detect a firefly luciferase (Luciferase) Activity of a reporting system. Luciferase can catalyze the formation of fluorescent luciferin (oxyluciferin), in the process of fluorescein oxidation, will emit bioluminescence (Bioluminescence). The bioluminescence released during the oxidation of the fluorescein can then be measured by a fluorometer, also known as a Luminoineter or a liquid scintillation counter. Fluorescein and luciferase, a bioluminescent system, is extremely sensitive and efficient detection of gene expression, which is a detection method that detecting the interaction of transcription factor and the target gene promoter region.

The invention adopts the androgen receptor luciferase assay to select Ailanthone from a plurality of Traditional Chinese Medicine Library. It is mainly found in the seeds, root bark and bark of *Ailanthus altissima* (Mill.) Swingle and its molecular weight is 376.405 and CAS number is 981-15-7. Modern research shows that *Ailanthus* has anti-amoebic dysentery, anti-malaria, anti-ulcer and other effects. But so far there is not any research on its anti-prostate cancer effectiveness. The invention proves that the compound can effectively inhibit the growth and metastasis of the prostate cancer cell in vivo and in vitro.

Compared with Bicalutamide and MDV3100 that have been approved by the FDA, Ailanthone has the advantages that it has a wide range of sources because the ailanthus trees for extracting the compound are widespread in China. Ailanthone was included in the "Chinese Pharmacopoeia" for many years and used for many years in China, which has the potential for developing of proprietary Chinese medicines (compound) potential.

Second, the drugs in clinical are almost ineffective for androgen receptor mutated prostate cancer cells, and ailanthone still have good killing effects on MDV3100-resistant prostate cancer cells, which indicates that for MDV3100-resistant prostate cancer, the application of the invention is still valid.

In addition, the mechanism of the compound used in the application of the present invention is relatively clear. It is found that the compound inhibit the growth and migration of prostate cancer cells in low concentration (<1 µM) significantly; In mice model, 2 mg/kg/d of can inhibit prostate cancer cells growth and metastasis in vivo. Experiments show that Ailanthone inhibit the androgen receptor activity by binding to p23 and suppress its binding with molecular chaperone Hsp90. These action induced androgen degradation and down-regulation androgen receptor protein levels, and then inhibit the downstream gene expression and androgen receptor signaling pathway.

In conclusion, we screened and characterized AIL, which has excellent drug-like characteristics that is able to overcome MDV3100-resistance in prostate cancer cell lines. AIL was efficacious in suppressing the growth and metastasis of CRPC via targeting p23. As a result, AIL can be considered a new potential drug candidate for prostate cancer, and it is worthy of further research and investigation.

AR mediates transcriptional programs in CRPC distinctly[38]. Current therapies have concentrated on the androgen-dependent activation of AR through its LBD, but do not provide a continuing clinical benefit for patients with CRPC and presumably fail due to multiple mechanisms including the expression of a constitutively active splice variant AR lacking the LBD. These AR-Vs can signal in the absence of ligand and are therefore resistant to LBD-targeting AR antagonists or agents that repress androgen biosynthesis[13, 14, 39].

In this work, we identified a natural AIL compound which potently blocked the activities of ligand-induced full-length AR and constitutively active truncated AR which lacks the LBD. Moreover, this compound reduced the expression of both the full-length AR and the truncated AR in vitro and in vivo. Furthermore, AIL was able to inhibit MDV3100-resistant AR-Vs expressing PCa. Notably, not only i.p. administration but also p.o. administration of AIL had excellent efficiency for blocking the growth of CRPC xenografts. In pharmacokinetic studies, AIL exhibited good solubility in water and good bioavailability (>20%). In addition, AIL effectively suppressed CRPC tumor growth, despite not reaching a steady state of plasma drug concentration during the course of treatment. The stomach injury we observed may be attributable to gastrointestinal toxicity of AIL after oral administration, which is likely to be dosage dependent. Thus, if we shorten the treatment time interval or reduce the dosage of AIL, it would become even more effective and less toxic. In addition, we also addressed some key safety issues of AIL, such as CYP inhibition and hepatotoxicity. In vitro CYP inhibition data are particularly important during drug discovery for providing early warning of potential safety issues and for planning human clinical studies. Hence, the U.S. Food and Drug Administration (FDA) recommended that CYP-associated metabolic studies in vitro should be performed. The current study showed that AIL had no obvious inhibitory effects on the main CYPs in humans and rats, including CYP1A2, CYP2C9 (human)/2C11 (rat), CYP2D1 (rat)/2D6 (human), CYP2E1 and CYP3A1/2 (rat)/3A4 (human) isoforms. In addition, AIL did not influence the expression of CYP enzymes and had no significant hepatotoxicity after a 5-day administration in the present study. Therefore, AIL would have a low potential to cause possible toxicity and drug-drug interactions involving CYP enzymes, suggesting a sufficient safety window for its putative use as a promising anticancer agent. Meanwhile, various physicochemical properties of AIL were calculated on the ACD/I-Lab and the results showed that the physiochemical parameters of the natural compound AIL met with "Lipinski's Rule of Five". Indeed, compounds possessing properties that exceed the Lipinski rules tend to have low oral bioavailability. Our results suggest that, if potential gastrointestinal toxicity can be overcome through dosage modulation, AIL can be developed as a potential drug candidate with various drug formulations because of its ideal solubility and bioavailability.

Figure 16A:
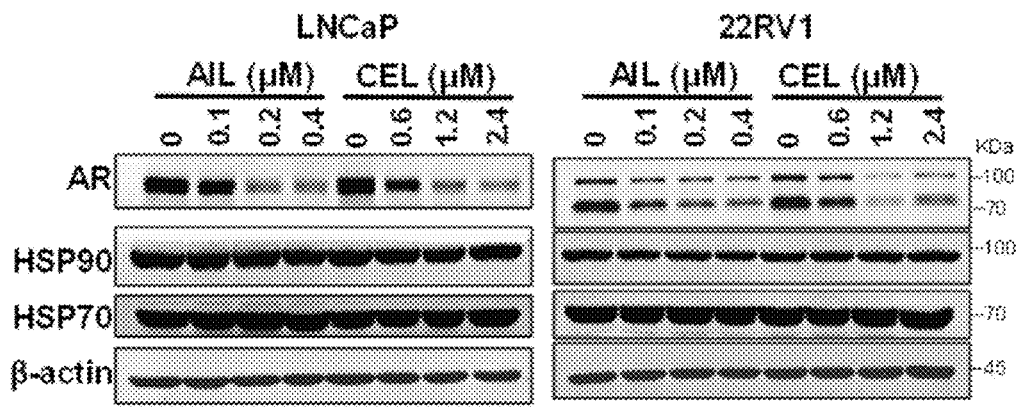
FIG. 16A-FIG. 16E. AIL and a p23 inhibitor celastrol (CEL) showed the same effects on the protein level of AR, HSP90 and HSP70. (A) LNCaP and 22RV1 cells were treated for 12 hours with the indicated concentrations of AIL or CEL (a p23 inhibitor). Cells were lysed and AR, HSP90 and HSP70 protein levels were measured by Western blot analysis. (B) p23 knockdown abrogated AIL induction of cell growth arrest. 22RV1 cells with transient transfection of non-target control (si-NC), siRNA-AR or siRNA-p23 siRNAs were treated with indicated concentrations of AIL for 72 h and cell growth was detected with the SRB assay (n=5). Data was expressed as mean±s.d.; Student's t-tests were performed; *P<0.05, P<0.01, *P<0.001. (C, D) Knockdown of AR-Vs decreased cell proliferation. VCap (C) and 22RV1 (D) cells were transfected with the AR-Vs specific siRNA pool or non-target control and the cell growth was detected with the SRB assay at the indicated times (n=5). siRNAs were transfected every two days to maintain the knockdown efficiency. Data represent the mean±s.d. P<0.01, *P<0.001 by one-way ANOVA followed by Bonferroni multiple comparison test. (E) Overexpression of p23 rescued the AIL-mediated cell growth inhibition. 22RV1 cells were transfected with empty vector or different doses of p23 plasmid in the presence of 0.2 µM for 72 hours and the cell growth was detected with the SRB assay (n=5). Data was expressed as mean±s.d.; Student's t-tests were performed; *P<0.05, P<0.01, *P<0.001.
Figure 16B:
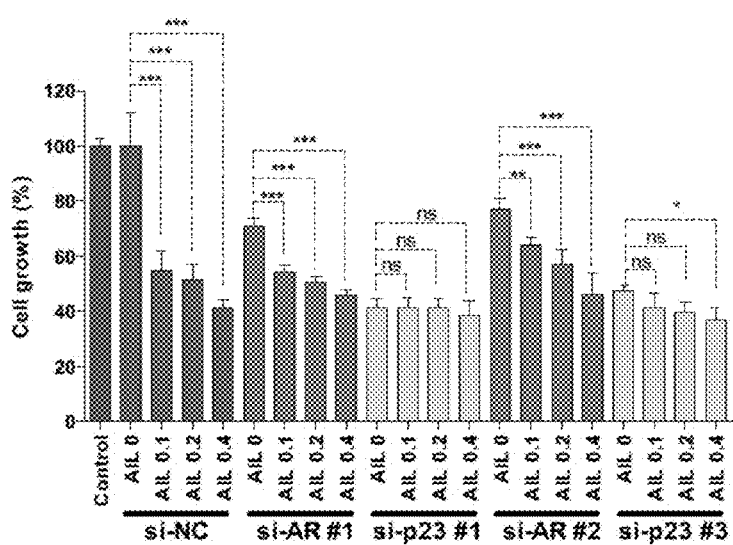

This study also explored the mechanism of AIL-induced AR degradation. We found that AIL disrupted the interaction between AR and the chaperones HSP90, HSP70 and HSP40, and consequently AR was ubiquitinated and degradated through the proteasome-mediated pathway. When not bound to ligand, AR resides in the cytosol, bound to the foldosome, a complex of heat shock, chaperone and co-chaperone proteins including HSP90, HSP70, HSP40 and p23, amongst others[24]. The HSP90 dimer undergoes an ATP-driven reaction cycle. Various cofactors were regulated in this cycle: CDC37, which delivers certain kinase substrates to HSP90 and inhibits the ATPase activity; HOP, which reversibly links together the protein chaperones Hsp70 and Hsp90; p23, which stabilizes the dimerized form of HSP90 before ATP hydrolysis[36]; and HDAC6, which mediates acetylation/deacetylation of HSP90[40]. Inhibiting the chaperone HSP90 causes AR instability or blocks nuclear transiocation[41, 42, 43]. Since AIL did not bind to HSP90 or affect chaperone expression, our results suggest that AIL is not an ATP competitive inhibitor of HSP90 like 17-AAG. However, AIL could bind to p23 protein which is very important for the stabilization of the HSP90-complex[36] and AIL prevented the interaction of HSP90 with p23. Given that AIL was able to bind to p23 and knockdown of p23 substantially prevented AIL-induced cell growth arrest (FIG. 5B and FIG. 16B), we conclude that AIL induces AR degradation through binding to p23 and disrupting the HSP90-client complex. Furthermore, constitutively active AR variant expression does not confer resistance to AIL. Indeed, recent papers have shown that constitutively active AR variants played their roles independently of the HSP90 chaperone but did not confer resistance to HSP90 inhibitors[44, 45], indicating that the mechanisms of AIL also include HSP90 complex inhibition. Not surprisingly, AIL also suppressed the activities of other nuclear receptors including progesterone (PR) and glucocorticoid receptor (GR) (FIG. 13G), indicating that repression of glucocorticoid and progesterone receptor signaling might contribute the therapeutic efficiencies of AIL in CRPC. At higher concentrations (up to 10 μM as well as 50 μM), AIL also significantly decreased the cell growth of PC3 and DU145 (FIG. 1E and FIG. 8), which might be caused by the degradation of other p23 clients (AKT and Cdk4). Indeed, prostate cancer cells that express AR showed greater sensitivity to inhibition of growth by AIL at lower concentration, suggesting the degradation of AR by AIL plays a major role in inhibiting cell growth of AR-positive prostate cancer cells at low concentrations of AIL. Alternatively, the degradation of AR and other clients including AKT and Cdk4 may have induced synthetic lethality by blocking multiple signal pathways in AR positive cells, rendering AR positive cell lines sensitive to AIL. Knockdown of AR achieved only about 30% growth inhibition, whereas p23 knockdown was more effective in inhibiting 22Rv1 cell growth (FIG. 16B), suggesting that other downstream targets of AIL mediated by the inhibition of p23, such as AKT. Cdk4 or others are important for prostate cancer cell growth inhibition. Therefore, we conclude that targeting p23 is the major mechanism of AIL. Meanwhile, AIL-induced AR degradation is at least a critical mechanism of AIL-dependent cell growth inhibition in prostate cancer. Since overexpression of p23 could not totally rescue the AIL-induced cell growth inhibition (FIG. 16E), we conclude that p23 also has other potential targets including protein synthesis[46].

In fact, how AIL regulates the molecular conformation of p23 and prevents the interaction of p23 with HSP90 remains undetermined in our work. Clarifying the mechanism of AIL remains to be further investigated.

P23 is able to increase the AR protein level and AR transcriptional activity which is independent of its role in the HSP90 foldosome complex[30]. Significantly, p23 expression is implicated in resistance to HSP90 inhibitors[28], and plays a role in PCa metastasis. Consequently, inhibition of p23 is likely to counteract CRPCs that have developed resistance to HSP90 inhibitors, and AIL may serve to synergistically enhance the efficacy of HSP90 inhibition in ablating CRPC in addition to its efficacy as a solitary agent against CRPC. CEL which effectively inhibits prostate cancer cells[47, 48] as been reported to inhibit p23 function and to bind to three cystine residues of p23: Cys-40, Cys-58, and Cys-75[49]. Importantly, our molecular modeling indicates that AIL binds to a different region of p23 (FIG. 5C), suggesting that AIL has the potential to synergize with CEL in inhibiting p23. Finally p23 has also been implicated in breast cancer lymph node metastasis and drug resistance[31], highlighting the potential value of AIL in treating multiple cancer types.

In conclusion, we screened and characterized AIL, a novel compound with excellent drug-like characteristics that is able to overcome MDV3100-resistance in prostate cancer cell lines. AIL was efficacious in suppressing the growth and metastasis of CRPC via targeting p23, making it a novel drug candidate for treatment of cancers, especially prostate cancer.

As used throughout this description, the term "acyl" refers to a group having the general formula —C(═O)R$_7$, —C(═O)OR$_7$, —C(═O)—O—C(═O)R$_7$, —C(═O)SR$_7$, —C(═O)N(R$_7$)$_2$, —C(═S)R$_7$, —C(═S)N(R$_7$)$_2$, —C(═S)SR$_7$, —C(═NR$_7$)R$_7$, —C(═NR$_7$)OR$_7$, —C(═NR$_7$)SR$_7$, and —C(═NR$_7$)N(R$_7$)$_2$, wherein R$_7$ is hydrogen; halogen; substituted or unsubstituted hydroxyl; substituted or unsubstituted thiol; substituted or unsubstituted amino; substituted or unsubstituted acyl, cyclic or acyclic; substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; cyclic or acyclic, substituted or unsubstituted, branched or unbranched alkynyl; substituted or unsubstituted aryl; substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkyloxy, heteroalkylthioxy, arylthioxy, heteroarylthioxy.

As used throughout this description, the term "aliphatic" includes both saturated and unsaturated, nonaromatic, straight chain, branched, acyclic, and cyclic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Aliphatic group substituents include, but are not limited to any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphatictioxy, heteroaliphaticticoxy, alkylthioxy, heteroalkyithioxy, arylthioxy, heteroarylthioxy, acyloxy, and the like, each of which may or may not be further substituted).

As used throughout this description, the term "alkyl" refers to saturated, straight- or branched-chain hydrocarbon radicals derived from a hydrocarbon moiety containing between one and twenty carbon atoms by removal of a single hydrogen atom. In some embodiments, the alkyl group employed the invention contains 1-20 carbon atoms. Examples of alkyl radicals include, but are not limited to, methyl, ethyl, propyl, n-propyl, isopropyl, butyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents. Alkyl group substituents include, but are not limited to any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphatictioxy, heteroaliphaticticoxy, alkylthioxy, heteroalkylthioxy, arylthioxy, heteroarylthioxy, acyloxy, and the like, each of which may or may not be further substituted.

As used throughout this description, the term "alkenyl" denotes a monovalent group derived from a straight- or branched-chain hydrocarbon moiety having at least one carbon-carbon double bond by the removal of single hydrogen atom. In certain embodiments, the alkenyl group employed in the invention contains 2-20 carbon atoms. Alkenyl groups include, for example, ethenyl, propenyl, butenyl, 1-methyl-2-buten-1-yl, and the like, which may bear one or more substituents. Alkenyl group substituents include, but are not limited to, any of substituents described herein, that result in the formation of a stable moiety (e.g., aliphatic, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphatictioxy, heteroaliphaticticoxy, alkylthioxy, heteroalkylthioxy, arylthioxy, heteroarylthioxy, acyloxy, and the like, each of which may or may not be further substituted). In an alkenyl group, a C═C double bond for which the stereochemistry is not specified (e.g. —CH═CHCH$_3$,

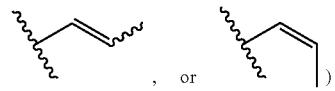

, or )

may be in the (E)- or (Z)-configuration.

The present invention discloses a pharmaceutical composition comprising the aforementioned ailanthone compound, and at least one pharmaceutically acceptable excipient. If needed, one or more pharmaceutically acceptable carriers or excipients may also be included in the pharmaceutical composition. The carriers include diluents, vehicles, bulking agents, bonding agents, wetting agents, disintegrating agents, absorption enhancers, surfactants, sorption carriers, lubricants etc. ordinary in the pharmaceutics.

Such compositions comprise a therapeutically or prophylactically effective amount of the ailanthone compound in admixture with pharmaceutically acceptable materials, and physiologically acceptable formulation materials. The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants. (Remington's Pharmaceutical Sciences, 18$^{th}$ Edition, A. R. Gennaro, ed., Mack Publishing Company, 1990).

The optimal pharmaceutical composition will be determined by one skilled in the art depending upon, for example, the intended route of administration, delivery format, and desired dosage. See for example, Remington's Pharmaceutical Sciences, supra. Such compositions may influence the physical state, stability, rate of in vivo release, and rate of in vivo clearance of the polypeptide. For example, suitable compositions may be water for injection, physiological saline solution for parenteral administration.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffers, or acetate buffers, which may further include sorbitol or a suitable substitute thereof. In one embodiment of the present invention, compositions may be prepared for storage by mixing the selected composition having the desired degree of purity with optional formulation agents (Remington's Pharmaceutical Sciences, supra) in the form of a lyophilized cake or an aqueous solution. Further, the therapeutic composition may be formulated as a lyophilizate using appropriate excipients such as sucrose.

The formulations can be delivered in a variety of methods, for example, by inhalation therapy, orally, or by injection. When parenteral administration is contemplated, the therapeutic compositions for use in this invention may be in the form of a pyrogen-free, parenterally acceptable aqueous solution comprising the desired polypeptide in a pharmaceutically acceptable vehicle. A particularly suitable vehicle for parenteral injection is sterile distilled water in which a polypeptide is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In another aspect, pharmaceutical formulations suitable for injectable administration may be formulated in aqueous solutions, preferably in physiologically compatible buffers such as Hanks' solution, Ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions. In another embodiment, a pharmaceutical composition may be formulated for inhalation. Inhalation solutions may also be formulated with a propellant for aerosol delivery. In yet another embodiment, solutions may be nebulized.

It is also contemplated that certain formulations may be administered orally. In one embodiment of the present invention, molecules that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the therapeutic molecule. Diluents, flavorings, low melting point waxes, vegetable oils, lubricants, suspending agents, tablet disintegrating agents, and binders may also be employed. Pharmaceutical compositions for oral administration can also be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally also include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Additional pharmaceutical compositions will be evident to those skilled in the art, including formulations involving polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art. See for example, PCT/US93/00829 that describes controlled release of porous polymeric microparticles for the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919, EP 58,481), copolymers of L-glutamic acid and gamma ethyl-L-glutamate (Sidman et al., Biopolymers, 22:547-556 (1983), poly (2-hydroxyethyl-methacrylate) (Langer et al., J. Biomed. Mater. Res., 15:167-277, (1981); Langer et al., Chem. Tech., 12:98-105 (1982)), ethylene vinyl acetate (Langer et al., supra) or poly-D(−)-3-hydroxybutyric acid (EP 133,988). Sustained-release compositions also include liposomes, which can be prepared by any of several methods known in the art. See e.g., Eppstein et al., PNAS (USA), 82:3688 (1985); EP 36,676; EP 88,046; EP 143,949.

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried ailanthone compound and a second container having an aqueous formulation. Also included within the scope of this invention are kits containing single and multi-chambered pre-filled syringes (e.g., liquid syringes and lyosyringes).

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the polypeptide is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 mg/kg to up to about 100 mg/kg or more, depending on the factors mentioned above. Polypeptide compositions may be preferably injected or administered intravenously. Long-acting pharmaceutical compositions may be administered every three to four days, every week, or biweekly depending on the half-life and clearance rate of the particular formulation. The frequency of dosing will depend upon the pharmacokinetic parameters of the polypeptide in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

The route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, intralesional routes, intramedullary, intrathecal, intraventricular, transdermal, subcutaneous, or intraperitoneal; as well as intranasal, enteral, topical, sublingual, urethral, vaginal, or rectal means, by sustained release systems or by implantation devices. Where desired, the compositions may be administered by bolus injection or continuously by infusion, or by implantation device. Alternatively or additionally, the composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

The compositions of the present disclosure may be used alone or in combination with other therapeutic agents to enhance their therapeutic effects or decrease potential side effects.

Another object of the present invention is to provide methods preparing the above ailanthone compound and the pharmaceutical composition comprising it. The preparation may be carried out with proven and well-known technologies by an ordinarily skilled artisan.

Another object of the present invention is to provide method of treating cancer using the pharmaceutical composition of the present invention comprising administrating an effective amount of the aforementioned pharmaceutical composition to the patients or subjects in need thereof. In one embodiment, the pharmaceutical composition is used to treat cancers that has or depends on abnormally enhanced androgen receptor activity, which enhanced activity allows the proliferation, metastasis, growth, cloning formation of cancer cells. These cancers include but are not limited to prostate cancer, breast cancer, lung cancer, colon cancer, brain cancer, skin cancer, bladder cancer, and renal cell carcinoma. Other cancers suitable for treatment by the method of the present invention include acute myeloid leukemia (AML), chronic myeloid leukemia (CML), acute lymphoblastic leukemia (ALL), non-hodgkins lymphoma (NHL), multiple myeloma (MM), bladder cancer, ovarian cancer, colon cancer, pancreatic cancer and renal cancer.

In one embodiment, the pharmaceutical composition can be used to treat other related conditions having overly active or abnormally enhanced androgen receptor activity, such as androgen excess, defined by the presence of clinical hyperandrogenism and/or biochemical hyperandrogenemia. Examples of androgen excess diseases include but are not limited to Polycystic Ovary Syndrome (PCOS), Congenital Adrenal Hyperplasia (CAH) and Premature Adrenarche

EXAMPLES

The following examples are given for further illustrating the specific solutions of the present invention.

Materials and Methods

Cell Culture

Prostate cancer cell lines c4-2b, LAPC4 and normal prostate epithelial cell line RWPE-1 used in this study were kindly provided by Dr Ying-Hao Sun (Department of Urology, Changhai Hospital, Shanghai, China). Other human prostate cancer cell lines were purchased from the Cell bank of the Chinese Academy of Science. The cell lines were authenticated by short tandem repeat analysis and mycoplasma contamination was tested by the PCR Mycoplasma Detection Set (Takara, Otsu, Japan). 293T cells were routinely maintained in DMEM (GBICO), while prostate cancer cells were cultured in RPMI 1640 (GBICO). Media were supplemented with 10% FBS (BioWest, cat. no. S1580-500) and 1% penicillin/streptomycin unless otherwise specified. RWPE-1 was cultured in serum-free medium (Invitrogen, Carlsbad, Calif.).

Dual Luciferase Screening Assay

For dual luciferase screening assay, prostate cancer cells were transfected with MMTV-luc, Renilla-luc (phRL-TK, Promega), ARor $AR_{1-651}$ (vector: pFLAG-CMV-1) plasmids (provided by DrJie-Min Wong)[50] using lipofectamine 2000 (Invitrogen) according to the manufacturer's instructions. After transfection for 24 hours, the transfected cells were treated with DHT (Sigma, cat. no. A8380) or DHT with compounds for 12 hours. Renilla and firefly activities were then determined by luminometry using the Dual-Luciferase Reporter Assay System (Promega) and the ratio calculated. Results were expressed as the ratio of firefly to Renilla luciferase activity.

Quantitative Real-Time PCR

Cells were cultured with RPMI 1640 with 5% charcoal dextran treated FBS for 5 days prior to treatment with R1881 (Sigma, cat. no. R0908) alone or R1881 and AIL for 12 h. Total RNA was extracted using TRIzol (Takara, Japan) according to the manufacturer's instructions. 1 µg of total RNA was used for cDNA synthesis using a cDNA reverse transcription kit (Takara, Japan). Real-time PCR was performed in triplicate using gene-specific primers on a Stratagene Mx3005P PCR system (Agilent Technologies) machine. The mRNA expression levels were normalized to β-actin expression or GAPDH. All analysis was performed using Microsoft Excel 2010 and GraphPad Prism 5 software. The gene-specific primers are listed in Table 1.

TABLE 1

Sequences of quantitative-PCR primers

| SEQ ID NO | Name of Gene | Primer (5' to 3') |
| --- | --- | --- |
| SEQ ID NO. 1 | AR-F | GGTGAGCAGAGTGCCCTATC |
| SEQ ID NO. 2 | AR-R | GAAGACCTTGCAGCTTCCAC |
| SEQ ID NO. 3 | PSA-F | CTTGTAGCCTCTCGTGGCAG |
| SEQ ID NO. 4 | PSA-R | GACCTTCATAGCATCCGTGAG |
| SEQ ID NO. 5 | TMPRSS2-F | CTGGTGGCTGATAGGGGATA |
| SEQ ID NO. 6 | TMPRSS2-R | GGACAAGGGGTTAGGGAGAG |
| SEQ ID NO. 7 | NDRG1-F | CGAGACTTTACATGGCTCTGT |
| SEQ ID NO. 8 | NDRG1-R | TCCATGGAGGGGTACATGTA |
| SEQ ID NO. 9 | FKBP5-F | AGAACCAAACGGAAAGGAGA |
| SEQ ID NO. 10 | FKBP5-R | GCCACATCTCTGCAGTCAAA |
| SEQ ED NO. 11 | SLC45A3-F | GCAGTGAGGACAGCCTGATG |
| SEQ ID NO. 12 | SLC45A3-R | CGGAGACATCACAGGCAGAG |
| SEQ ID NO. 13 | GAPDH-F | ACCCAGAAGACTGTGGATGG |
| SEQ ID NO. 14 | GAPDH-R | TTCAGCTCAGGGATGACCTT |
| SEQ ID NO. 15 | β-actin-F | GTACGCCAACACAGTGCTG |
| SEQ ID NO. 16 | β-actin-R | CGTCATACTCCTGCTTGCTG |
| SEQ ID NO. 17 | AR-v7-F | AAAAGAGCCGCTGAAGGGAA |
| SEQ ID NO. 18 | AR-v7-R | CCAACCCGGAATTTTTCTCCC |

Sulforhodamine B (SRB) Assay

For sulforhodamine B (SRB) assay, cells were cultured in complete RPMI 1640 and incubated with indicated concentrations of AIL or cells were maintained in fresh phenol red-free RPMI 1640 medium with 5% charcoal-stripped FBS (c-FBS; Wisent), 1 nM DHT and indicated compounds. After 48 h or 72 h the cells were then fixed and the cell growth was detected with the sulforhodamine B (SRB) assay[51]. Ailanthone (AIL) was purchased from Shanghai Zhanshu Chemical Technology, Co., Ltd (Shanghai, China). Bicalutamide (BIC) and MDV3100 (MDV) were purchased Selleckchem.

Cell Colony Formation Assay

For colony formation assay, prostate cancer cells were incubated with indicated concentrations of AIL in complete RPMI 1640 for two weeks and then cells were fixed with 4% paraformaldehyde and stained with crystal violet. Colonies were visualized under a microscope, and all of the fields were imaged and counted. Colony formation as a % of vehicle control for each cell line is presented.

Western Blotting

Cells were treated as described in the corresponding section of Results and then lysed by boiling for 10 min in sample buffer (2% SDS, 10% glycerol, 10% β-Mercaptoethanol, Broinphenol Blue and Tris-HCl, pH 6.8). Lysates were fractionated on polyacrylamide gels and transferred to nitrocellulose. The blots were probed with specific antibodies followed by secondary antibody then membranes were examined using the LI-COR Odyssey infrared imaging system (LI-COR Biotechnology, Lincoln Nebr.). The AR (N20, sc-816 and H280, sc-13062; 1:1000), HSP90 (sc-7947; 1:1000), and Cdk4 (se-260; 1:1000) antibodies were purchased from Santa Cruz Biotechnology (Santa Cruz, Calif.). The HSP70 (1776-1; 1:5000), HSP40 (3532-1; 1:1000), and Ubiquitin (1646-1; 1:1000) antibodies were purchased from Epitomics (Burlingame, Calif.). p23 (ab92503; 1:1000) and Hop (ab126724; 1:1000) antibodies were purchased from Abcam (Cambridge, Mass.). Akt (4691; 1:1000) and HDAC6 (7558; 1:1000) antibodies were purchased from Cell Signaling Technology (Danvers, Mass.). CDC37 (4222S; 1:1000) antibody was purchased Biogot Biotechnology Co., Ltd (Shanghai, China). The β-actin antibody (1:10000) was purchased from Sigma (St. Louis, Mo.). The secondary antibody was conjugated with IRDye 680/800 (Millennium Science; 926-32221, 926-32210; 1:10000). Uncropped blots are shown in FIG. 19.

Co-Immunoprecipitation

22RV1 and LNCaP cells were treated with or without AIL in the presence of 10 μM MG132. After 24 h, cells were washed with cold PBS and harvested in immunoprecipitation buffer (0.1% Triton X-100, 2 mg ml$^{-1}$ aprotinin, 100 mg ml$^{-1}$ PMSF, 100 mM NaCl in 50 mM Tris-HCl, pH 7.2). The lysate was lysed for 1 h at 4° C. and centrifuged at 16000 g. The supernatants were incubated with 2 μg antibody to AR (Santa cruz, H280), HSP90 (Santa cruz, sc-7947) or HSP70 (Epitomics, 1776-1) with 20 μl of protein A/G (Abmart) and rocked for 2.5 h at 4° C. The protein A/G beads were pelleted and washed three times with immunoprecipitation wash buffer. The precipitates were resolved on SDS-PAGE gel and subjected to Western blot analysis.

In Vivo Subcutaneous Tumor Growth Xenograft Models

BALB/c-nude mice (6-8 week old, male) were purchased from the Sino-British Sippr/BK Lab Animal Co., Ltd (Shanghai, China) and maintained under pathogen-free conditions. The animal use protocol was approved by the Institutional Animal Care and Use Committee of East China Normal University. The 22RV1, LNCaP and VCaP xenograft tumor models were developed by injecting 3×10$^6$ 22RV1 cells or 5×10$^6$ LNCaP or VCaP cells in suspension into the right flank of a BALB/c-nude mouse; cells were suspended in 100 μl PBS or 50% matrigel (LNCaP and VCaP) respectively. Specifically for LNCaP and VCaP cells, continuous release testosterone pellets (15 mg testosterone per pellet, Sigma-Aldrich) were implanted subcutaneously to stimulate the growth of LNCaP and VCaP xenografts. Tumor nodules were allowed to grow to a volume about 100 mm$^3$ before initiating treatment. Tumor-bearing BALB/c-nude mice were randomly assigned to three groups and treated with the indicated compound or drug. The tumor volume and mouse body weight were measured twice a week. The tumor volume was calculated using the following equation: tumor volume (V)=length×width×width×0.52.

Orthotopic Castration Resistant Prostate Cancer Model

For orthotopic castration resistant prostate cancer xenografts, male BALB/c-nude mice (8-9 weeks of age) were anesthetized using 150 mg kg$^{-1}$ 2,2,2-tribromethanol plus 350 mg kg$^{-1}$ tert-amyl alcohol and then 5×10$^5$ 22RV1-luc cells suspended in 30 μl 50% matrigel were surgically injected into the dorsolateral prostate lobes. One week after injection, the tumor-bearing mice were castrated and randomly assigned to three groups. A week later, animals were intraperitoneally injected with AIL (2 mgkg$^{-1}$), MDV (10 mg kg$^{-1}$) or DMSO (as controls). Prostate tumor growth and local metastasis were monitored weekly using the IVIS Imaging System (Xenogen Corporation, Alameda, Calif.). Images and measurements of bioluminescent signals were acquired and analyzed using Living Image and Xenogen software[52].

Histology and Immunohistochemistry (IHC)

Tumors or mouse tissue samples were immediately fixed in 10% neutral buffered formaldehyde for 24 hours, progressively dehydrated in solutions containing an increasing percentage of ethanol (75, 85, 95 and 100%, v/v), and embedded into paraffin blocks. For immunohistochemical (IHC) staining, sections were cut from the paraffin blocks and IHC was carried out using anti-Ki-67 (1:250), and anti-AR (1:50; N-20) as primary antibodies. Samples were stained with hematoxylin-eosin (HE) to indicate nucleus and cytoplasm, respectively.

Geldanamycin-FITC Fluorescence Polarization Assay

Fluorescence polarization assay[53] measurement of binding affinities between AIL and p23 as well as HSP90 was used to confirm whether AIL inhibited fluorescein-conjugated geldanamycin (FITC-GA) binding to the ATPase site of the HSP90α isoform. Detailedly, FITC-GA (invivogen, Cat. No. ant-fgl-1) was dispensed into wells containing AIL at a final concentration of 0.16 nM FITC-GA. HSP90α recombinant protein (BPS, cat. no. 50290) in buffer (50 mM KCl, 5 mM MgCl2, 20 mM HEPES, pH 7.3-7.5, 0.1% CHAPS (Sigma, cat. no. C5070), 0.1% bovine gamma-globulin (Sigma, cat. no. G7516), and 2 mM dithiothreitol (Sigma, cat. no. 646563) was then added to the well at final concentration of 30 nM. For IC50 determination, 100 μM AIL was serially diluted 1:4 by transferring 20 μl into 60 μl of 100% DMSO into successive wells for a total of 10 final concentrations. As a positive control, 10 μM 17-AAG (Selleckchem, Cat. no. S1141) was serially diluted 1:10 by transferring 10 μl to 90 μl of 100% DMSO in the next well repeatedly for a total of 10 final concentrations. The assay plate was covered and incubated at 4° C. overnight. Data were collected on Victor-3 with the setting Ex480/Em535. mP values were converted to percent inhibition values. Percent inhibition=(sample RLU−min)/(max−min)×100%. "min" means the mP of no enzyme control and "max" means the mP of DMSO control. Data was graphed in MS Excel and the curves were fitted by XLFitExcel add-in version 4.3.1.

AIL-p23 Docking Studies

The protein structure of p23 was obtained from Protein Data Bank (PDB ID: 1EJF) and the PDB file was processed by removing water molecules and cations for the next docking step. Docking studies were performed by using AutodockVina 1.1.2, and all images were generated in UCSF Chimera 1.8. The protein structure of p23 was obtained from Protein Data Bank (PDB ID: 1EJF) and the PDB file was processed by removing water molecules and SO42− for the next docking step. Docking studies were performed by using AutodockVina 1.1.2, and all images were generated in UCSF Chimera 1.8. The active site was similar to the reported site[49, 54, 55]. The correlative parameters were listed in Table 2 and other parameters chosen were: num_modes=9 and exhaustiveness=16. The lowest energy conformation was chosen for binding model analysis.

TABLE 2

| Parameters of docking studies | | | |
|---|---|---|---|
| | X | Y | Z |
| Center | 3.261 | 19.118 | 33.447 |
| Size of Box | 42 | 40 | 44 |

Pharmacokinetic Studies and CYP-Associated Metabolic Studies

Pharmacokinetic studies in vivo[37] and CAT-associated metabolic studies in vitro[56] were performed using the method reported previously in our laboratory. In this study, the effects of Ailanthoneon CYP activities were investigated using rat and human liver microsomes, employing phenacetin (CYP1A2), tolbutamide (CYP2C9/11), dextromethorphan (CYP2D1/6), chlorzoxazone (CYP2E1) and testosterone (CYP3A2/4) as the probe substrates. They were analyzed on an Agilent 1260 series instrument with DAD detection and separated by an Agilent ZORBAX Eclipse XDB-C18 column (4.6×150 mm, 5 μm) with a guard column in the respective gradient elution procedure. The incubation system, sample preparation and chromatography conditions are as described previously[56].

AIL Treatment of Tumor-Bearing BALB/c-Nude Mice

22RV1 xenografts were performed as described in "In vivo subcutaneous tumor growth xenograft models" above. After the volume of a tumor nodule reached about 100 mm³, tumor-bearing BALB/c-nude mice were randomly assigned to three groups and treated with 2 mgkg⁻¹ AIL (intraperitoneal injection, i.p) or 5 mgkg⁻¹ (oral administration, p.o.) and the control group was orally treated with an equal volume of PBS (p.o.). Since we found that AIL was water soluble, AIL was dissolved in PBS in this experiment. After 30 days of treatment, all nude mice were subjected to retroorbital bleeding to obtain blood samples, and then sacrificed. Plasma samples were collected at the indicated time points after the last administration.

HPLC-MS/MS Determination of AIL Concentrations

A simple and sensitive method for the determination of Ailanthonein plasma was developed, using high-performance liquid chromatography-tandem mass spectrometry (HPLC-MS/MS). Brusatol was used as an internal standard. Separation was achieved on an Agilent Zorbax Eclipse Plus C18 column (2.1×50 mm, 1.8 μm; USA) with gradient elution using water-methanol as mobile phase at a flow rate of 0.2 mLmin⁻¹, and total run time was 7.0 min. A triple quadrupole mass spectrometer operating in the negative electrospray ionization mode with multiple reaction monitoring (MRM) was used to detect Ailanthone and IS transitions of 375.2→301.1 and 519.1→437.4, respectively. The details of this HPLC-MS/MS method and sample preparation are described in our previous study[37].

Statistical Analysis

The statistical analysis was performed by SPSS 22.0 software. The differences between control group and experimental groups were determined by one-way ANOVA. Since treatment and time course was investigated, two-way ANOVA followed by post hoc test was also applied. Data was expressed as mean and standard deviation (s.d.) and $P<0.05$ was considered significant. Pharmacokinetic parameters were calculated by WinNonlin software version 5.2.1 (Pharsight Corporation, Mountain View, USA) based on noncompartmental analysis.

AR siRNA and p23 siRNA Assay

22RV1 cells were seeded in 6-well plates and transfected with AR-siRNA and p23-siRNA (synthesized by Biotend, Shanghai, China) the next day. Transfection was performed using HyliMax REAGENT according to the manufacturer's recommendations (Dojindo Laboratories, Japan). The effect of siRNA on AR and p23 silencing was examined by Western blot 72 hours after transfection. After transfection for 16 hours, cells were treated with various concentrations of AIL for 72 hours. The gene-specific siRNAs are listed in Table 3.

TABLE 3

Sequences of si-RNA

| SEQ ID NO | Name of Gene | si-RNA (5' to 3') |
| --- | --- | --- |
| SEQ ID NO. 19 | AR siRNA-1 | GAAAUGAUUGCACUAUUGAUU |
| SEQ ID NO. 20 | AR siRNA-2 | CGUGCAGCCUAUUGCGAGAUU |
| SEQ ID NO. 21 | AR-V's pool | AR-V1: GAGGGUGUUUGGAGUCUCAUU |
| SEQ ID NO. 22 | | AR-V3: AAGAGCCGCUGAAGGAUUUUU |
| SEQ ID NO. 23 | | AR-V4: GAUGACUCUGGGAGGAUUUUU |
| SEQ ID NO. 24 | | AR-V7: GCAAUUGCAAGCAUCUCAAUU |
| SEQ ID NO. 25 | p23 siRNA | AGCUUAAUUGGCUUAGUGU (dTdT) |
| SEQ ID NO. 26 | p23 siRNA | ACACUAAGCCAAUUAAGCU (dTdT) |
| SEQ ID NO. 27 | Non-silencing control siRNA | AATTCTCCGAACGTGTCACGT (dTdT) |

Cell Cycle Analysis

After treatment with different concentrations of AIL, cells were trypsinized, washed with PBS and fixed with cold 70% ethanol at 4° C. overnight. Cells were then washed with PBS, treated with 50 μg/ml RNase at 37° C. for 20 min and stained with 20 μg/ml propidium iodide solution for 15 min at room temperature in the dark. The stained cells were analyzed using BD LSRII flow cytometry (BD Biosciences).

Cell Apoptosis Analysis

After treatment with different concentrations of AIL, cells were trypsinized, washed with PBS and stained with 20 μg/ml propidium iodide (PI) solution and Annexin V-FITC for 15 min at room temperature in the dark. The stained cells were analyzed using BD LSRII flow cytometry (BD Biosciences).

RNA-Seq

LNCaP cells were transfected with $AR_{1-651}$ or empty vector as control for 24 hours and cells were treated with or without AIL for the next 12 hours. Total RNAs were isolated from cells and RNA was isolated using RNeasy Plus Mini Kit (Qiagen). High quality (Agilent Bioanalyzer RIN >7.0) total RNAs were employed for the preparation of sequencing libraries using Illumina TruSeq Stranded Total RNA/Ribo-Zero Sample Prep Kit. A total of 500-1,000 ng of riboRNA-depleted total RNA was fragmented by RNase III treatment at 37° C. for 10-18 min and RNase III was inactivated at 65° C. for 10 min. Size selection (50 to 150 bp fragments) was performed using the FlashPAGE denaturing PAGE-fractionator (Life Technologies) prior to ethanol precipitation overnight. The resulting RNA was directionally ligated, reverse-transcribed and RNase H treated. Samples were sequenced using the Illumina HiSeq2000 platform at The Beijing Genomics Institute (BGI) in Wuhan, China. Genome-wide coverage signals were represented in BigWig format to facilitate convenient visualization using the UCSC genome browser. Gene expression was measured using RPKM (Reads Per Kilo-base exon per Million mapped reads) as described previously[1] ENREF 2.

Gene Ontology (GO) Analysis

Using DAVID Bioinformatics Resources v6.7, a web-based functional annotation tool for data analysis (http://david.abcc.ncifcrf.gov/home.jsp), we performed gene ontology (GO) analysis for biological processes (GOTERM_BP_FAT) of the $AR_{1-651}$-induced genes inhibited by AIL treatment.

ProteOn XPR36 Protein Interaction Array (Biacore Assay)

To measurement of binding affinities between AIL and p23 as well as HSP90, p23 (Abcam, cat. no. ab75542) and HSP90α (BPS, cat. no. 50290) were dissolved in PBS and immobilized onto separate erect channels of the sensor chip by general amine coupling. p23 was immobilized to around 23300 RUs and HSP90 was 43100 RUs. After baselines were stable, AIL was dissolved in PBS-T buffer flowing through the chip horizontally. 17-AAG (binding to HSP90) and celastrol (binding to p23) were performed as positive controls. Data were analyzed with ProteOn Manager™ software using the Langmuir model (A+B⇌AB) for kinetic data fitting.

Pharmacokinetic Study of Ailanthone in Rats

Sprague-Dawley rats (purchased from Shanghai SLAC laboratory animal Co. Ltd., Shanghai, China) were fasted for 12 h with free access to water prior to the pharmacokinetic study. The rats were randomized into two groups for oral administration (5 mg/kg) and intravenous injection (1 mg/kg). Blood samples were collected from the orbital plexus into heparinized centrifuge tubes at fifteen different time points between 5 min to 36 h for the oral administration group and nine time points between 5 min to 6 h for the intravenous one. The pharmacokinetic parameters were calculated by WinNonlin software version 5.2.1 based on noncompartmental analysis. Oral bioavailability was calculated as F (%)=$AUC_{0-\infty}$(p.o.)/$AUC_{0-\infty}$(i.v.)×Dose (i.v.)/Dose (p.o.).

Figure 5A:
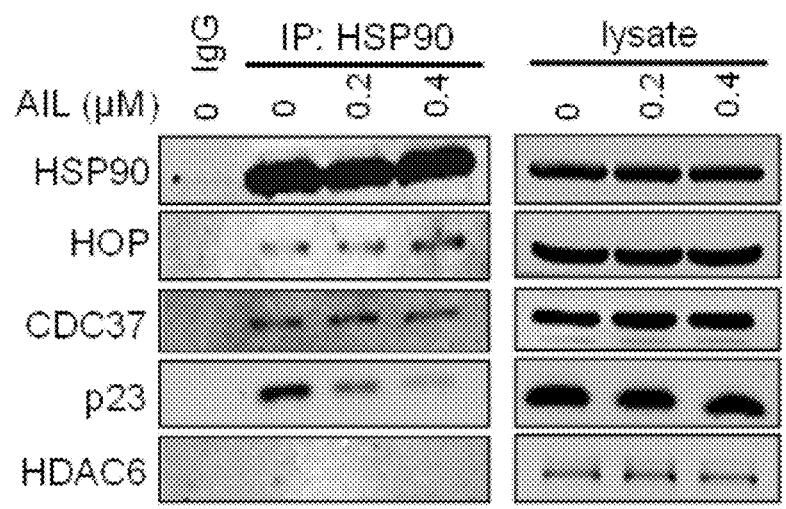
FIG. 5A-FIG. 5E. Interaction of AIL with p23 protein in vitro. (A) 22RV1 cells were treated with or without 1 μM AIL for 12 hours. Anti-HSP90 IP was done and co-immunoprecipitated proteins were detected using indicated antibodies. (B) The interaction between p23 protein and AIL was measured by ProteOn XPR36. (C) Mapping AIL binding site on p23. (D) Top: Expression level heatmap (log 2 based) of $AR_{1-651}$ induced genes which were inhibited by AIL. LNCaP cells were treated as described in Methods and the RNA samples of the indicated groups were sent for RNA-seq. First gene expression values (RPKM) were normalized (z-score transformed) across samples. Then the K-Means clustering method was used to portion all genes into the clusters with Pearson correlation as the metric of distance. In the heat map, yellow means "higher" expression and blue means "lower" expression. Bottom: Gene Ontology (GO) analysis of the $AR_{1-651}$ target genes which inhibited by AIL. (E) Schematic illustrating the mechanism of down-regulating AR protein level by AIL. When treating with AIL, the interaction of p23 and HSP90 is prevented and the interaction between AR and the molecular-chaperones is decreased, causing ubiquitination of AR. Then, AR is degraded by the proteasome, which reduces the expression of AR target genes and inhibits PCa growth and metastasis.
Figure 5B:
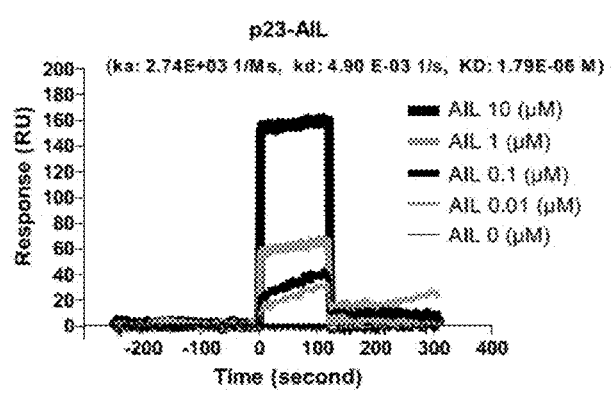
Figure 5C:
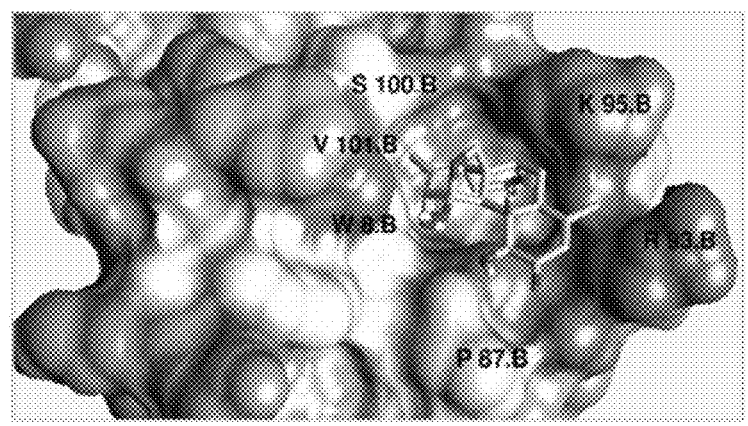
Figure 15A:
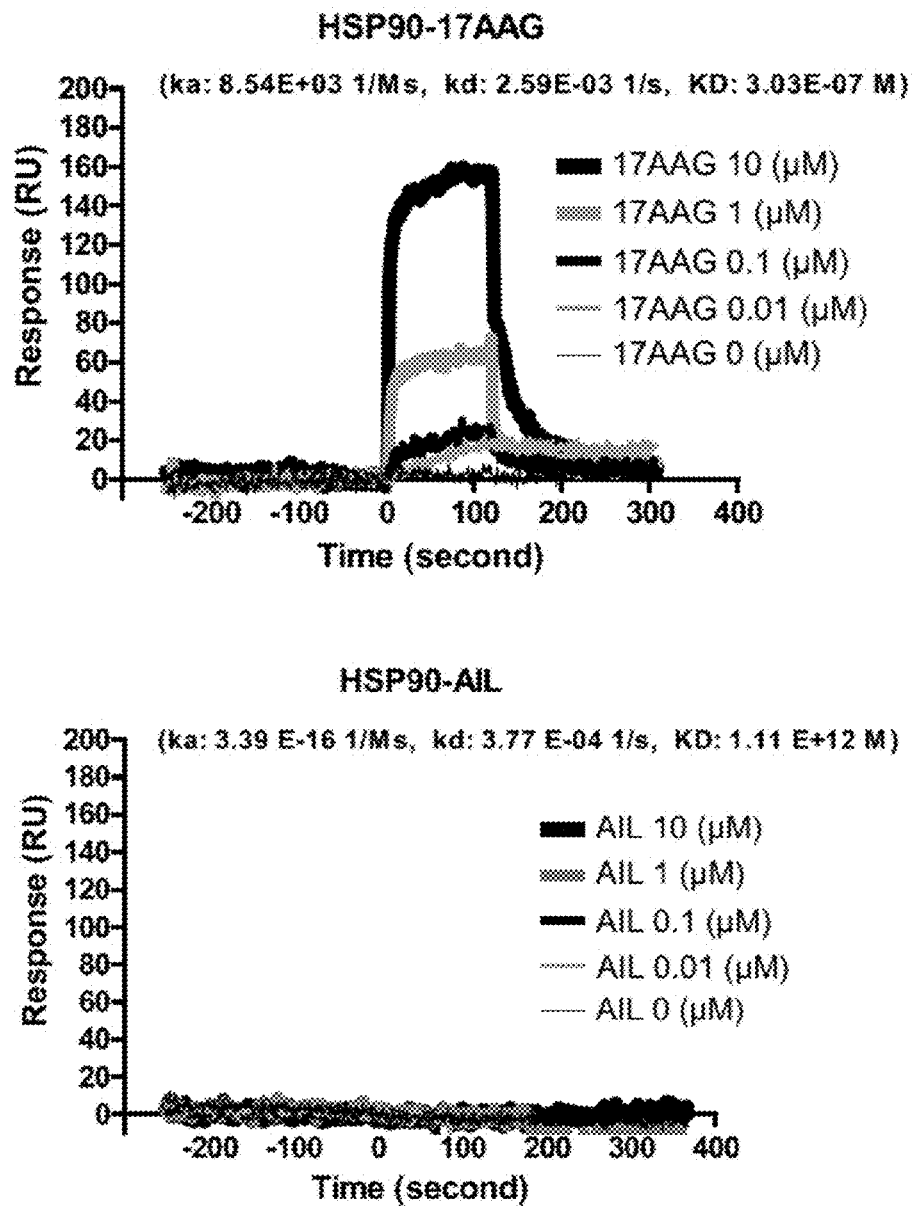
FIG. 15A-FIG. 15C. AIL binds to p23 but not HSP90. (A) HSP90 bound to 17-AAG but not AIL in vitro. The interaction between HSP90α protein and AIL (Right) or 17-AAG (Left) were measured by ProteOn XPR36. (B) Celastrol (CEL) interacted with p23 protein in vitro. The interaction between p23 protein and CEL was measured by ProteOn XPR36. (C) Mapping AIL-binding site on p23. The docking assay was performed as described in Materials and Methods.
Figure 15B:
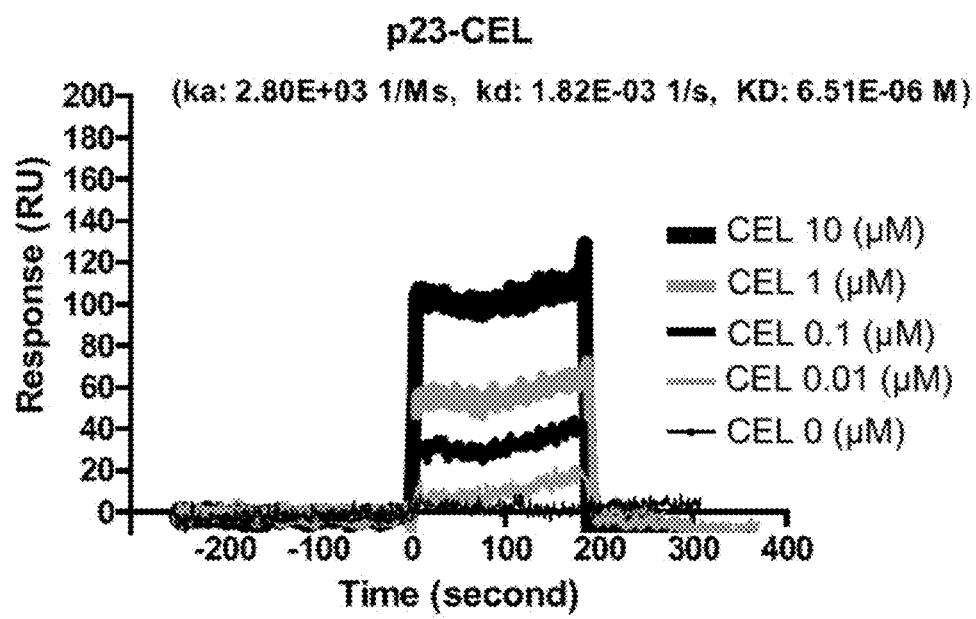
Figure 15C:
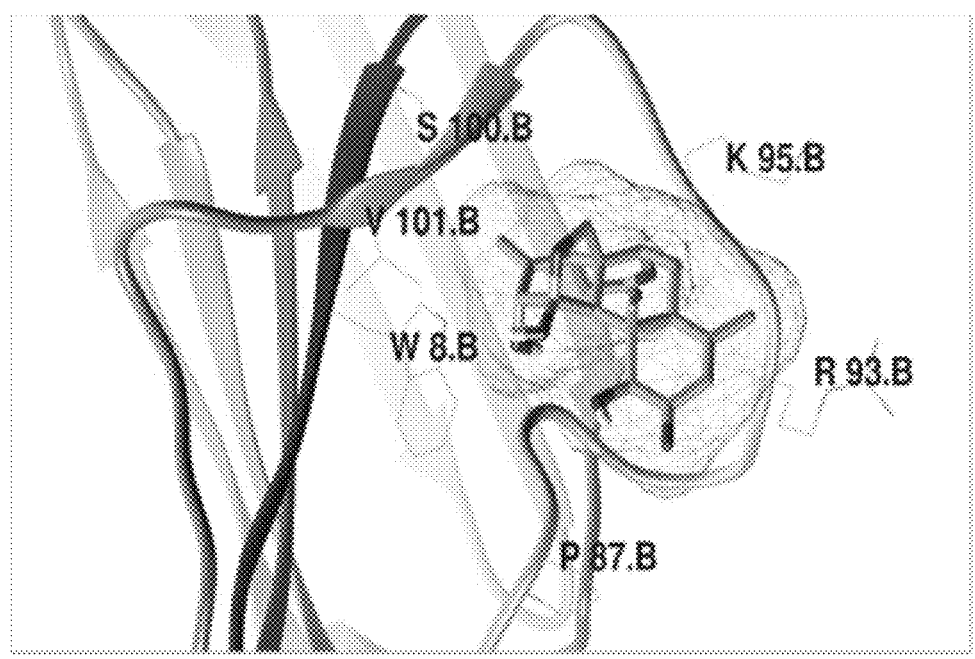

Mapping the AIL-Binding Site on p23 in order to identify how AIL bound to p23, we applied the computational docking modeling process based on the reported literature[2, 3, 4]. The docking process was shown in the AIL-p23 Docking Studies. Though analysis of docking mode, these results showed that the phenyl of residue Trp-8, as well as the alkyl parts of Ser-100, Val-100, Lys-95 and Arg-93 provided hydrophobic interactions with AIL (FIG. 5C and FIG. 15C). The indol N—H of Trp-8, the carboxyl of Pro-87 and the NH2 of Arg-93 provided the hydrophilic interactions with AIL (FIG. 5C and FIG. 15C). This binding mode provides the possibility that AIL could insert into the pocket on the surface of p23 which was formed by Ser-100, Val-100, Lys-95, Arg-93 and Trp-8.

Analysis of Physicochemical Properties of AIL

The various physicochemical properties were calculated for AIL using the ACD/I-Lab website (https://ilab.acdlabs.com/iLab2/index.php). The natural compound AIL had favorable results in physicochemical properties of partition coefficient of Log P (ACD/Labs) and surface area calculations of TPSA. According to molecular weight calculations, AIL was below 400 Da with a high oral absorption value. AIL had favorable physicochemical properties as the pKa was 12.2±1.0. The detailed data was listed in Table 4.

Example 1 AIL and its Derivatives Suppressed the Activities of AR-FL and AR-Vs

To identify compounds which inhibit the transcriptional activities of both AR-FL and constitutively active AR-Vs, we used a luciferase reporter assay to screen about 100 compounds from a library of natural compounds. 22RV1 PCa cells were either stimulated with androgen dihydrotestosterone (DHT) to activate AR-FL or transfected with $AR_{1-651}$ to introduce the splice variant of AR lacking the LBD. After incubation with these natural compounds for 12 hours, the transfected cells were harvested and AR transcriptional activity was detected by dual luciferase assay. We identified the small molecule Ailanthone (AIL) and its derivatives which potently reduced the transcriptional activities of both AR-FL and AR-Vs. The physicochemical properties of AIL are listed in Table 5.

Figure 1B:
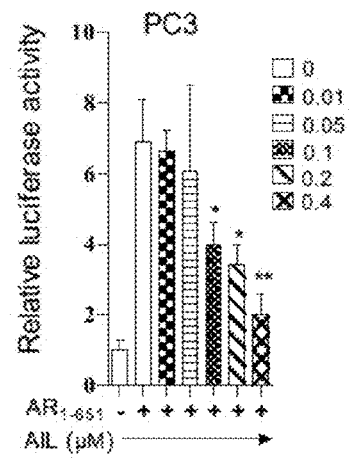
Figure 13A:
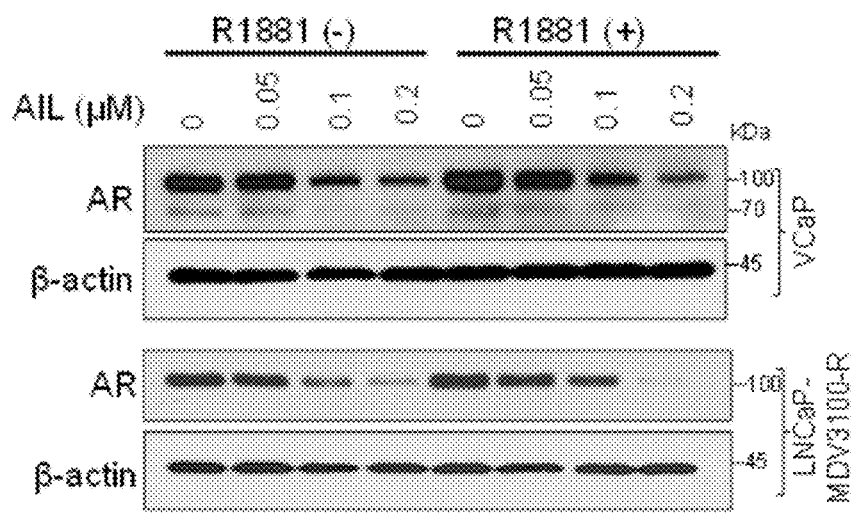
FIG. 13A-FIG. 13G. Effect of AIL on the protein levels of AR and molecular chaperones. (A) VCaP and LNCaP-MDV3100-R cells were treated for 12 hours with indicated concentrations of AIL with or without R1881 and the AR protein level was measured by Western blotting analysis. (B,C) AIL decreased the protein level of AR variants. Flag-AR-V567es (B) or Flag-AR-V7 (C) plasmids were transfected into PC3 cells. After 24 hours, cells were treated with the indicated concentrations of AIL for 12 hours and cells were lysed and AR-V7 and AR-V567es protein levels were measured by Western blot analysis using Flag antibody. (D) AIL decreased the AR protein level in both cytoplasm and nucleus. PC3 cells were transfected with AR for 24 hours and treated with or without 0.4 µM AIL in the presence of R1881 for the next 12 hours. Nucleocytoplasmic separation was done and the protein level of AR in cytoplasm and nucleus was measured by Western blot analysis. HSP90 is a cytoplasm marker and PARD is a nuclear marker. (E) HSP90 and HSP70 proteins were induced by HSP90 inhibitor 17-AAG rather than AIL. LNCaP and 22RV1 cells were treated for 12 hours with the indicated concentrations of AIL or 17-AAG. Cells were lysed and AR, HSP90 and HSP70 protein levels were measured by Western blot analysis. (F) AIL down-regulates the protein level of HSP90 clients but not the molecular chaperones. LNCaP and 22RV1 cells were treated for 24 hours with the indicated concentrations of AIL, cells were lysed and indicated protein levels were measured by Western blotting analysis. (G) Effect of AIL on the activities of androgen receptor (AR), glucocorticoid receptor (GR) or progesterone receptor (PR). PC3 cells transfected with or without AR as indicated were transiently transfected with MMTV-luc reporter plasmid and Renilla-luc plasmid, stimulated by 10 nM AR agonist DHT (left), or 10 nM PR agonist progesterone (middle), 10 nM GR agonist dexamethasone (right). Then cells were treated with different concentrations of AIL for 12 hours and the luciferase activities were measured and results were expressed as the ratio of luciferase activity. Data was expressed as mean±s.d. of three independent assays; Student's t-tests were performed; *P<0.05, P<0.01, *P<0.001.
Figure 13B:
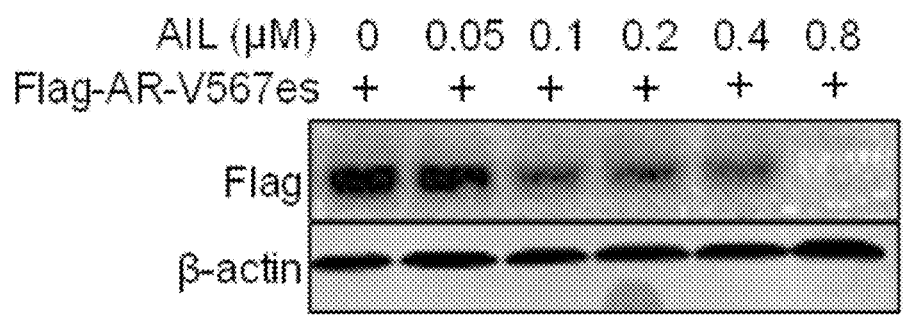
Figure 13C:
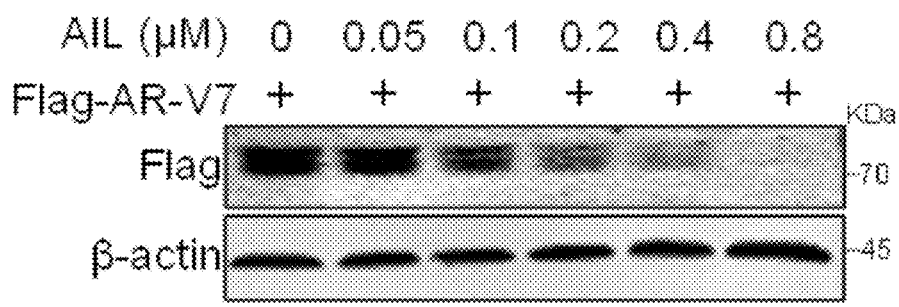
Figure 13D:
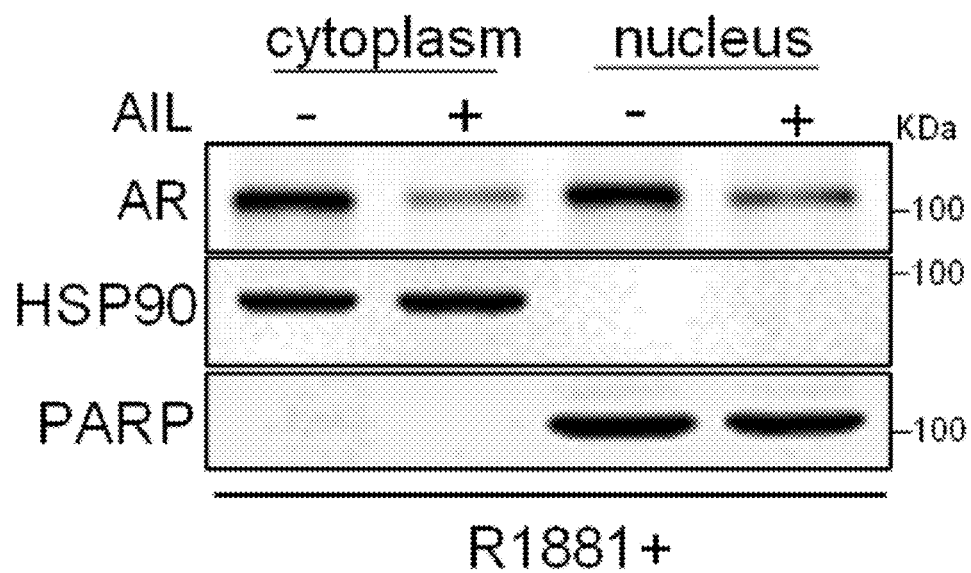
Figure 13E:
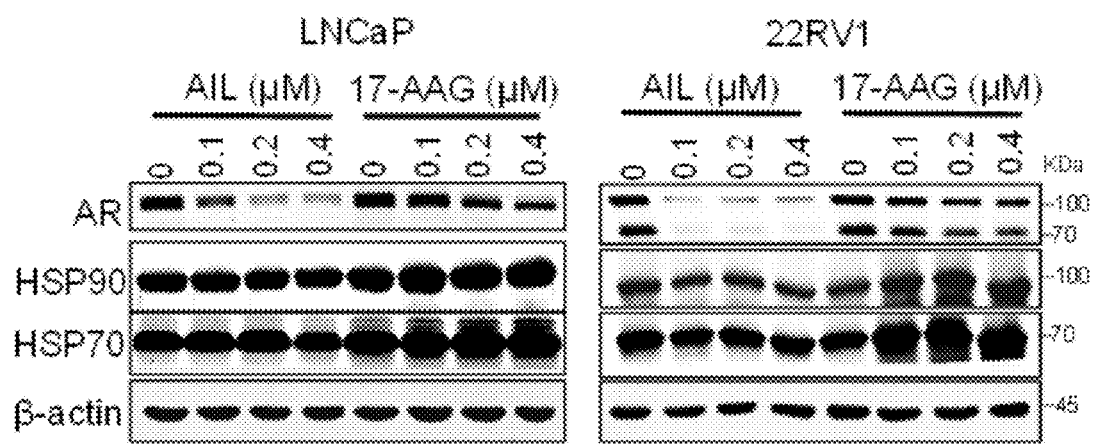
Figure 13F:
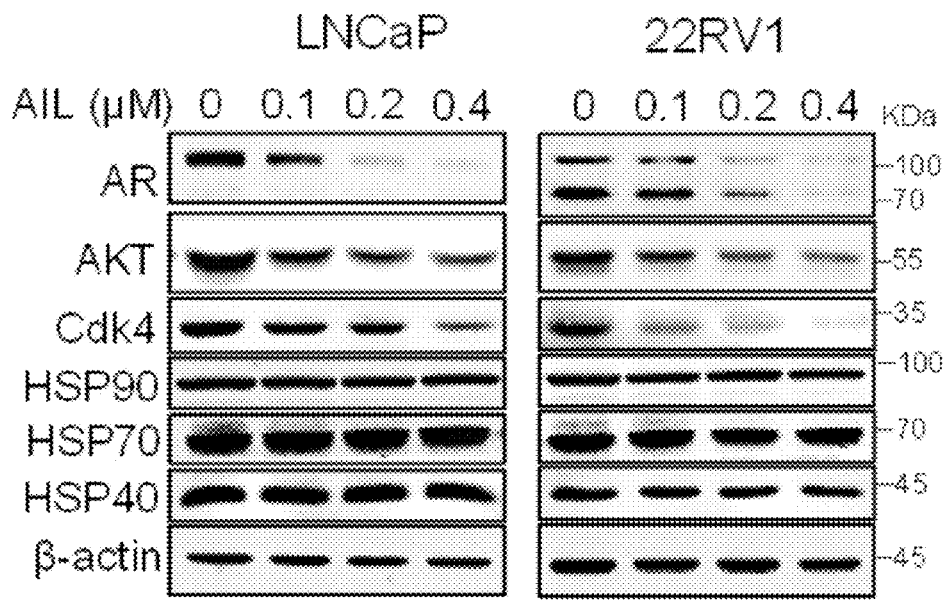
Figure 13G:
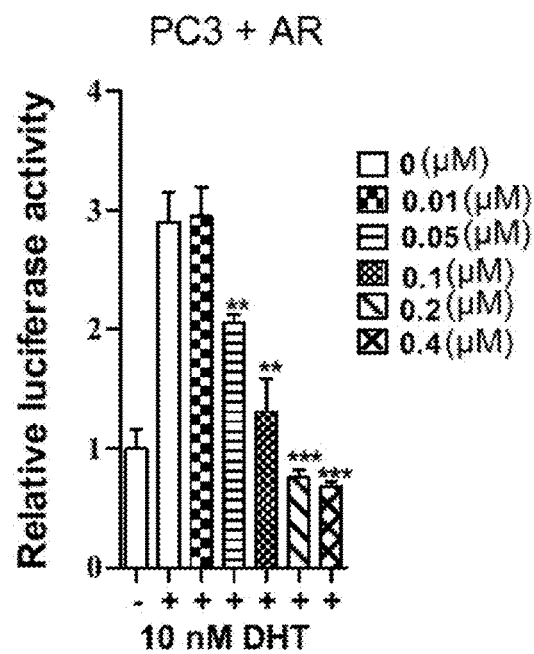

To further test the bioactivity of AIL and its derivatives (structure shown in Formula I-V), luciferase reporter assays were performed in several PCa cell lines including LNCaP, c4-2b, 22RV1 and AR-transfected PC3 cells. As shown in FIGS. 1A and 1B, AIL dose-dependently inhibited the DHT-induced transcriptional activities of AR and constitutively active truncated $AR_{1-651}$ at low concentrations (AR-FL $IC_{50}$=69 nM, 95% confidence interval=53-89 nM; $AR_{1-651}$ $IC_{50}$=309 nM, 95% confidence interval=236-687 nM in 22RV1 cells). The AIL-mediated repression of AR activity was also observed in PC3 cells co-transfected with the AR expression vector plasmid and reporters (FIG. 13G).

Figure 1C:
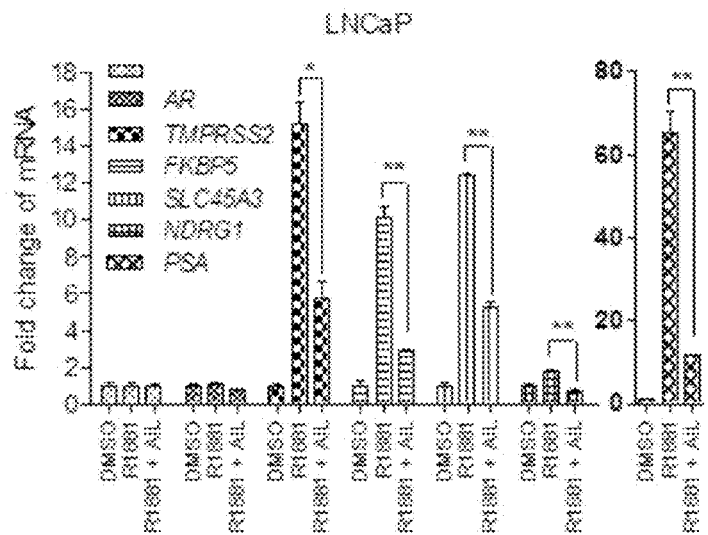
Figure 1D:
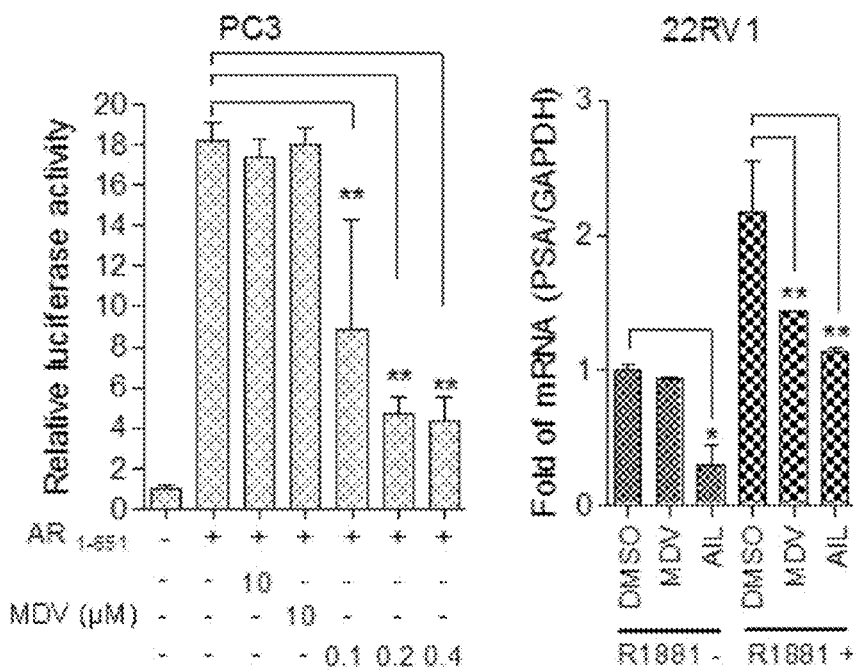

In order to examine whether AIL and its derivatives had an effect on AR-dependent endogenous gene expression, the levels of mRNA transcripts for numerous well-characterized AR-regulated genes were measured in LNCaP cells. As shown in FIG. 1C, AIL or its derivatives decreased the androgen-dependent induction of endogenous PSA, TMPRSS2, FKBP5, SLC45A3 and NDRG1 mRNA expression. Since AR-Vs lacking the LBD are resistant to AR antagonists, we next investigated whether AIL blocked its constitutive and androgen-independent AR activity. As shown in FIG. 1D, the constitutively active truncated $AR_{1-651}$ lacking the LBD was resistant to the AR antagonists bicalutamide (BIC) and MDV, but its transcriptional activity was also blocked by AIL in a dose-dependent manner (FIG. 1D, left panel). Similarly, in 22RV1 cells which naturally express AR-Vs, although MDV decreased the level of the AR target gene PSA in the presence of the synthetic androgen methyltrienolone (R1881), it had no effect in the absence of R1881. However, AIL down-regulated PSA not only in the presence but also in the absence of R1881 (FIG. 1D, right panel). Taken together, AIL inhibited the activity of both the androgen inducible AR-FL and the constitutively active truncated AR lacking the LBD.

TABLE 4

The pharmacokinetic parameters of AIL after oral administration or intravenous injection in rats (mean ± s.d.)

| pharmacokinetic parameters | p.o. (5 mg kg$^{-1}$) n = 6 | i.v. (1 mg kg$^{-1}$) n = 6 |
|---|---|---|
| $T_{1/2}$ (min) | 730.2 ± 155.9 | 113.3 ± 39.6 |
| $T_{max}$ (min) | 23.3 ± 31.8 | — |
| $C_{max}$ (ng mL$^{-1}$) | 87.0 ± 16.4 | — |
| $C_{max}$ (nM) | 231.1 ± 43.6 | |
| $C_0$ (ng mL$^{-1}$) | — | 1653.2 ± 98.6 |
| $C_0$ (nM) | | 4392.1 ± 261.9 |
| $AUC_{0-t}$ (min * ng mL$^{-1}$) | 67324.5 ± 7405.3 | 57874.3 ± 6871.1 |
| $AUC_{0-\infty}$ (min * ng mL$^{-1}$) | 79053.9 ± 14616.6 | 61517.4 ± 5986.2 |
| Bioavailability | 25.7% | — |

TABLE 5

Calculation of physicochemical properties of AIL

| Compound | M.W | NO. of HBD | NO. of HBA | TPSA | R.B | pKa | LogP |
|---|---|---|---|---|---|---|---|
| Ailanthone (AIL) | 376.4 | 3 | 7 | 113.29 | 0 | 12.2 ± 1.0 | −0.77 ± 0.62 |

M.W: molecular weight;
TPSA: Topological molecular polar surface area;
HBD: Hydrogen Bond Donors;
HBA: Hydrogen Bond Acceptors;
R.B: Rotatable Bonds

Example 2 AIL and its Derivatives Inhibit the Proliferation of PCa Cells

Figure 1E:
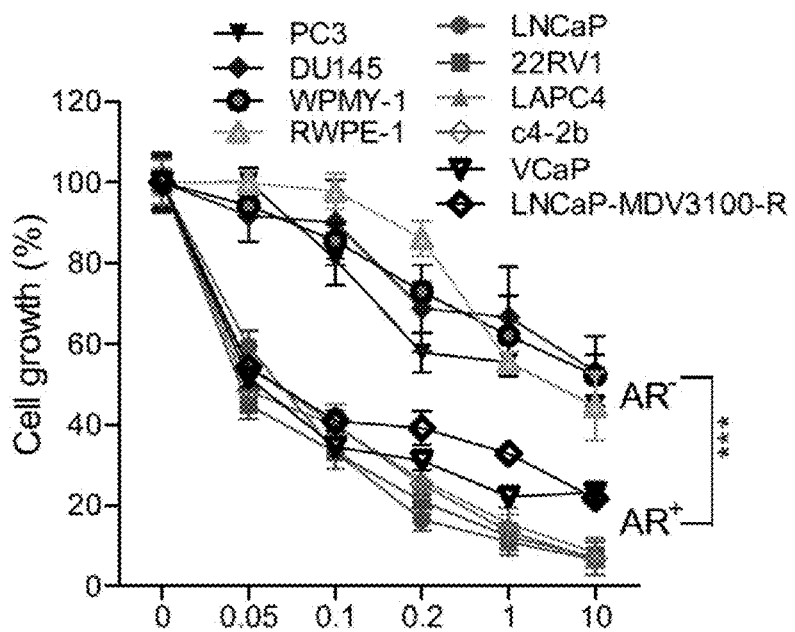
Figure 1F:
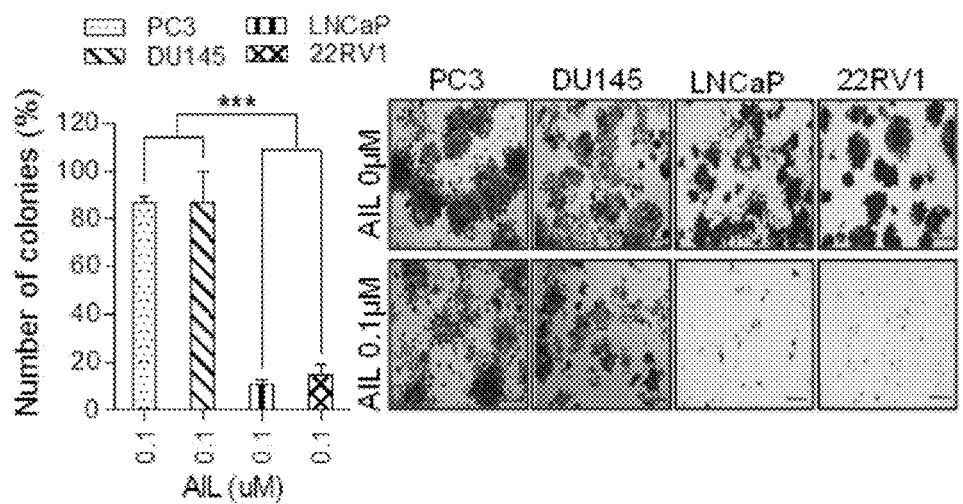
Figure 7A:
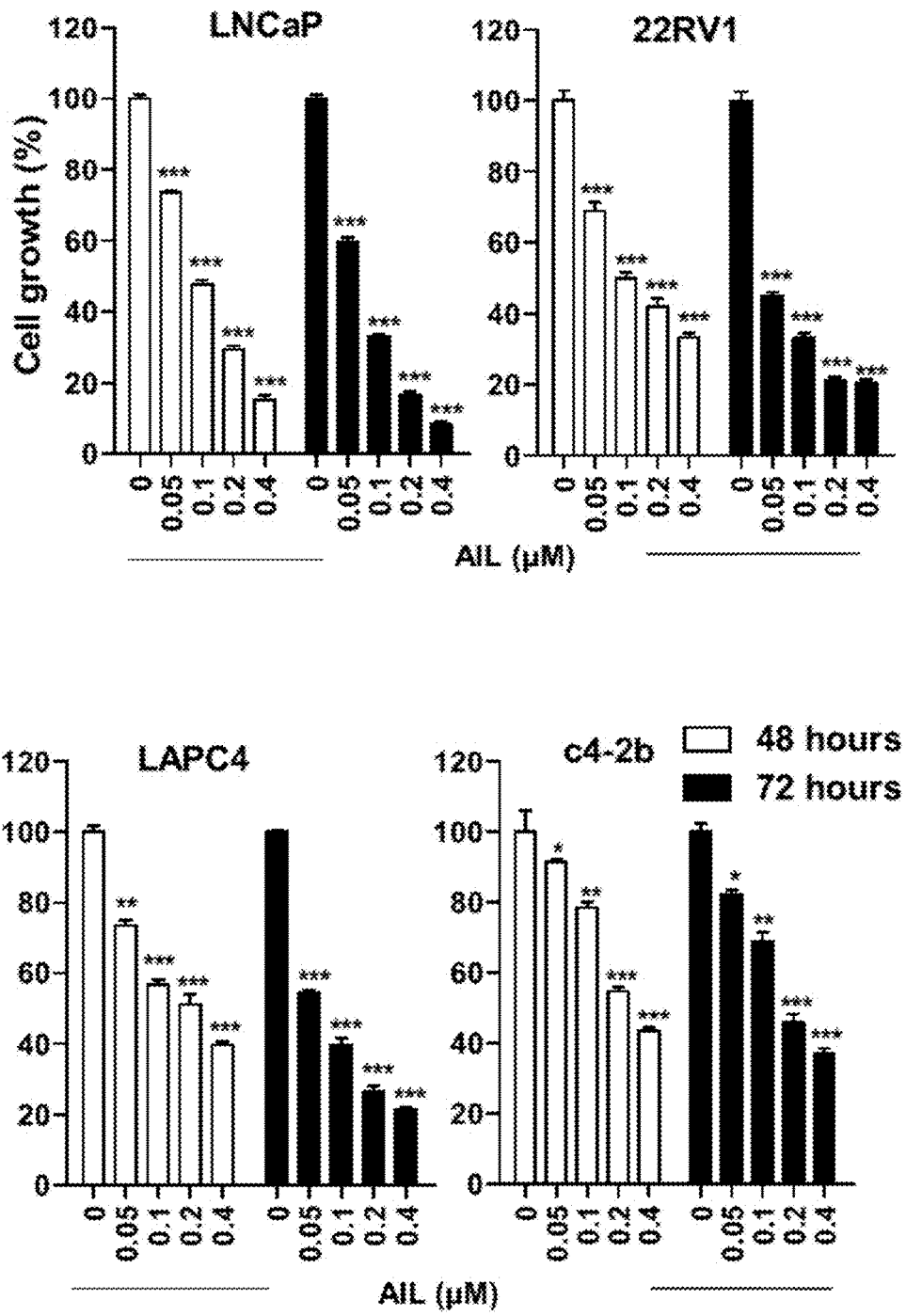
FIG. 7A-FIG. 7C. AR positive prostate cancer cells are more sensitive to AIL. (A) LNCaP, 22RV1, LAPC4, c4-2b cells were treated with indicated concentrations of AIL for 48 h or 72 h and cell proliferation was detected with the SRB assay (n=5). (B) Prostate normal cell lines RWPE-1 and WPMY-1, AR negative cell line PC3 and positive cell line LNCaP were treated with 0 or 0.1 μM AIL for 48 hours. The cells were imaged and a cropped region from each image is shown to enable a closer view. Scale bar, 50 μm. (C) AR negative cell line PC3 and positive cell line LNCaP prostate cancer cells were treated with different concentrations of AIL in Transwell chambers for 18 hours and the migrated cells were imaged and counted. Scale bar, 100 μm. Data was expressed as mean±s.d.; Student's t-tests were performed; *P<0.05, P<0.01, *P<0.001.
Figure 7B:
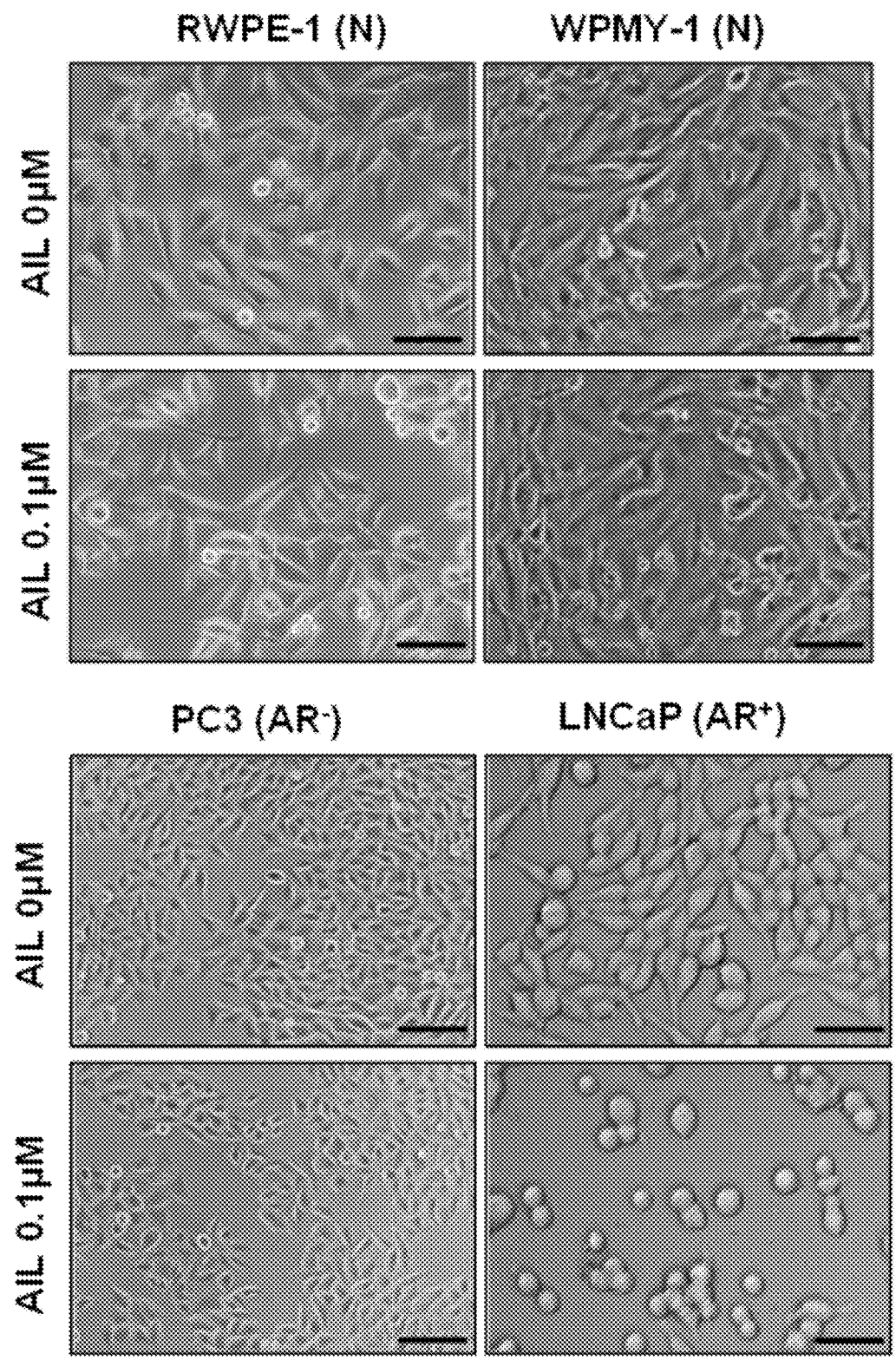
Figure 7C:
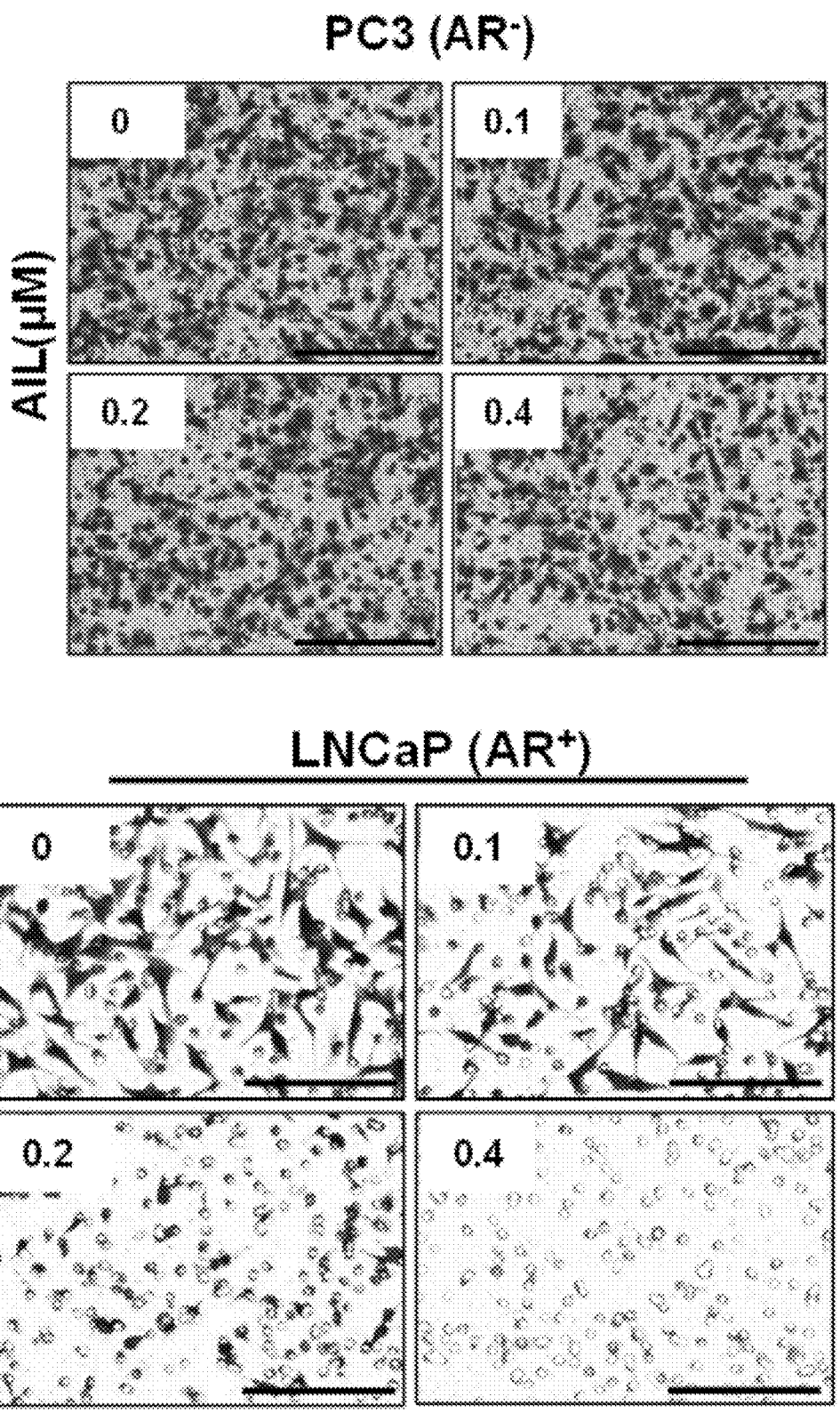
Figure 8:
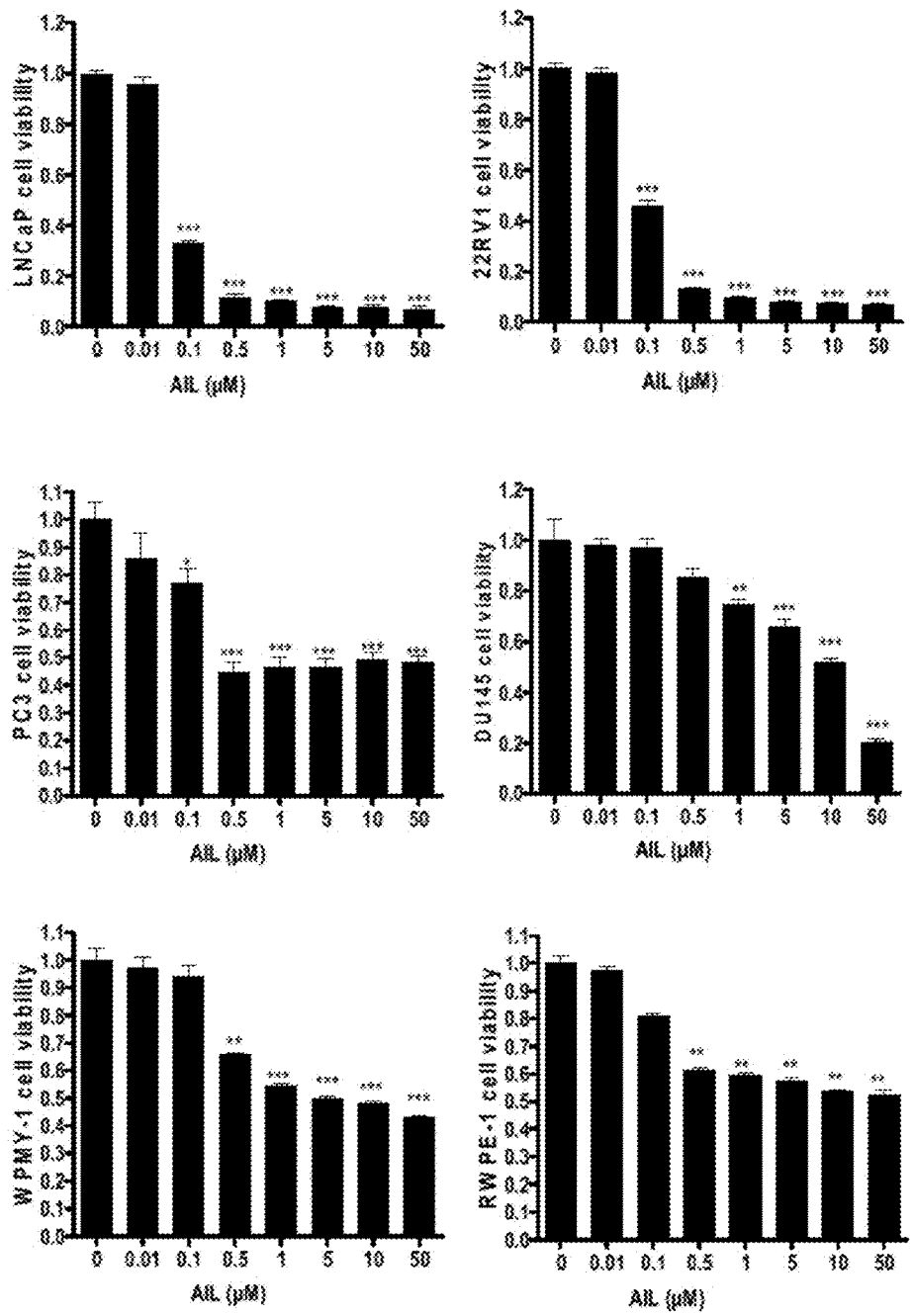
FIG. 8. Inhibitory effects of AIL on proliferation of prostate cancer cells and normal prostate cell lines. Prostate cancer cells (LNCaP, 22RV1, PC3, DU145), human prostate stromal cells WPMY-1 and the human normal prostate epithelial cell line RWPE-1 cells were treated with indicated concentrations of AIL for 48 h and the cell proliferation was detected with the SRB assay (n=5). Data was expressed as mean±s.d.; Student's t-tests were performed; *P<0.05, P<0.01, *P<0.001.
Figure 14A:
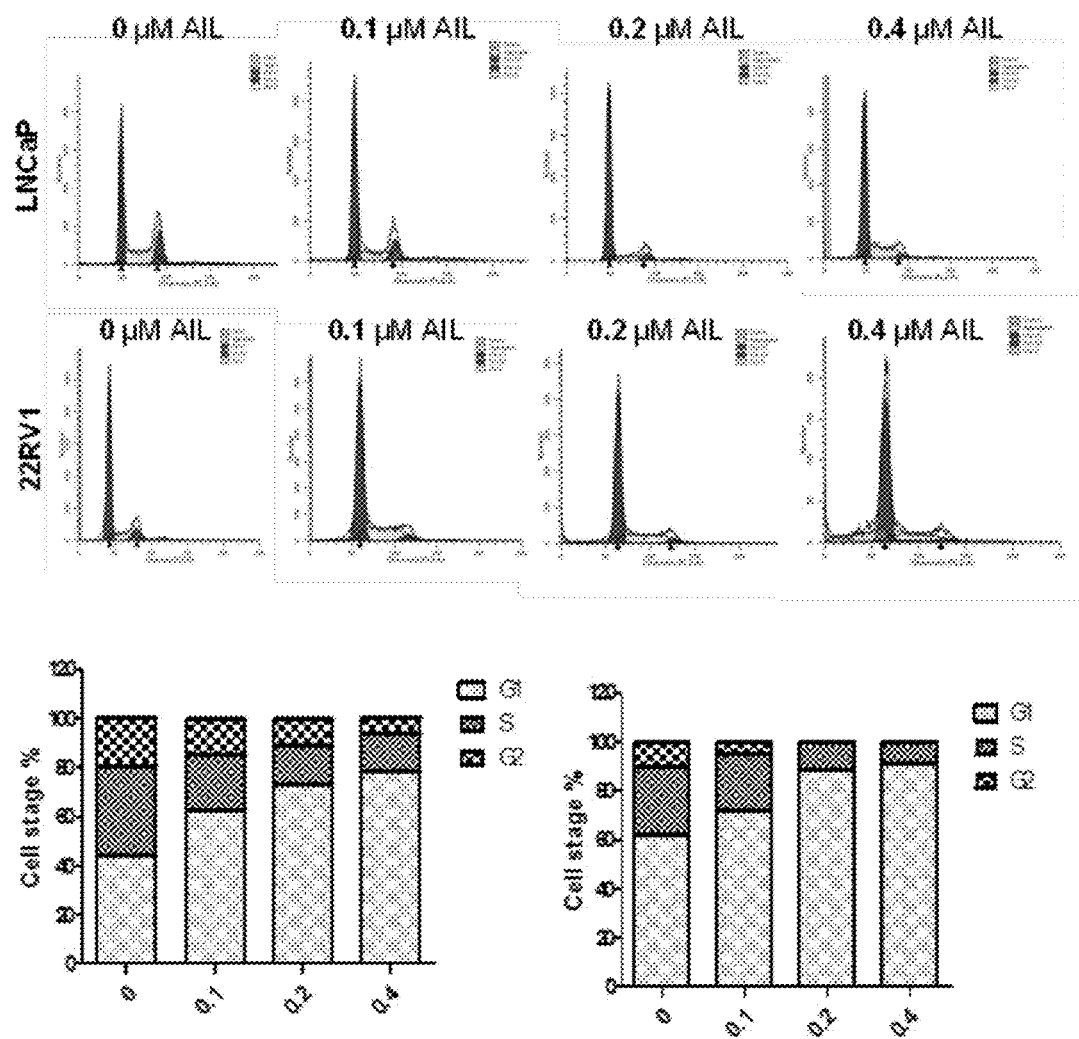
FIG. 14A-FIG. 14B. AIL induced G1-phase arrest instead of apoptosis. (A) LNCaP and 22RV1 cells were treated with the indicated concentrations of AIL for 24 hours. Then cells were fixed with 70% ethanol and stained with PI and sent for cell cycle analysis with flow cytometry. The percentage of each phase is shown in the right panel. (B) LNCaP and 22RV1 cells were treated with the indicated concentrations of AIL for 24 hours. Then cells were stained with PI and Annexin V-FITC and then subjected to flow cytometry analysis of cell apoptosis.
Figure 14B:
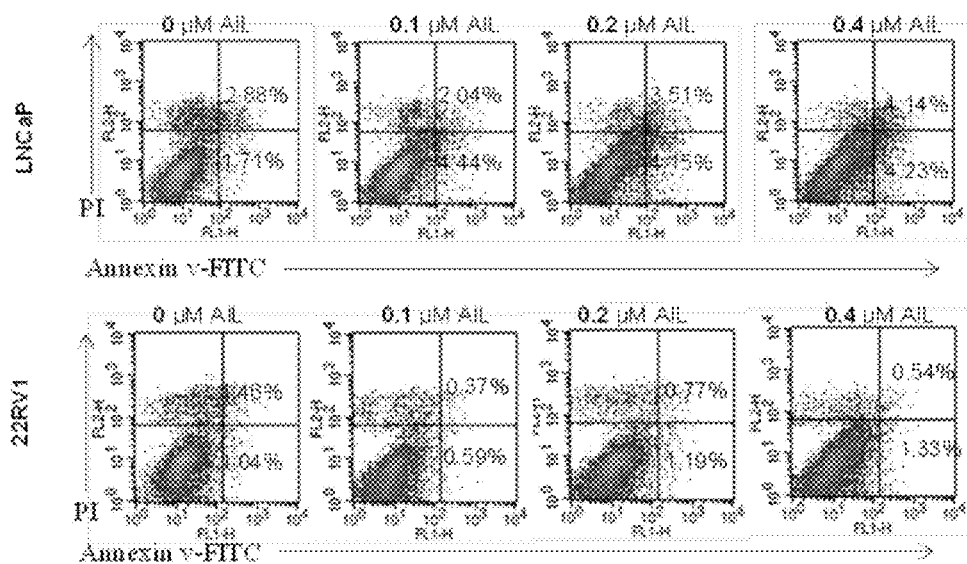

We examined whether AIL and its derivatives affected the proliferation of AR positive PCa cells. Using the Sulforhodamine B colorimetric (SRB) assay, we confirmed that AIL and its derivatives potently inhibited the growth of several PCa cell lines including LNCaP, c4-2b, 22RV1 and LAPC4 (FIG. 7A). In addition, AIL and its derivatives induced G1-phase arrest of instead of apoptosis (FIGS. 14A and 14B). Interestingly, AIL and its derivatives more potently inhibited the growth of AR positive prostate cancer cells than either AR negative tumor cell lines or normal prostate cell lines (FIG. 1E, FIG. 7B and FIG. 8). In the colony formation experiments, AR positive cells were also more sensitive to AIL and its derivatives (FIG. 1F). Moreover, in the transwell chamber migration assay, AIL and its derivatives suppressed AR-positive LNCaP cell migration more effectively than that of AR-negative PC3 cells (FIG. 7C).

Figure 1G:
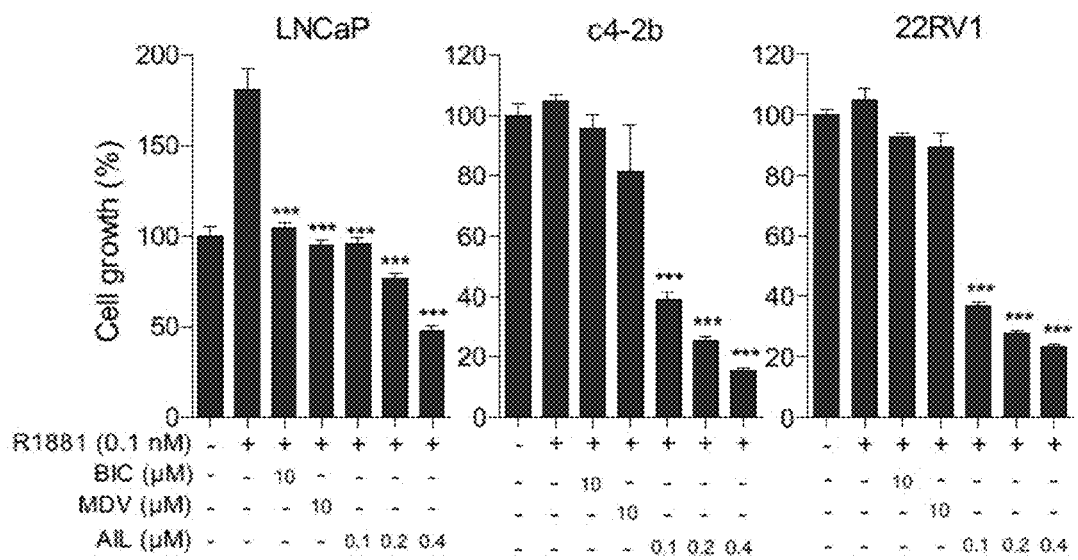
Figure 1H:
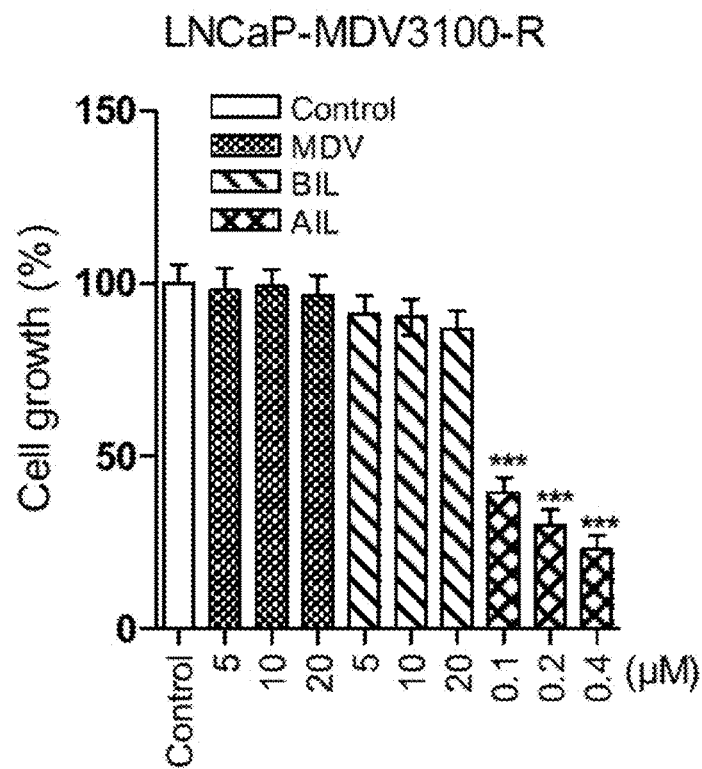
Figure 18A:
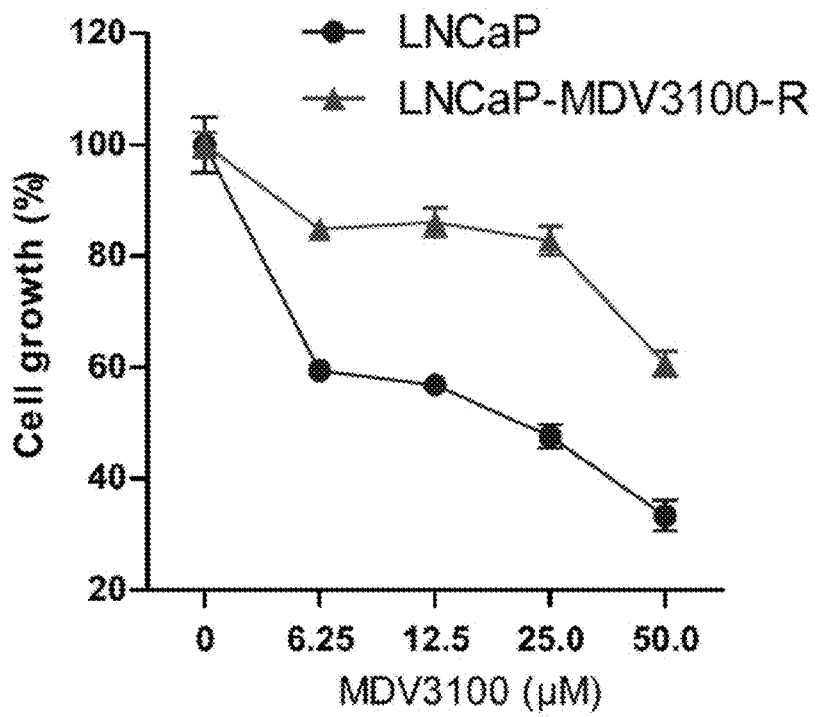
FIG. 18A-FIG. 18C. Characterization of LNCaP-MDV3100-R. (A) LNCaP and LNCaP-MDV3100-R (resistant to MDV3100) were treated with indicated concentrations of MDV3100 for 72 hours and the cell proliferation was detected with the SRB assay (n=5). The half maximal inhibitory concentration (IC50) was calculated using GraphPad Prism 5.0 (GraphPad, San Diego, Calif.). (B) LNCaP-MDV3100-R cell line expresses a similar AR level as LNCaP. LNCaP and LNCaP-MDV3100-R cells were lysed and AR protein levels were measured by Western blot analysis. β-actin serves as internal control. (C) LNCaP-MDV3100-R cells still respond to androgen. LNCaP-MDV3100-R cells were cultured in 5% c-FBS for 48 hours and treated with or without 10 nM DHT for 12 hours. DMSO was added as the control. Total RNA was extracted and quantitative-PCR was performed with the PSA and GAPDH specific primer. The PSA mRNA level was normalized to GAPDH. Data was expressed as mean±s.d. of three independent assays; Student's t-tests were performed; **P<0.01.
Figure 18B:
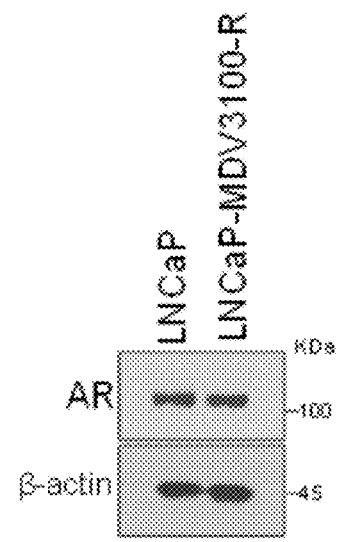
Figure 18C:
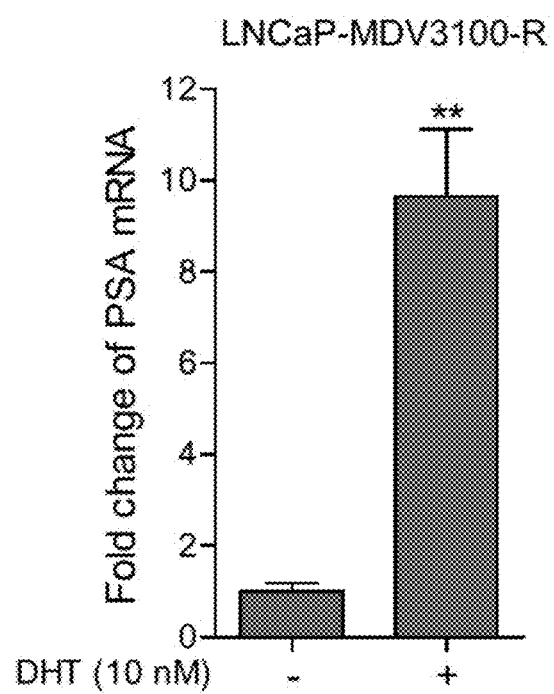

To examine whether AIL and its derivatives could overcome the resistance to androgen antagonist therapy, LNCaP, c4-2b, and 22RV1 cells were tested using the SRB assay (FIG. 1G). Although C4-2b and 22Rv1 cells may be androgen-insensitive, these assays were performed in the presence of R1881. In androgen sensitive LNCaP cells, the well-known AR antagonists BIC and MDV effectively blocked cell growth as well as AIL and its derivatives (FIG. 1G). However, in the androgen-insensitive c4-2b line and the CRPC cell line 22RV1, 10 µM BIC and 10 µM MDV could not significantly inhibit cell growth, but 0.1 µM AIL or its derivatives remarkably inhibited growth (FIG. 1G). Furthermore, LNCaP-MDV3100-R cells (a MDV3100-resistant LNCaP cell subline which was chronically cultured in the presence of MDV and is characterized in FIG. 18) were totally resistant to BIC and MDV at a high concentration (20 µM), but 0.1 µM AIL or its derivatives treatment still significantly induced cell growth arrest (FIG. 1H). Collectively, AIL or its derivatives inhibited both androgen-dependent and androgen-independent PCa cell growth and overcame resistance to AR antagonist therapy.

Figure 9:
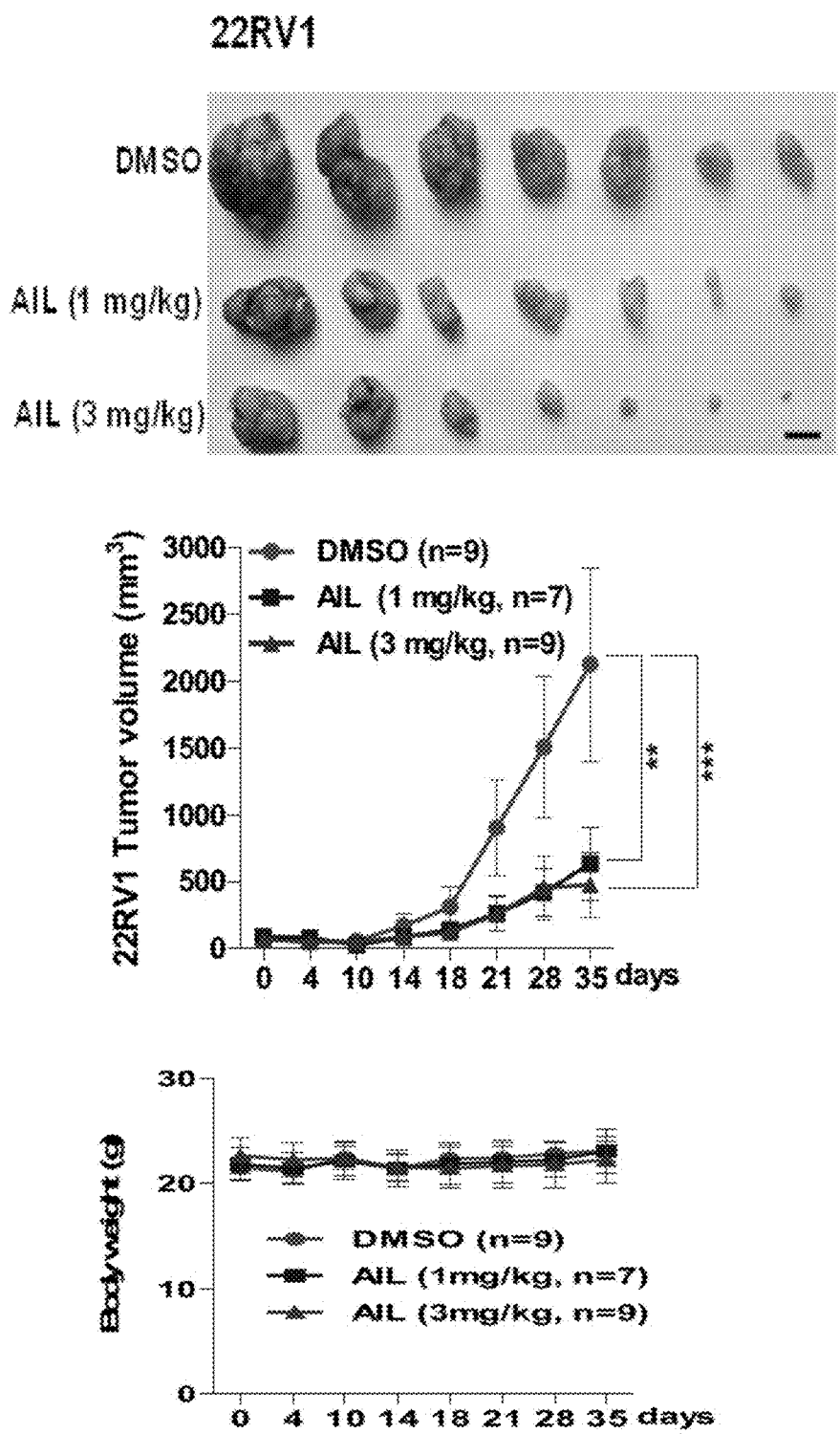
FIG. 9. Cytoreduction of 22RV1 xenografts in vivo by AIL. $3\times10^6$ 22RV1 cells with 0.1 ml PBS were injected into the right flank of BALB/c-nude mice. After the volume of tumor nodules was about 100 $mm^3$, the mice were randomly assigned to the indicated groups and i.p. injected daily with DMSO (control), 1 mg/kg AIL and 3 mg/kg AIL, respectively. Tumor volumes and the mouse body weights were measured twice a week. The mice were sacrificed after 35 days and the tumors from each group of mice were excised and images were taken. Scale bar, 1 cm. Data represent the mean±s.d. P<0.01, *P<0.001 by one-way ANOVA followed by Bonferroni multiple comparison test.
Figure 11A:
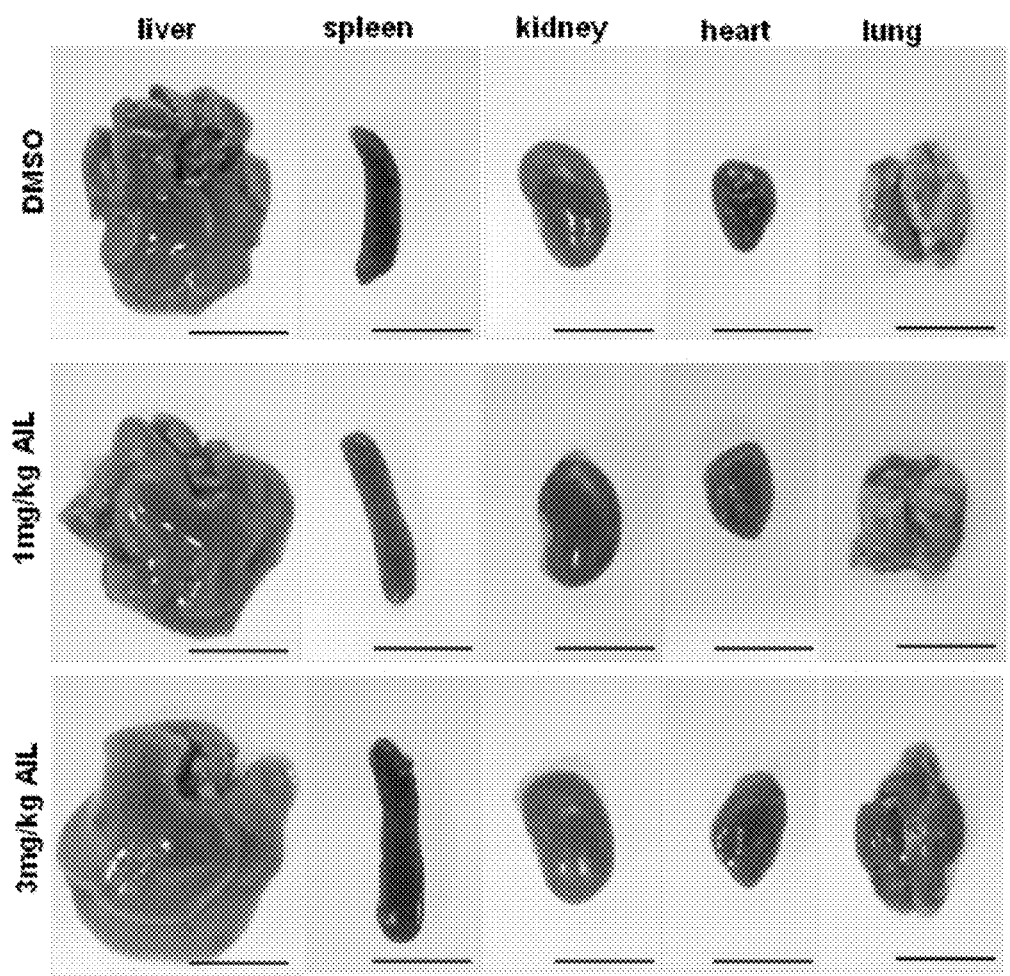
FIG. 11A-FIG. 11C. I.p. delivery of AIL did not cause toxicity. (A,B) $3\times10^6$ 22RV1 cells were injected with 0.1 ml PBS into the right flank of a nude mouse. After tumor nodules grew to a volume about 100 $mm^3$, the mice were randomly assigned to three groups and respectively i.p injected with DMSO, 1 or 3 mg/kg/day AIL. After 35 days, mice were sacrificed and organs were removed. Photographs (A) and HE-staining (B) of the representative organs from mice administered daily with DMSO, 1 mg/kg AIL or 3 mg/kg AIL were illustrated. Tissues shown in FIG. 9 were from the same animals. Scale bar, 1 cm in panel A and 100 μm in panel B. (C) $3\times10^6$ Vcap cells were injected with 0.1 ml matrigel into the right flank of a nude mouse. After tumor nodules grew to a volume about 100 $mm^3$, the mice were randomly assigned to three groups and respectively i.p injected with DMSO, 10 mg/kg MDV or 2 mg/kg AIL. After 35 days, mice were sacrificed and prostate and seminal vesicle tissues were excised. Photographs of the representative organs from mice administered with DMSO, 10 mg/kg MDV or 2 mg/kg AIL were illustrated. The weight of seminal vesicles was measured (Right panel). Tissues shown in FIG. 2C were from the same animals. Scale bar, 1 cm.
Figure 11B:
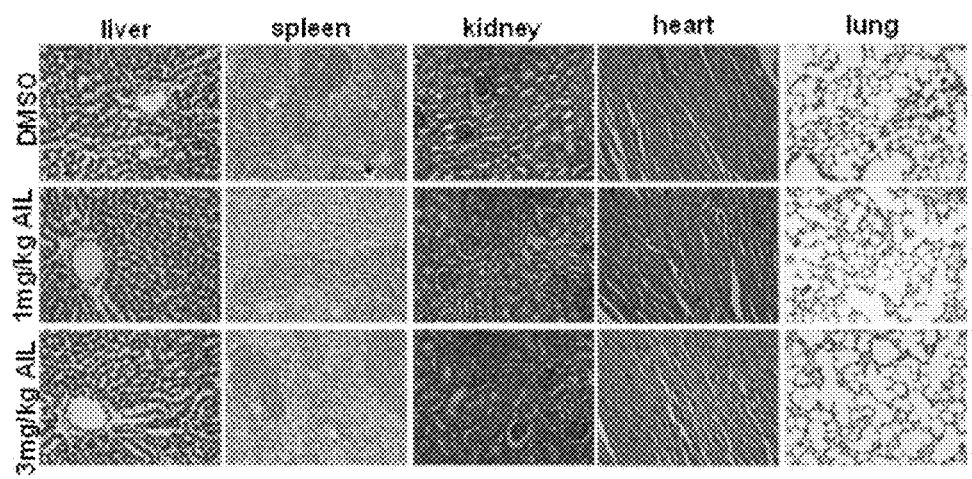
Figure 11C:
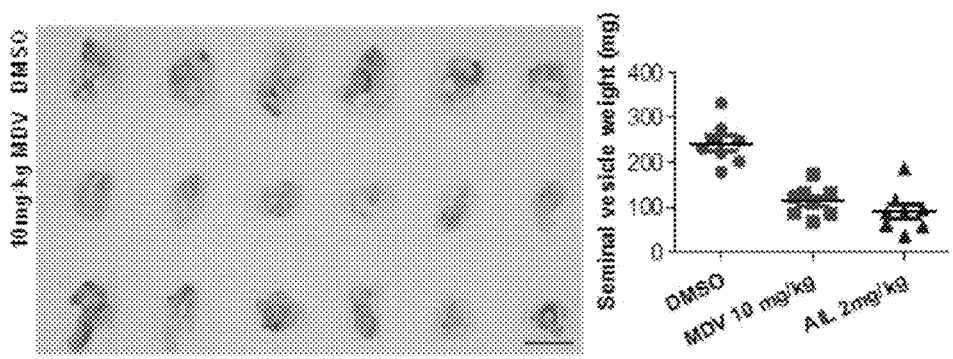

Example 3 AIL and its Derivatives Blocks Tumor Growth and Metastasis of CRPC We evaluated the efficacy of AIL or its derivatives in vivo by treating 22RV1 xenografts in male BALB/c nude mice with AIL for 35 days. Administration of 1 and 3 mgkg$^{-1}$ per day AIL and its derivatives significantly inhibited the increase of tumor volume in 22RV1 xenografts (FIG. 9). AIL and its derivatives did not significantly affect the body weight of mice and did not show apparent toxicity as determined by pathological review of sections of lungs, heart, liver, spleen and kidneys harvested from mice receiving AIL (FIG. 11A, B). Additionally, treatment with AIL decreased the weight of seminal vesicle of the mice (FIG. 11C), indicating that AIL blocked AR signaling in the mice in vivo. Therefore, we selected the dose of 2 mgkg$^{-1}$ per day AIL for further experiments in animals.

Figure 2A:
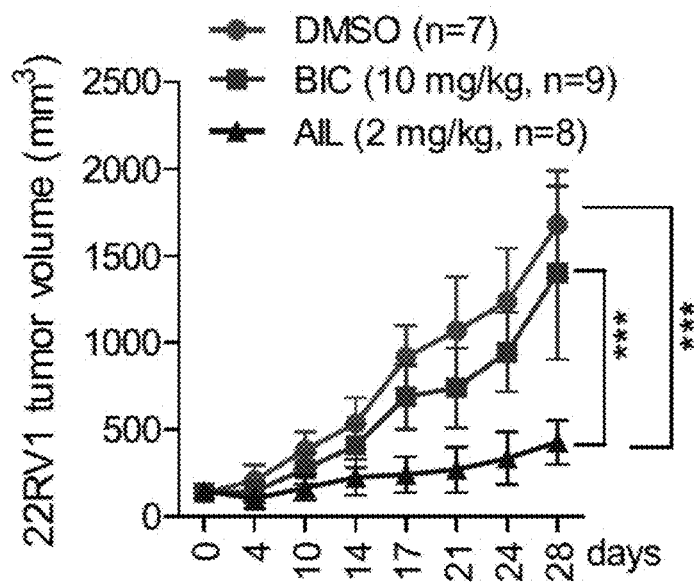
FIG. 2A-FIG. 2F. Therapeutic effects of AIL on castration-resistant xenografts. (A-C) 22RV1 (A), LNCaP (B) and VCaP (C) cells suspended in 0.1 ml PBS (22RV1) or matrigel (LNCaP, VCaP) were injected into the right flank of BALB/c-nude mice. Androgen containing blocks were subcutaneously inserted into each mouse in the LNCaP and VCaP xenograft models. After the volume of tumor nodules reached about 100 mm³, the mice were randomly assigned to the indicated groups and respectively i.p. injected with vehicle control, AIL, BIC or MDV as indicated. The control group was injected with DMSO. Tumor volume and the mouse body weight were measured twice per week. (D) Male BALB/c-nude mice were anesthetized, and the dorso-lateral prostate was injected with 22RV1-luc cells in matrigel. After a week, mice were castrated and treated i.p. with DMSO, 10 mgkg$^{-1}$ MDV or 2 mgkg$^{-1}$ AIL once per day. Tumors were imaged every week to determine local tumor growth and evidence of tumor cell dissemination. Representative images of 3 mice per group were illustrated (n=5). (E) After 28 days, mice were sacrificed and local tumors and viscera of the mice were imaged to determine tumor growth and evidence of tumor cell dissemination. Representative images of the dishes are shown, and the number of mice which had metastatic tumors was counted (n=5). (F) The mouse kidneys from the same experiment as panel D were histopathologically evaluated. The number of mice which had kidney injury was counted (n=5). Scale bar, the black scale bar is 0.5 cm (left) and the white scale bar is 100 μm (right). Data represent the mean±s.d. *P<0.05, P<0.01, *P<0.001 by one-way ANOVA followed by Bonferroni multiple comparison test.
Figure 2B:
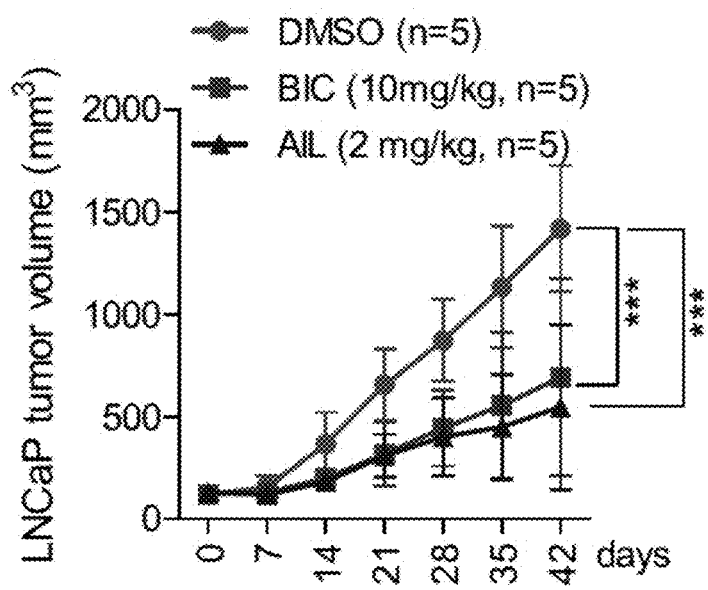
Figure 2C:
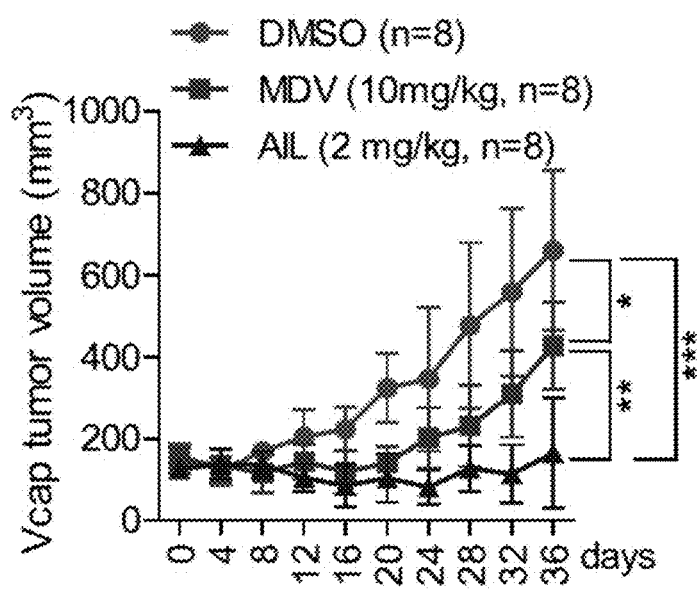
Figure 10A:
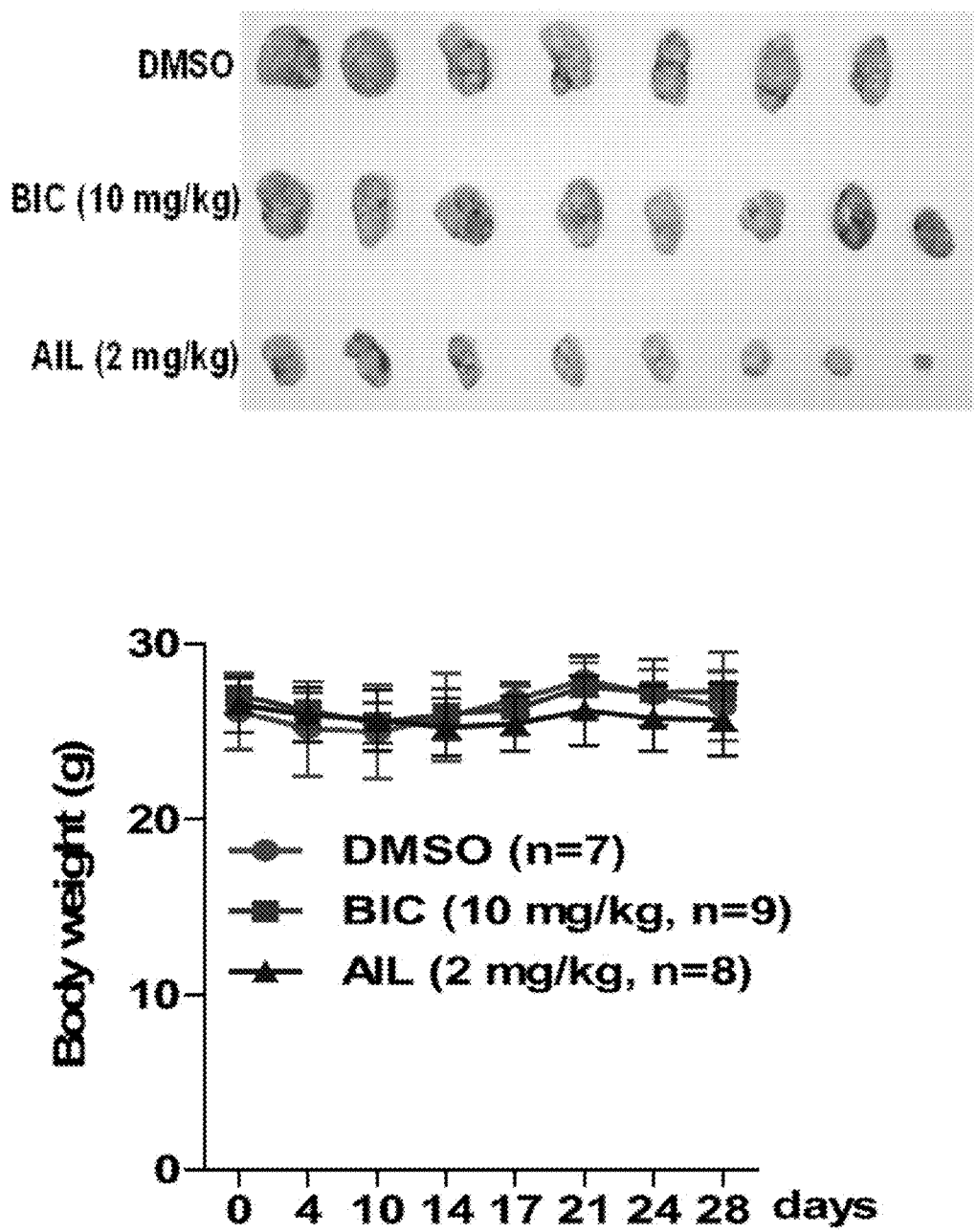
FIG. 10A-FIG. 10C. Comparing the anti-tumor efficiency of AIL with AR antagonists in different xenograft models. (A-C) 22RV1 (A), LNCaP (B) and Vcap (C) cells were injected with 0.1 ml PBS (22RV1) or Matrigel (LNCaP, Vcap) into the right flank of BALB/c-nude. After the volume of tumor nodules reached about 100 $mm^3$, the mice were randomly assigned to the indicated groups and i.p. injected daily with DMSO (control), AIL, BIC, or MDV as indicated. Tumor volume and the mouse body weight were measured once a week. The mice were sacrificed after 28 days (22RV1), 49 days (LNCaP) or 32 days (Vcap) and the tumors from each group of mice were harvested and images were taken. Scale bar, 1 cm. Data represent the mean±s.d.
Figure 10B:
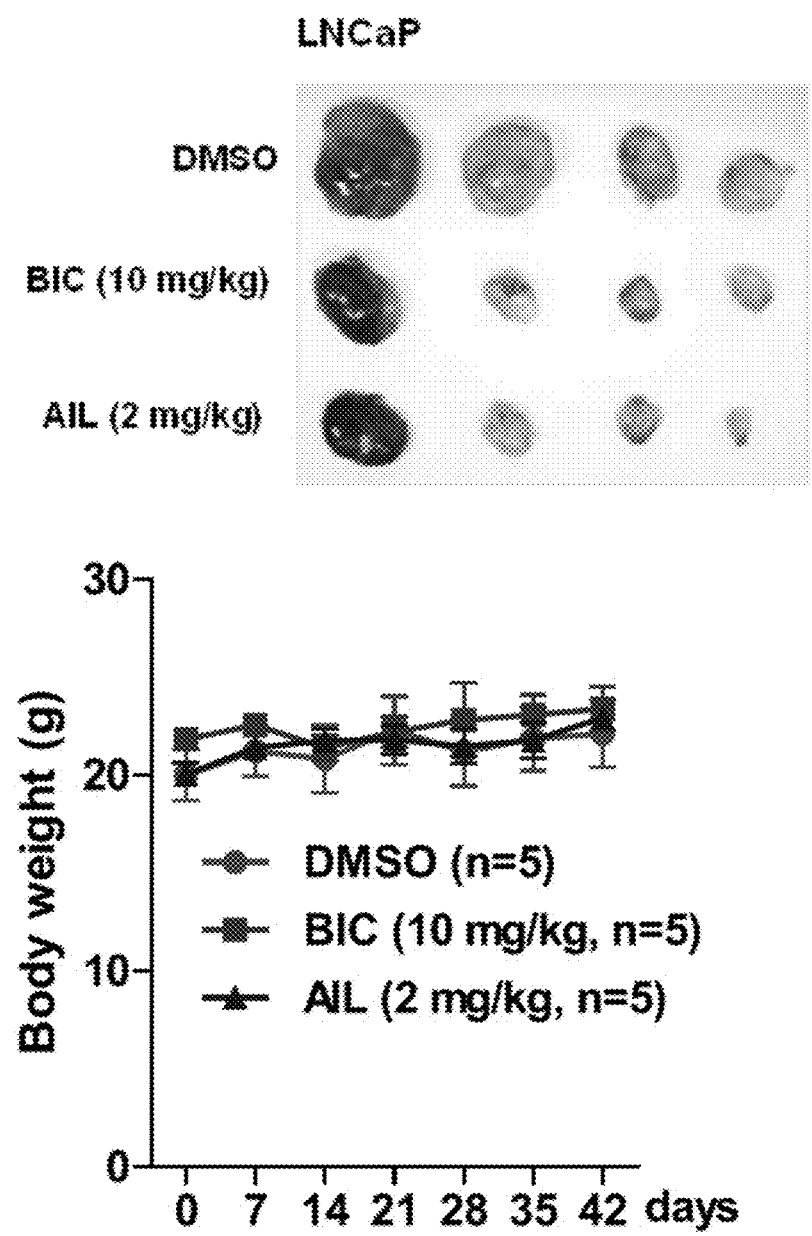
Figure 10C:
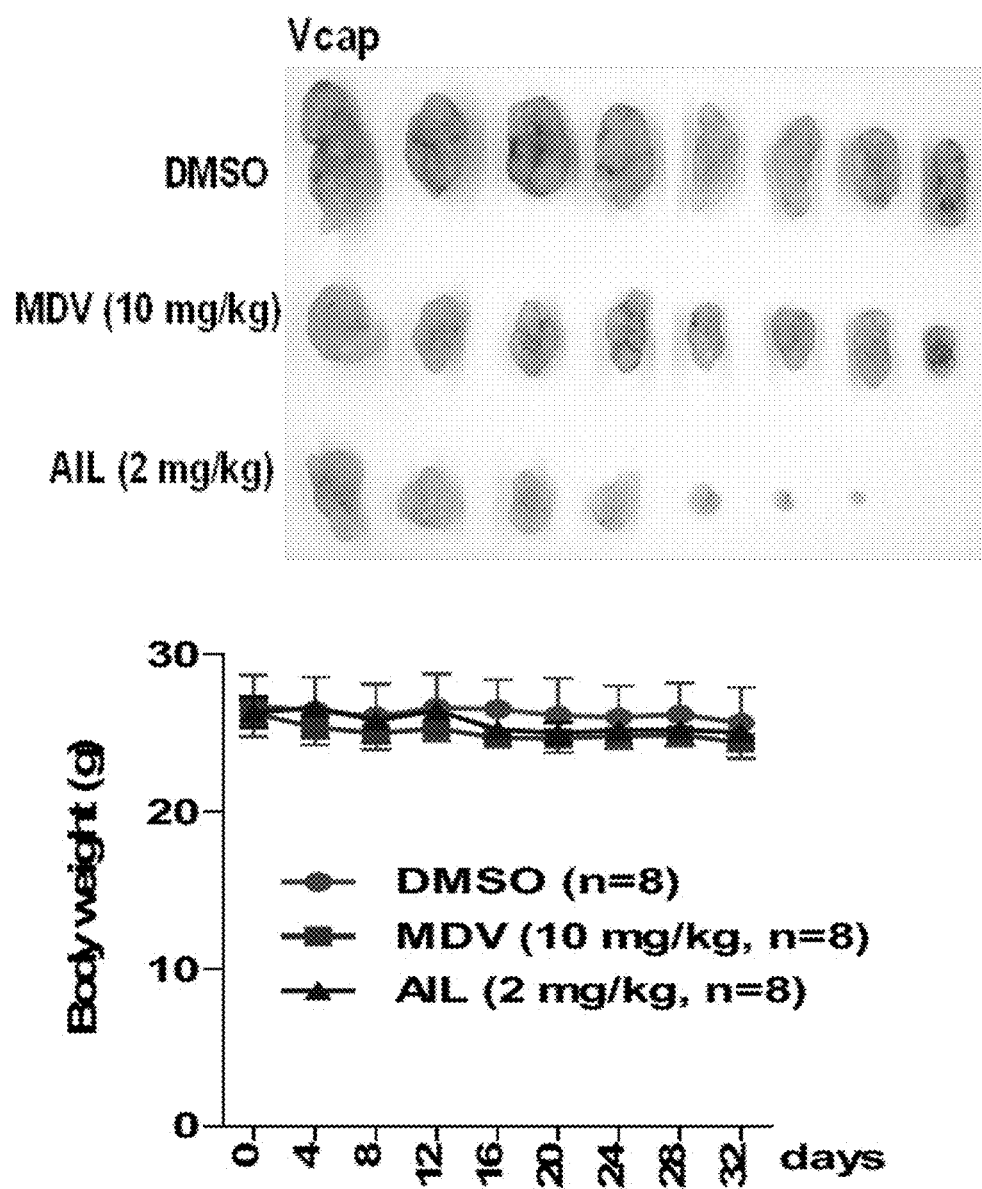

We also compared the efficiency of AIL with the well-known AR-antagonist BIC in both LNCaP and 22RV1 xenografts. For androgen-sensitive LNCaP cells, treatment with either 10 mg kg$^{-1}$ per day BIC or 2 mg kg$^{-1}$ per day AIL significantly reduced the tumor volume (FIG. 2B and FIG. 10B). In contrast, the CRPC 22RV1 xenografts were resistant to BIC administration, but AIL strongly inhibited tumor growth (FIG. 2A and FIG. 10A). Furthermore, we compared the efficiency of AIL with the next generation AR-antagonist MDV in another cell line, VCaP, which expresses AR-Vs but is still sensitive to androgen. As shown in FIG. 2C and FIG. 10C, VCaP xenografts were more sensitive to AIL compared with MDV3100, although VCaP xenografts still responded to MDV3100.

Figure 2D:
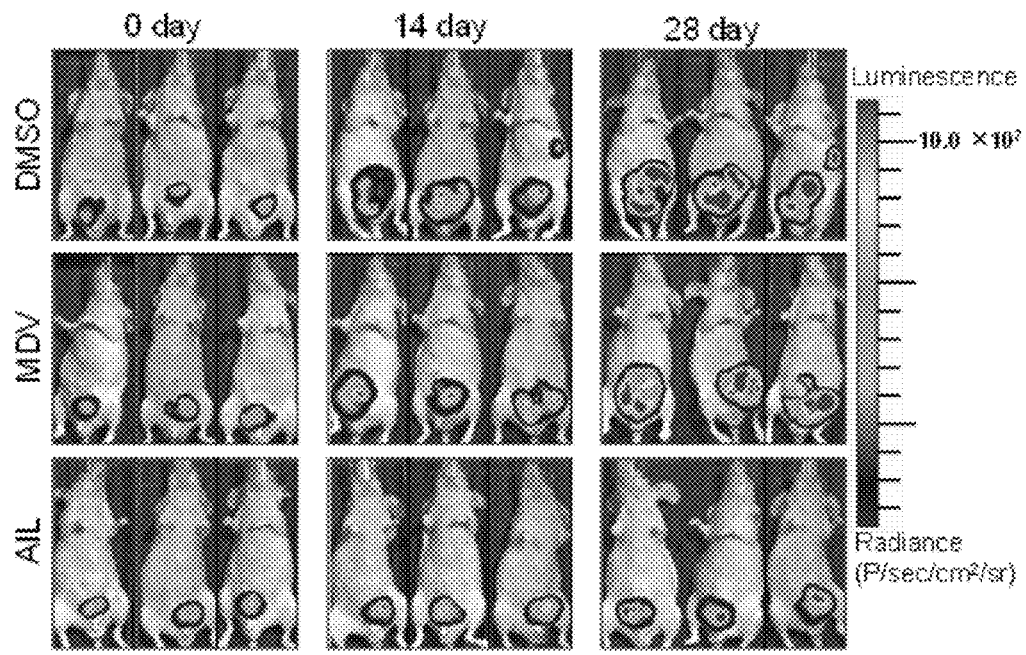
Figure 2E:
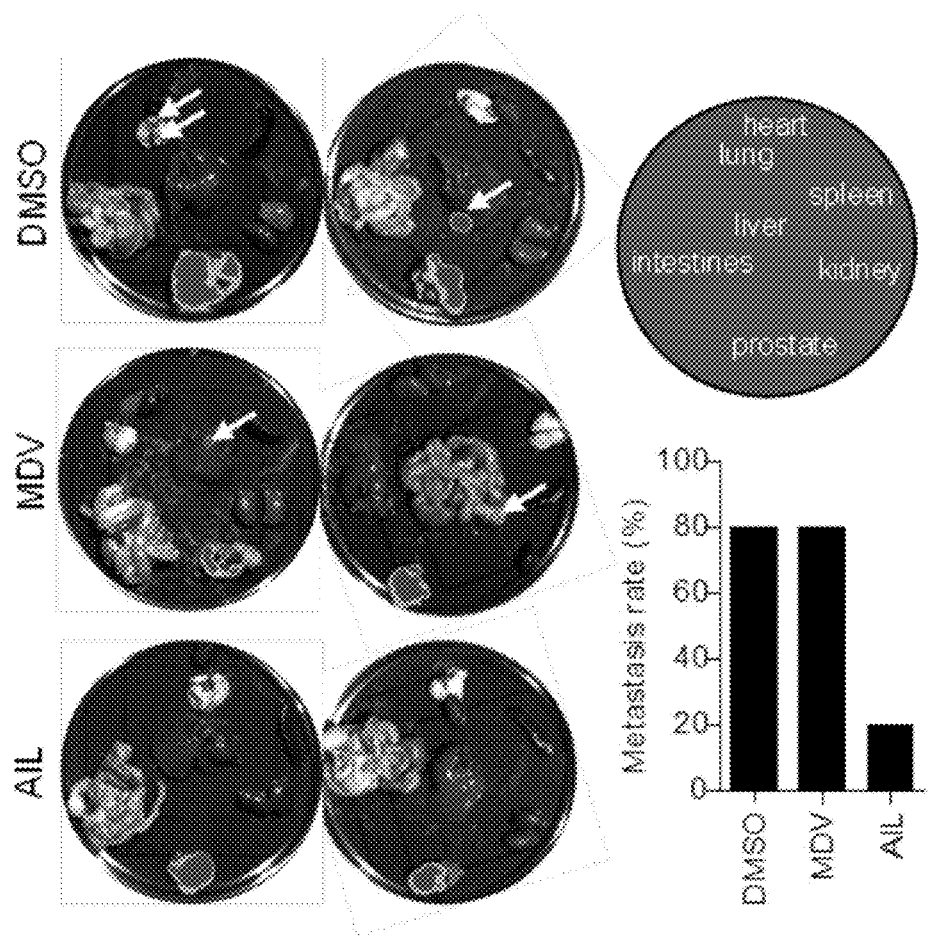
Figure 2F:
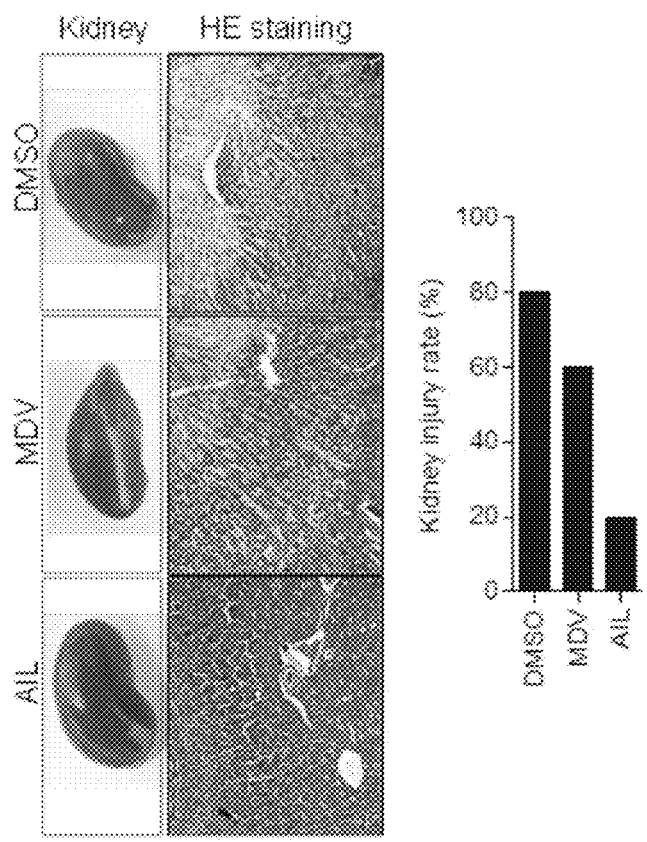
Figure 12A:
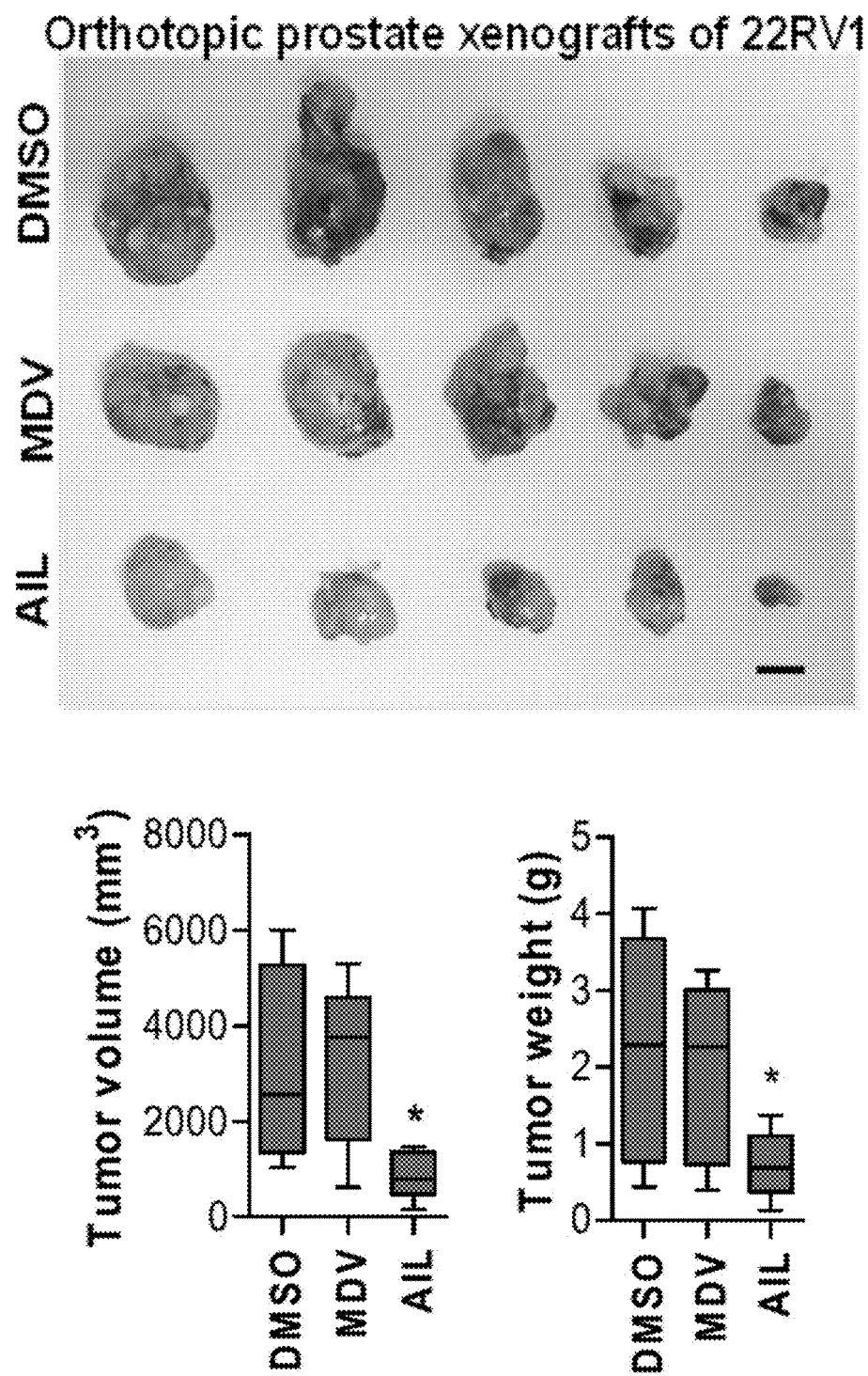
FIG. 12A-FIG. 12B. AIL inhibited tumor growth and metastasis in a CRPC animal model. (A,B) The dorsolateral prostate of male BALB/c-nude mice was injected with $1\times10^6$ 22RV1-luc cells in 30 μl matrigel. After a week, mice were castrated and injected i.p. with DMSO, 10 mg/kg MDV or 2 mg/kg AIL once a day. After 28 days, mice were sacrificed and the local tumors were removed and volumes and weight of the tumors were measured (A). The local tumors and viscera of the mice were imaged for counting metastatic tumors (B). Scale bar, 1 cm. Data was expressed as mean±s.d.; Student's t-tests were performed; *P<0.05.
Figure 12B:
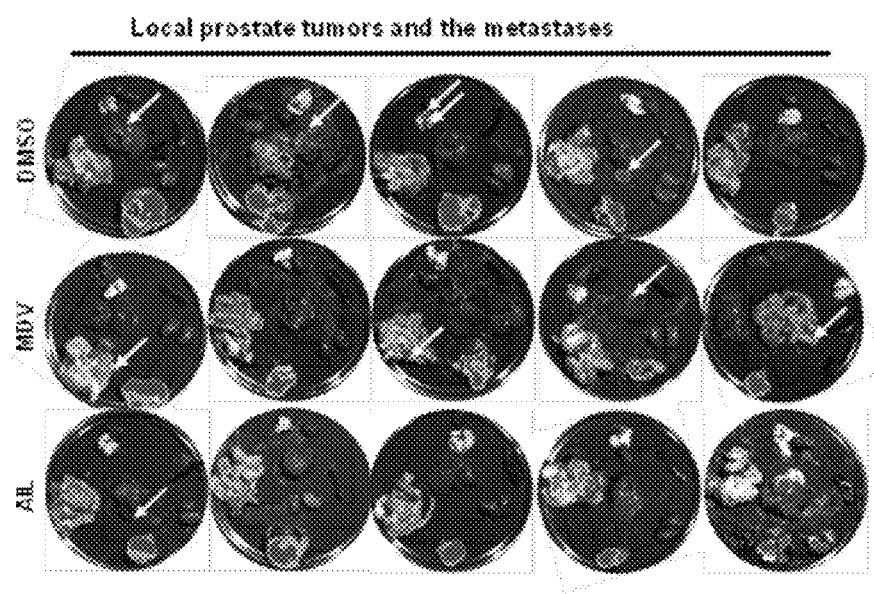

To more closely mimic human disease, we further evaluated whether AIL regressed CRPC in vivo. Castrated mice bearing 22RV1-luc orthotopic xenografts were treated with AIL. As shown in FIG. 2D and FIG. 12A, AIL suppressed the 22RV1 orthotopic xenografts in castrated mice, whereas these CRPC xenografts were resistant to MDV. AIL administration reduced the tumor volume by 82% (95% confidence interval=70-95%), whereas MDV treatment reduced the tumor volume by only 15% (95% confidence interval=0-36%). In addition, AIL inhibited tumor metastasis and reduced kidney injury in this CRPC model. 80% of control mice but only 20% of AIL-treated mice had obvious metastasis (FIG. 2E and FIG. 12B) and kidney injury (FIG. 2F). In summary, AIL not only inhibited the tumor growth and metastasis of MDV-resistant 22RV1 cells, but also reduced kidney injury and metastases in orthotopic xenografts.

Example 4 AIL Clown-Regulates AR Protein Level In Vitro and In Vivo

Figure 3A:
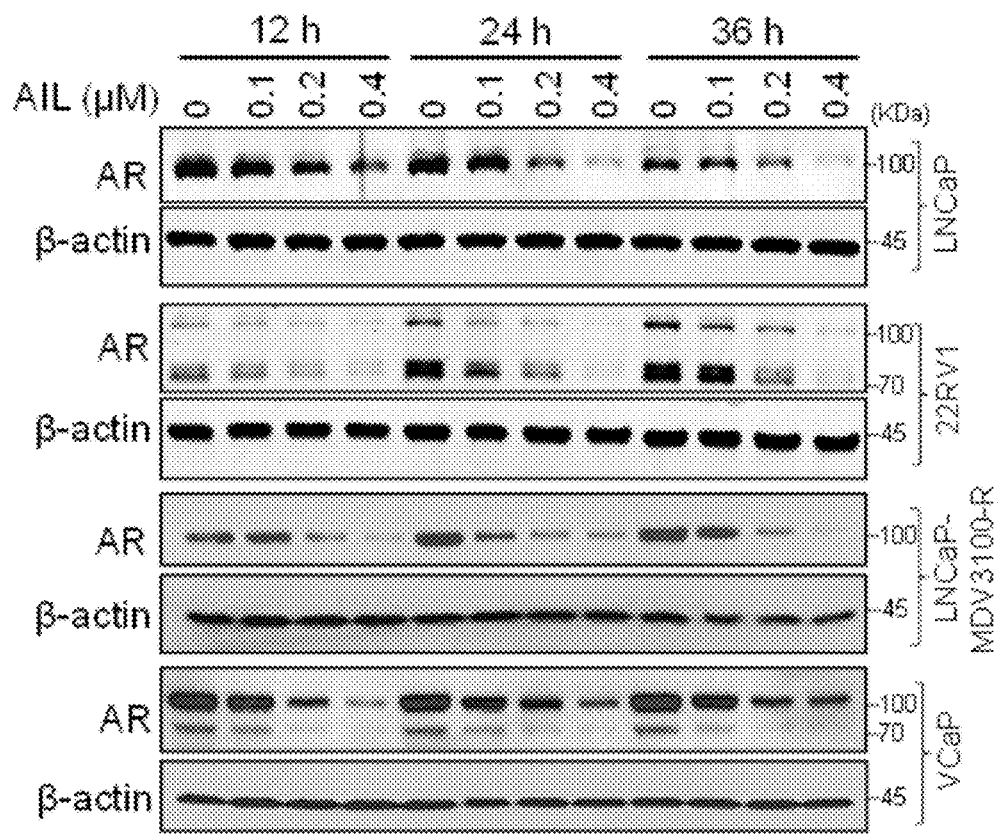
FIG. 3A-FIG. 3G. Down-regulation of AR protein levels in vitro and in vivo by AIL. (A) LNCaP, 22RV1, LNCaP-MDV3100-R and VCaP cells were treated with indicated concentrations of AIL for 12, 24 and 36 hours. Then cells were lysed and AR protein level was measured by Western blotting analysis. (B) LNCaP, 22RV1 and c4-2b cells were treated for 12 hours with indicated concentrations of AIL with or without R1881 and the AR protein level was measured by Western blotting analysis. (C) AR null PC3 cells were transfected with AR-GFP in serum-free conditions for 24 hours and treated with DMSO (control), R1881 (10 nM) or combined AIL (0.4 μM) and R1881 (10 nM). AR-GFP images were taken at 2 hours or 10 hours after treatment. Five pictures were randomly selected and the GFP-AR fluorescence in cytoplasm and nucleus was quantitated using Image-Pro Plus 4.5 software (Media Cybernetics, Silver Spring, USA). The arrows indicate the location of AR-GFP. Data was expressed as mean±s.d.; Student's t-tests were performed; *P<0.05, P<0.01. Scale bars, 10 μm. (D) LNCaP and 22RV1 cells were treated with the indicated concentrations of AIL for 12 and 24 hours. Cells were lysed and AR, HSP90 and HSP70 protein levels were measured by western blotting analysis. (E) Four representative tumor samples per group were lysed. AR, HSP90, HSP70 and HSP40 protein levels were measured by Western blotting analysis. (F) The mRNA levels of PSA, TMPRSS2, total AR and AR-V7 were measured by quantitative-PCR and normalized to GAPDH. The sequences of quantitative-PCR primers were listed in Table 1. Data was expressed as mean±s.d.; Two-way ANOVA followed by Bonferroni multiple comparison test were performed; *P<0.001. (G) Photographs of xenografts treated i.p. with DMSO (control group), 10 mgkg$^{-1}$ MDV and 2 mgkg$^{-1}$ AIL with corresponding IHC for AR and Ki67. Scale bars, 20 μm.
Figure 3B:
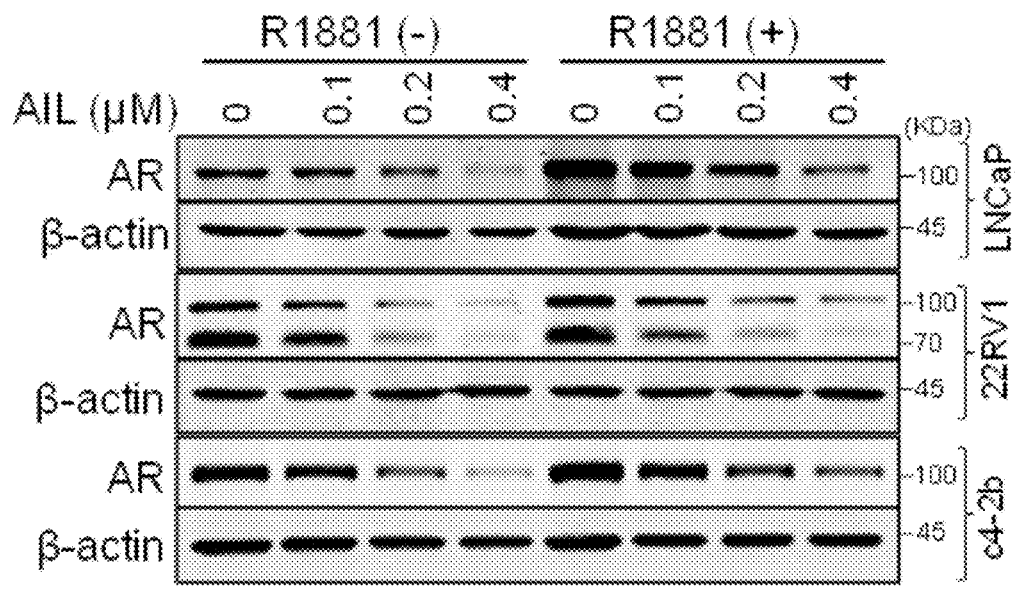
Figure 3C:
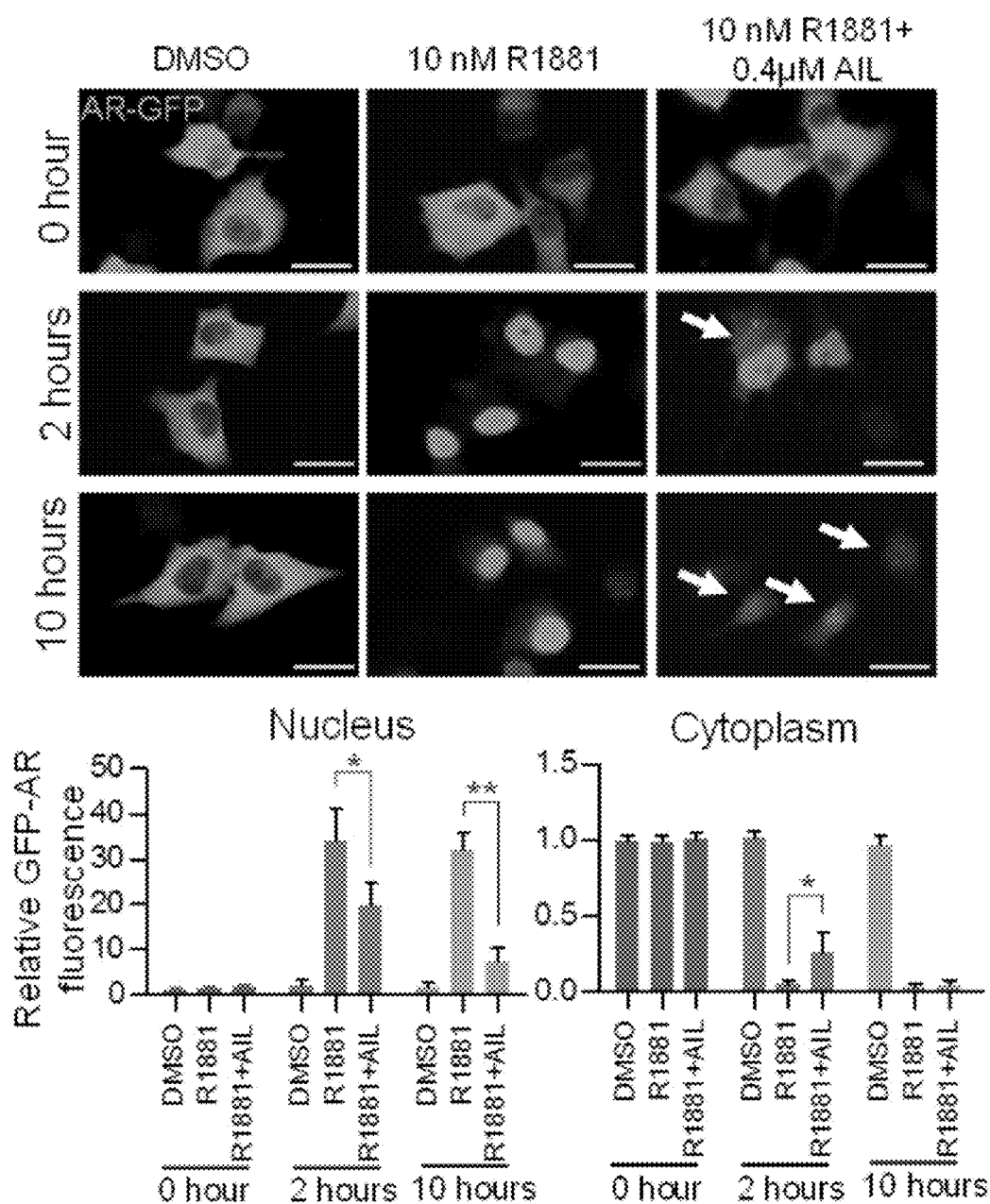
Figure 3D:
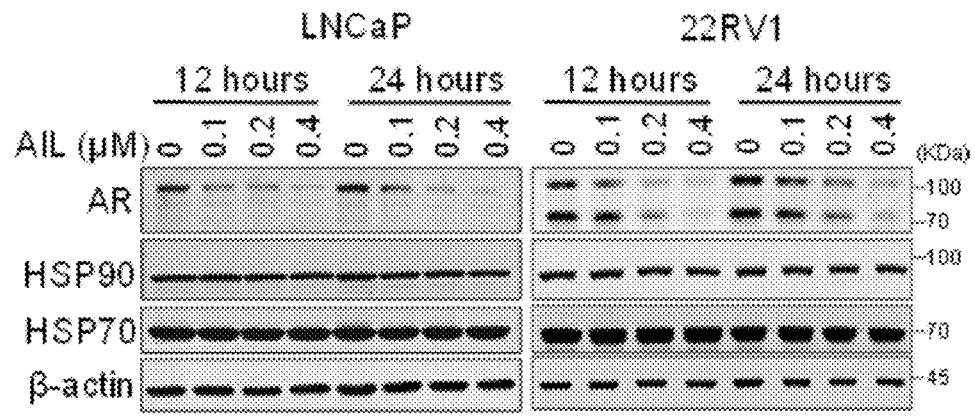
Figure 3E:
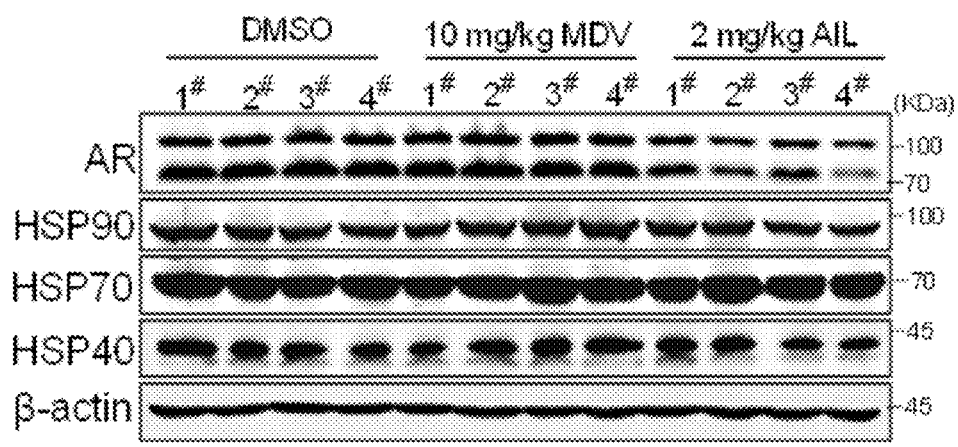
Figure 3F:
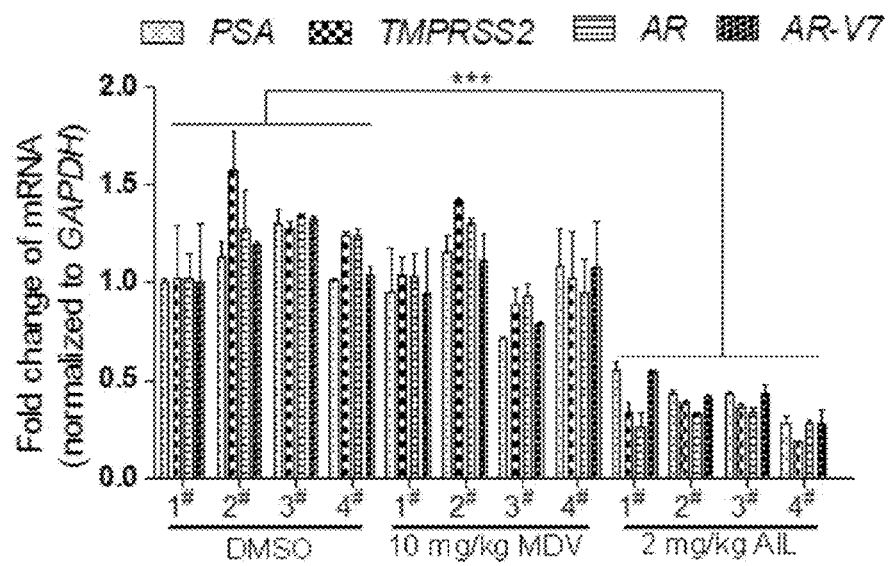
Figure 3G:
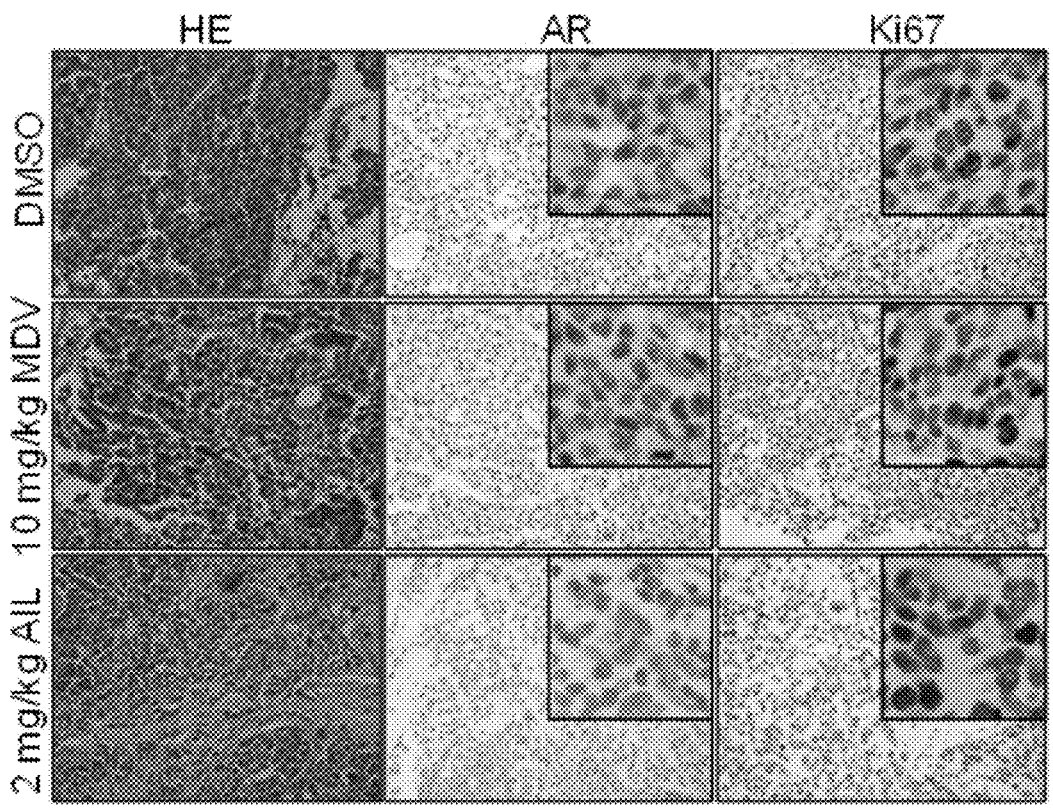
Figure 16C:
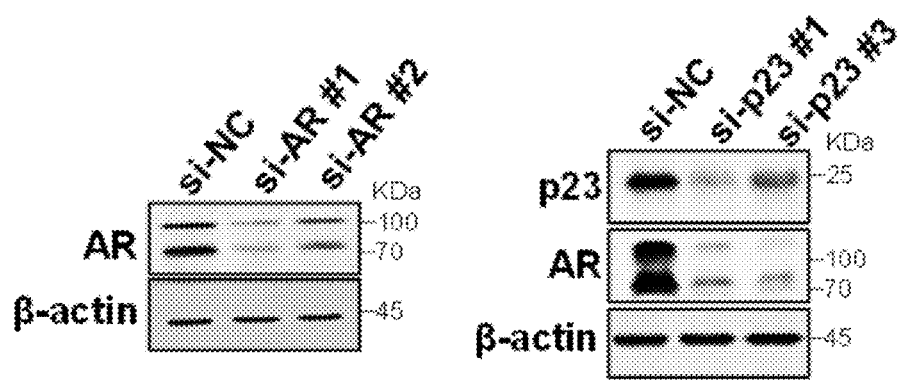
Figure 16C:
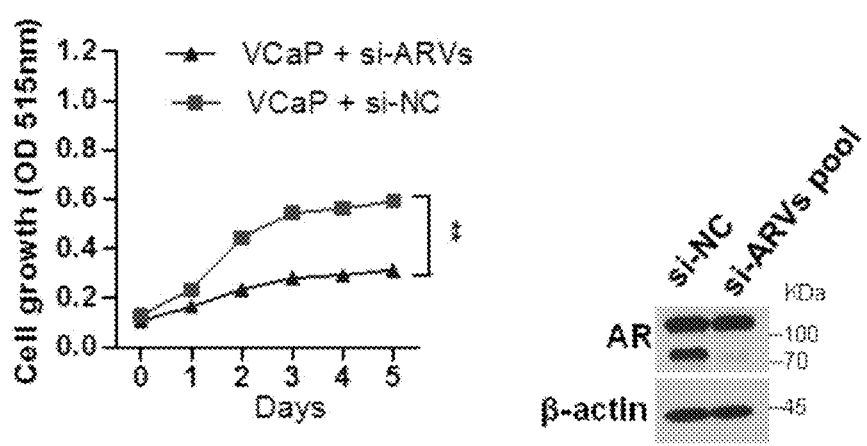
Figure 16D:
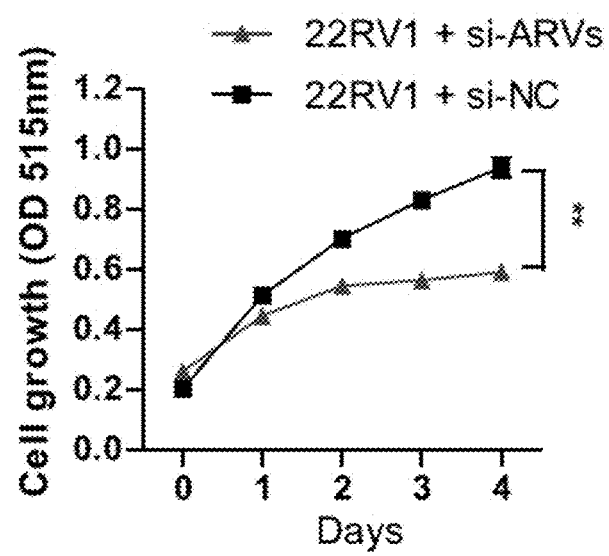
Figure 16D:
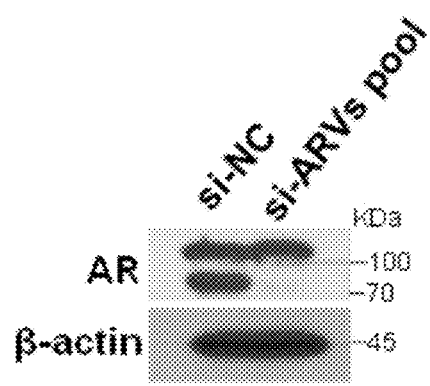
Figure 16E:
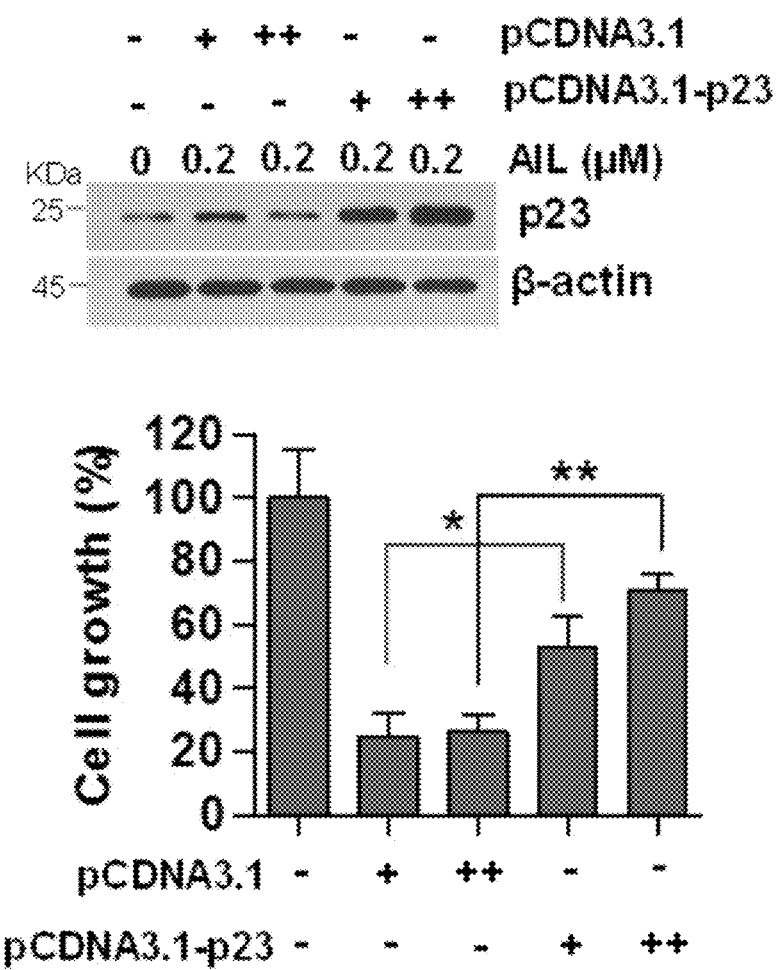

To investigate the mechanism of AR transcriptional activity inhibition by AIL, we firstly determined the AR protein level after AIL treatment in PCa cell lines. AIL potently reduced AR protein expression in a dose-dependent manner in LNCaP, 22RV1, LNCaP-MDV3100-R, and VCaP cell lines (FIG. 3A). In AR positive PCa cell lines, AR was more stable and had a higher basal level in the presence of synthetic androgen R1881; we observed that AIL reduced the AR protein level both in the absence and in the presence of R1881 (FIG. 3B and FIG. 13A). Notably, AIL down-regulated the truncated splice variants of AR (FIGS. 13B and 13c) which were continually active and resistant to AR antagonist therapy. Indeed, knockdown of AR-Vs decreased the proliferation of VCaP and 22RV1 cells which have high expression of AR-Vs (FIGS. 16C and D). Furthermore, we examined whether AIL prevented AR nuclear translocation by transfecting an AR-GFP fusion protein into PC3 cells. As expected, the nuclear translocation of AR-GFP induced by R1881 was decreased by AIL in PC3 cells (FIG. 3C and FIG. 13D). The HSP90 complex plays a major role in stabilizing unliganded AR[24]. Therefore, we examined whether AIL affected the members of the HSP90 complex. Unexpectedly, AIL did not down-regulate the AR molecular chaperones HSP90 and HSP70 in PCa cells (FIG. 3D). We further confirmed this phenomenon in the AIL-treated 22RV1 orthotopic xenografts. As demonstrated in FIGS. 3E and F, AIL reduced the expression of AR protein and its target genes but had no effect on the AR molecular chaperones HSP90, HSP70 and HSP40 in vivo. AR down-regulation and proliferation inhibition by AIL treatment in 22RV1 orthotopic xenografts were also confirmed by immunohistochemistry (FIG. 3G). Additionally, in an in vivo assay, treatment with AIL decreased the mRNA level of the AR-splice variant AR-V7 as well as total AR (FIG. 3F), which might be caused by a secondary effect of long-term AIL treatment.

Example 5 Induction of AR Degradation by AIL

Figure 4A:
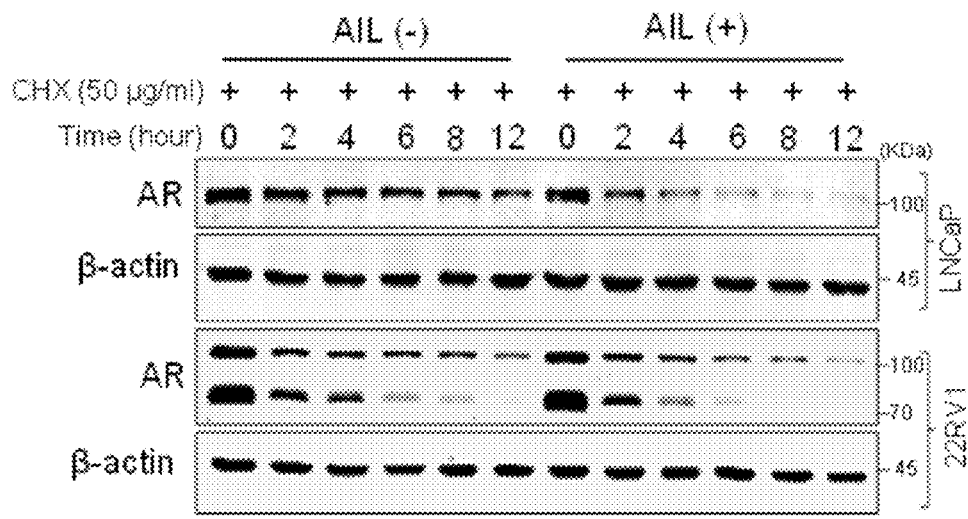
FIG. 4A-FIG. 4F. Reduction of AR protein stability by AIL. (A) LNCaP and 22RV1 cells were treated with cyclo-heximide (CHX) with or without AIL for various lengths of time. AR protein level was measured by Western blotting analysis. (B) LNCaP cells were cultured in c-FBS for 5 days and treated with AIL in the absence or presence of 10 nM R1881 for 12 hours. Total RNA was extracted and quantitative-PCR was performed. The AR-V7 mRNA level was detected in 22RV1 cells which were treated with the indicated concentrations of AIL for 12 hours. The expression of AR, AR-V7 and PSA was normalized to β-actin expression. Data was expressed as mean±s.d. of three independent assays; Student's t-tests were performed; *P<0.05. (C) LNCaP and 22RV1 cells were treated with various concentrations of AIL with or without MG132 (10 μM) and AR protein level was measured by Western blotting analysis. (D) Immunoprecipitation (IP) was done using anti-AR and immunoblotting performed with an anti-ubiquitin antibody. Input: immunoblot of lysates probed with AR antibody. (E) 22RV1 cells were treated with or without AIL in the presence of MG132. IP was done using anti-AR, anti-HSP90, and anti-HSP70 antibodies and immunoblotting (IB) was done with anti-AR, anti-HSP90, anti-HSP70 and anti-HSP40 antibodies. (F) HSP90α activity was measured by fluorescence polarization binding assay using FITC-geldanamycin in the presence of AIL or 17-AAG (positive control).
Figure 4B:
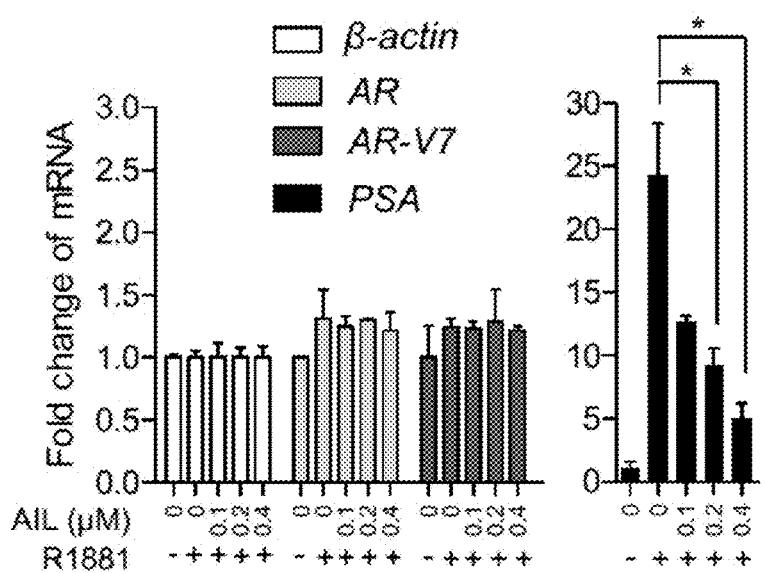
Figure 4C:
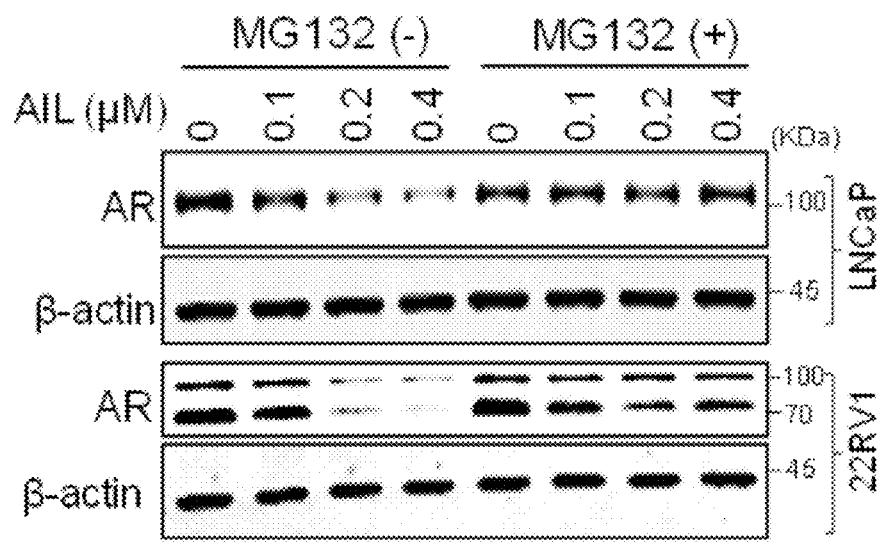
Figure 4D:
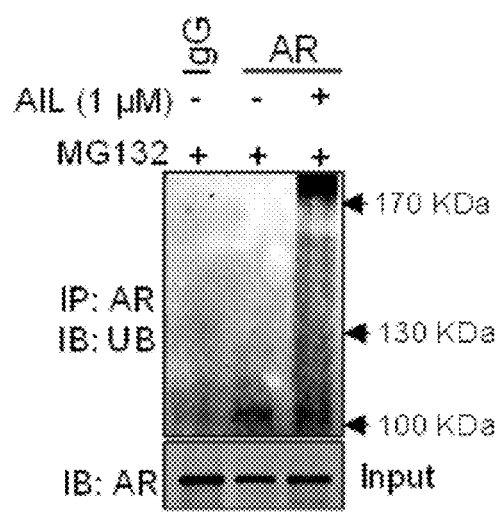
Figure 4E:
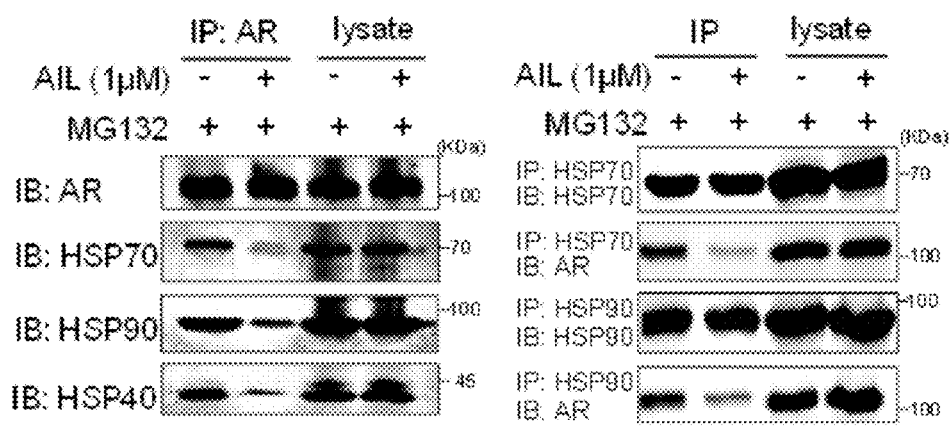

To investigate why AIL reduced the expression of AR protein but not its molecular chaperones, we tested the effect of AIL on AR protein stability. Surprisingly, AR protein stability was significantly reduced under AIL treatment (FIG. 4A). However, there was no significant effect on AR and AR-V7 mRNA when treated with the same concentration of AIL, although the PSA mRNA level was decreased (FIG. 4B). To test whether AIL induced AR degradation through the proteasome pathway, we treated cells with the proteasome inhibitor MG-132, which resulted in a marked suppression of AIL-induced AR depletion (FIG. 4C). More importantly, treatment with AIL induced ubiquitination of AR (FIG. 4D). Interestingly, while AIL treatment decreased AR, AKT as well as Cdk4 protein levels, it did not influence their chaperones HSP90, HSP70 and HSP40 which were all essential for the HSP90-HSP70 chaperone complex (FIG. 13F). To further illustrate this mechanism, we performed co-immunoprecipitation and observed that AIL prevented the interaction of AR with HSP90 and HSP70 as well as HSP40 (FIG. 4E). Together with the decreased protein stability, these data suggested that AIL might induce AR degradation by disrupting the interaction of AR with its chaperones HSP90 and HSP70, resulting in AR ubiquitination and degradation. In addition, AIL treatment led to AKT and Cdk4 downregulation, potentially driving the decreased proliferation in AIL-treated cells.

Figure 4F:
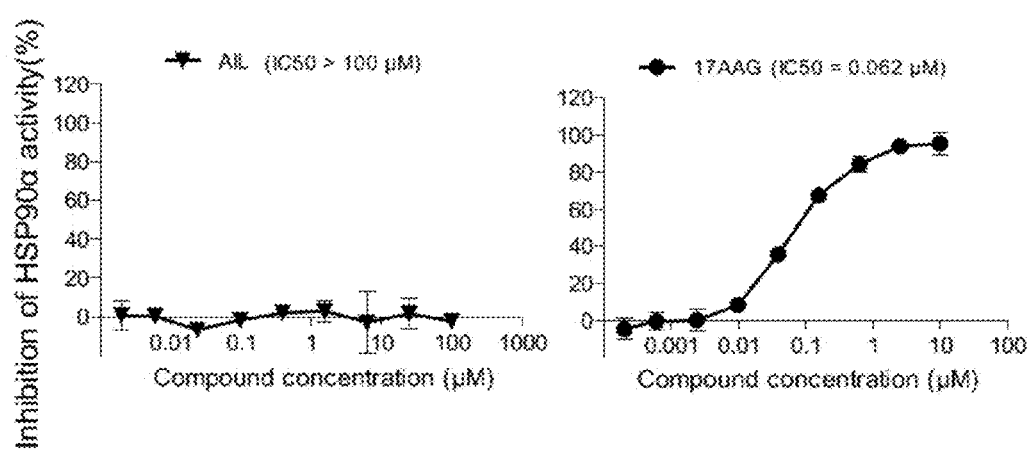

Given that AIL disrupted the interaction of AR with its chaperone HSP90, we then tested whether AIL inhibited HSP90 activity. Using the geldanamycin-FITC fluorescence polarization assay, we found that AIL did not inhibit HSP90 activity (FIG. 4F). We also observed that 17-AAG induced up-regulation of HSP90 and HSP70 protein but AIL did not influence them (FIG. 13E), suggesting that AIL, unlike 17-AAG, was not an HSP90 inhibitor.

Example 6 Interaction of AIL with p23 In Vitro

Foldosome complex assembly occurs through a series of steps, beginning with HSP40 and HSP70 binding to AR, followed by HSP90 and HOP, and then succeeded by ATP-dependent binding of p23, FKBP51 and FKBP52 which displace HSP40, HSP70, and HOP[24]. Additional foldosome proteins include cdc37 and HDAC6[36]. Accordingly, we next determined whether AIL disturbed the interaction between these proteins and HSP90. AIL obviously prevented the interaction between p23 and HSP90, but had no significant influence on the interaction of other proteins with HSP90 (FIG. 5A). By Biacore assay, we confirmed that there was no interaction between AIL and HSP90 (FIG. 15A). However, AIL interacted directly with p23 ($K_D=1.79 \times 10^{-06}$ M) (FIG. 5B). Celastrol (CEL) was used as a positive control of p23 interaction (FIG. 15B). We also performed a molecular docking modeling simulation using the x-ray crystal structure of the p23 functional domain, and identified a potential binding site on the surface of p23 that could reasonably accommodate AIL binding (FIG. 5C and FIG. 15C). In addition, both treatment with AIL and CEL down-regulated the protein level of AR rather than the chaperones HSP90 and HSP70 (FIG. 16A), indicating that AIL and CEL might share a similar mechanism. Furthermore, p23 knockdown ablated the ability of AIL treatment to induce cell growth arrest (FIG. 16B). Also, overexpression of p23 dose-dependently rescued AIL-mediated cell proliferation inhibition (FIG. 16E), suggesting that p23 might be a critical target of AIL. Besides, we found that AIL indeed suppressed the activities of both glucocorticoid receptor (GR) and progesterone receptor (PR) (FIG. 13G), suggesting that AIL is not specific in targeting AR since p23 has different client proteins. However, compared with AR, the inhibition of GR and PR by AIL is less sensitive. For example, 0.4 µM AIL resulted in 70% inhibition of AR-induced reporter activities, but AIL just blocked the PR and GR-induced reporter activities by about 30% (FIG. 13G).

Figure 5D:
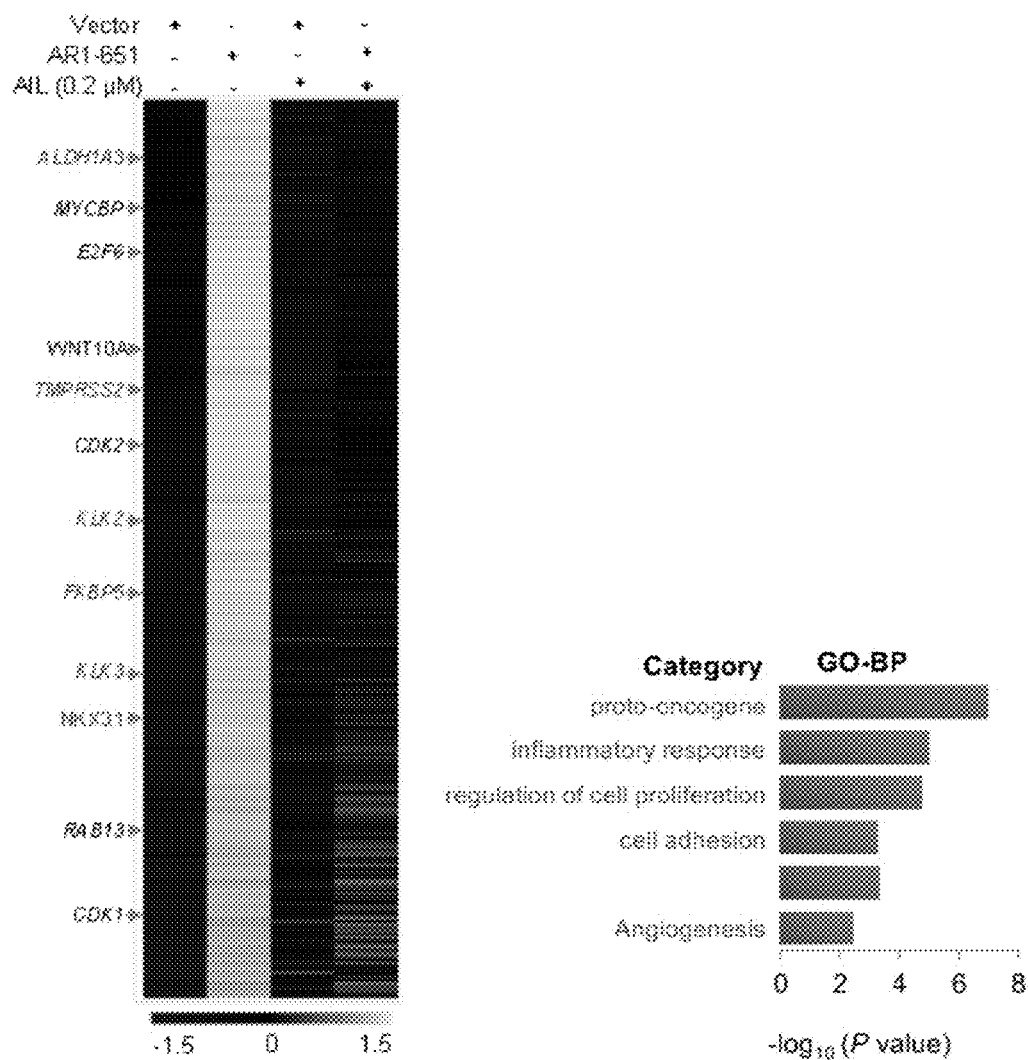

To investigate if AIL suppressed the functioning of continually active AR lacking the LBD, we performed RNA-seq after treating LNCaP cells with or without AIL in the absence or presence of $AR_{1-651}$. Indeed, as shown in FIG. 5D (top), AIL strongly suppressed $AR_{1-651}$-induced gene expression, supporting the potential therapeutic use of AIL in CPRC. Those genes not only included the classic androgen-regulated genes e.g. KLK3, FKBP5 and NKX3.1 (indicated by red), but also involved other non-classic androgen-induced genes e.g. MYCBP, WNT10A, CDK2 (indicated by black), indicating that AR mutations causing LBD loss might lead to extra transcriptional functions and contribute to drug resistance. Gene Ontology (GO) analysis (FIG. 5D, bottom) demonstrated that $AR_{1-651}$-induced genes were involved in cell cycle, proliferation and cell adhesion, suggesting that AR lacking the LBD has oncogenic functions.

Figure 5E:
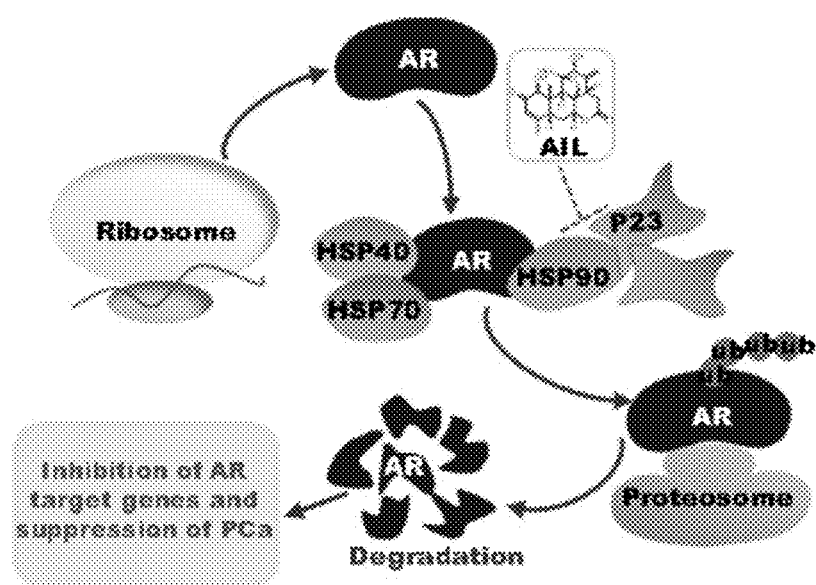

To sum up, all these data indicate that AIL prevented the interaction of p23 and HSP90 and decreased the interaction between AR and the chaperones, resulting in the ubiquitination of AR. Consequently, AR was degraded by the proteasome, AR target gene expression declined and PCa growth was blocked (FIG. 5E).

Example 7 Evaluation of AIL Pharmacokinetics and CYP Inhibition

Figure 6A:
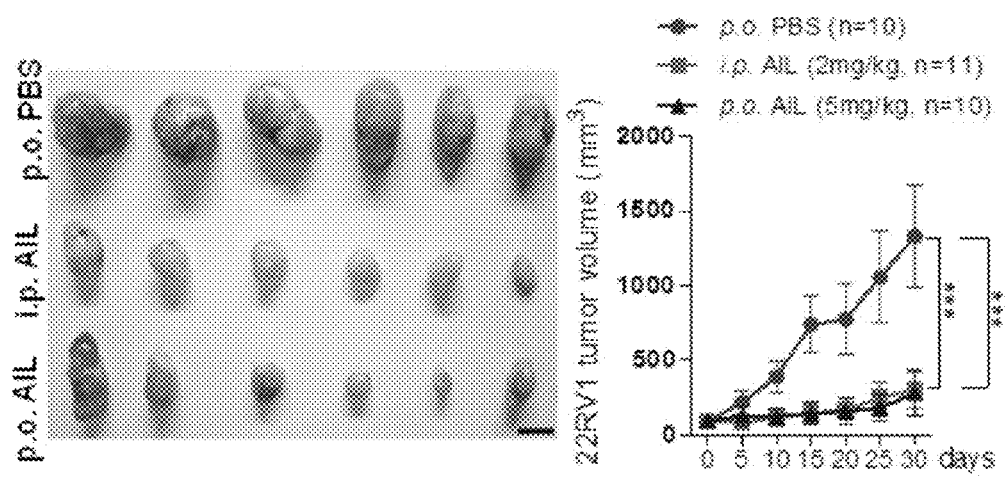
FIG. 6A-FIG. 6H. Pharmacokinetic studies of AIL. (A) 22RV1 tumor-bearing mice were treated with p.o. AIL or i.p. AIL and the tumor volumes were measured every five days; p.o. PBS served as control. Images show tumors at harvest (30 days after treatment). Scale bar, 1 cm. (B) The concentration of AIL in plasma was determined by LC-MS/MS following the last drug administration of p.o. AIL or i.p. AIL in tumor bearing mice. (C) Effect of AIL on the activities of rat or human liver cytochrome P450 (CYP) enzymes in vitro. Rat liver microsomes or human liver microsomes were incubated with various concentrations of AIL and the activities of indicated CYP enzymes were measured. (D,E) The expression of CYP2C11, CYP3A1 and CYP1A2 in representative livers of the mice treated with p.o. AIL ori.p. AIL or vehicle control was measured by Western blotting analysis (D) and the livers were photographed and stained with HE (e). Scale bar, the black scale bar is 1 cm (top) and the white scale bar is 50 μm (bottom). (F) The concentration of AIL in rat plasma was determined by LC-MS/MS after administration of p.o. AIL or i.v. AIL (G) 22RV1 tumor-bearing mice were treated with p.o. AIL or i.p. AIL and mouse body weight was measured every five days. (H) Intestines and stomachs of the mice were dissected and images were taken at the end of AIL administration. Scale bar, 1 cm. Data represent the mean±s.d.; *P<0.05, P<0.01, *P<0.001 by one-way ANOVA followed by Bonferroni multiple comparison test.
Figure 17:
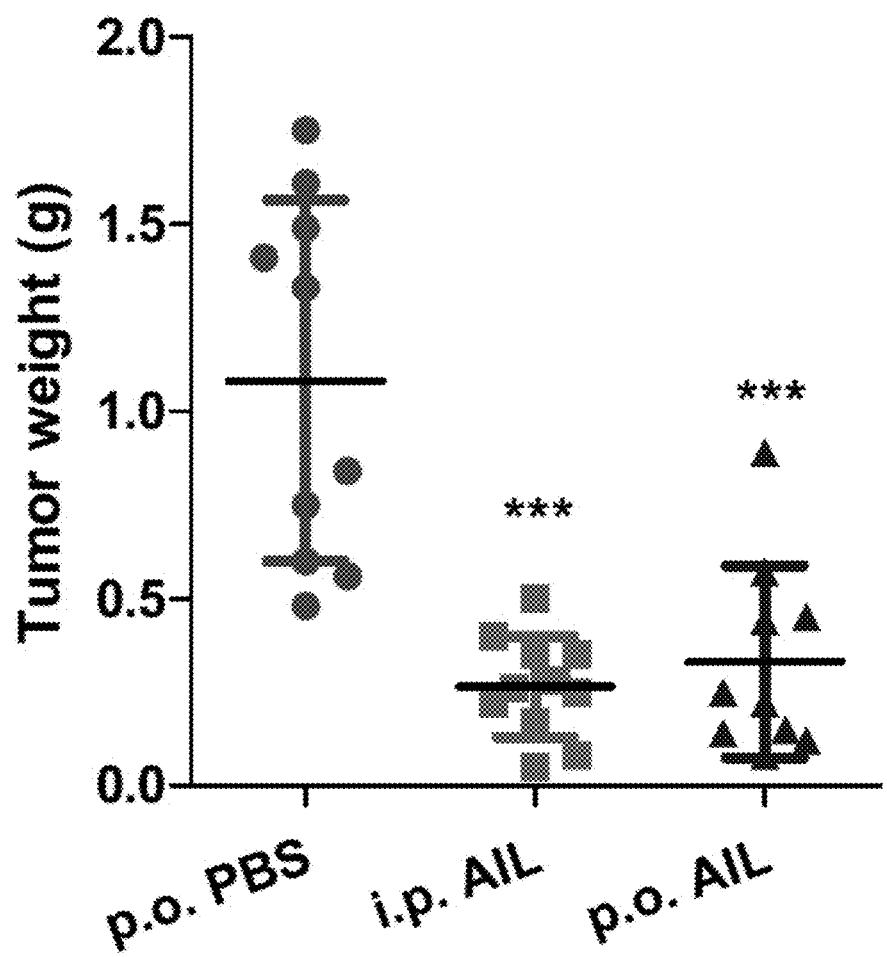
FIG. 17. The effects of i.p. and p.o. administration of AIL on the. $3 \times 10^6$ 22RV1 cells were injected with 0.1 ml PBS into the right flank of nude mice. After tumor nodules were allowed to grow to a volume about 100 $mm^3$, the tumor bearing mice were treated with 2 mg/kg/day (i.p.) or 5 mg/kg/day (p.o.) or vehicle control (p.o.) for 30 days. The tumor weight was measured at the end of the experiment. Data was expressed as mean±s.d.; Student's t-tests were performed; ***P<0.001.

Compounds with good absorption, distribution, metabolism, excretion, and toxicity (ADME/Tox) properties are likely to increase the odds of drug discovery success. Since AIL was pharmacologically potent against CRPC in animal models, we evaluated the drug-like properties of AIL. Both oral (p.o.) and intraperitoneal (i.p.) administration of AIL were highly efficient in animal models. As shown in FIG. 6A and FIG. 17, compared with the control group, i.p. administration (2 mg $kg^{-1}$ per day AIL) and p.o. administration (5 mg $kg^{-1}$ per day AIL) reduced the tumor volume of MDV3100-resistant 22RV1 xenografts by 77.5%. We noted a modest decrease in mouse body weight in the p.o. treated group (FIG. 6G), which was caused by neither overdose nor liver toxicity (FIG. 6E), but rather by AIL-induced stomach injury (FIG. 6H).

Next we determined the pharmacokinetics (PK) of AIL based on the pharmacodynamic (PD) efficiency of AIL in 22RV1 xenografts, because the PK-PD model of AIL could confirm the dose levels and drug exposures necessary for AIL to achieve potent antitumor activity in vivo. The concentration of AIL in nude mouse plasma was 1216.2 ng $mL^{-1}$ at 10 min after i.p. administration. This concentration far exceeded its effective concentration in vitro ($IC_{50}=69$ nM, 25.94 ng $mL^{-1}$), although the minimal effective concentration in vivo is unknown. The period that the concentrations of AIL in the plasma remained above the in vitro $IC_{50}$ lasted for up to 2 hours (44.83 ng mL$^{-1}$) (FIG. 6B).

Figure 6B:
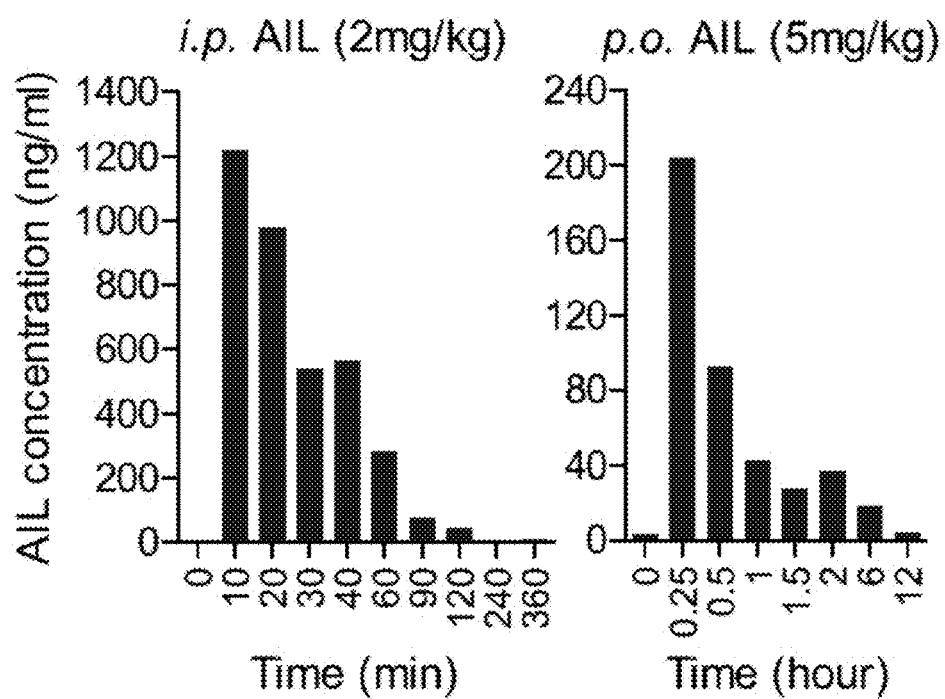
Figure 6C:
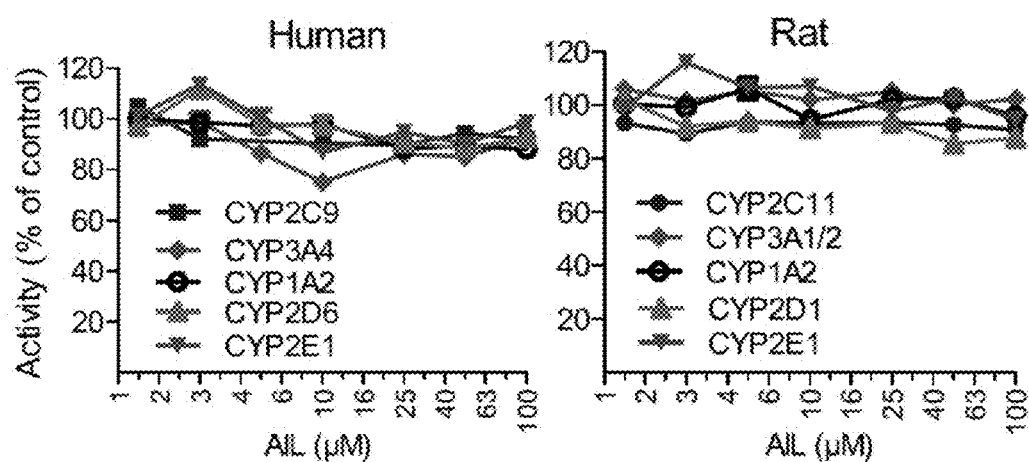
Figure 6D:
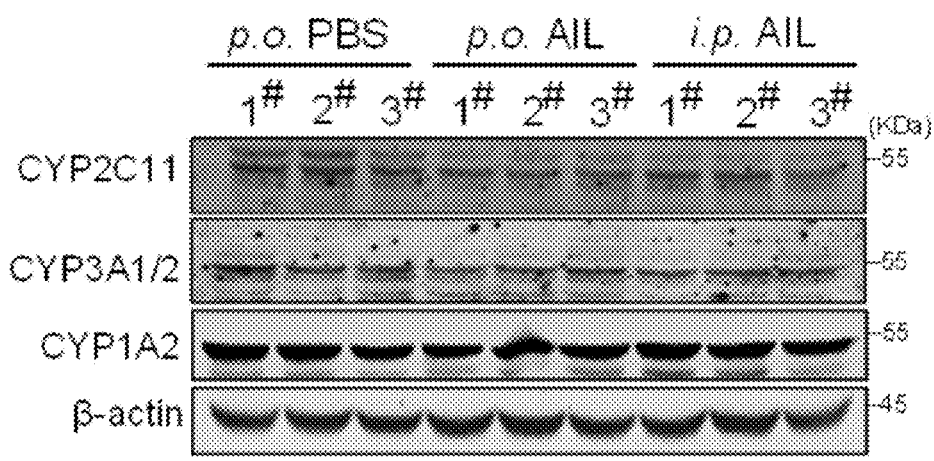
Figure 6E:
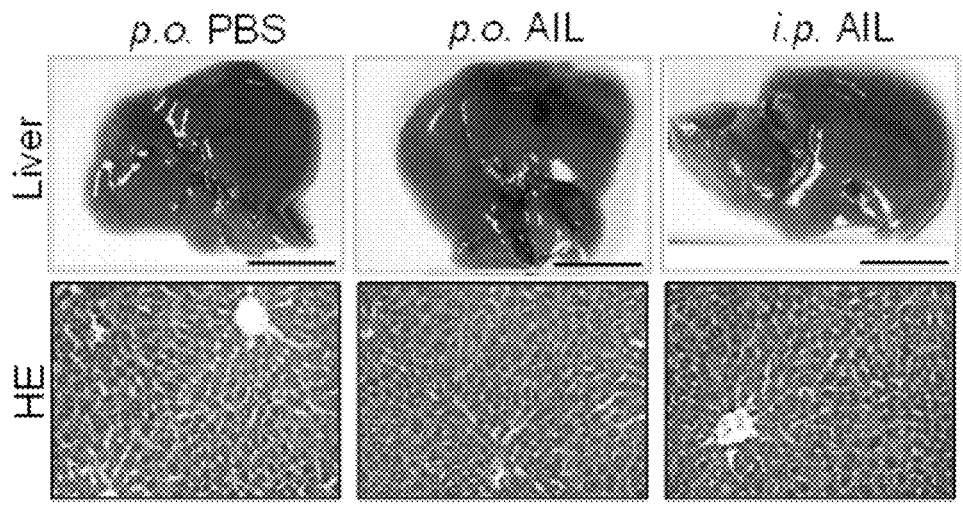

In the p.o. administration group, the plasma AIL concentration reached 203.9 ng mL$^{-1}$ at 15 min after administration (FIG. 6B). The period that the AIL plasma concentration remained above $IC_{50}$ in vitro was about 6 hours because of the absorption process. Moreover, the p.o. exposure was lower than the i.p. exposure after dose normalization because of intestinal absorption as well as first-pass metabolism. Since the concentration of AIL remaining in the plasma immediately before the next administration was 1.43 ng mL$^{-1}$ for the i.p. group and 1.84 ng mL$^{-1}$ for the p.o. group, respectively, the efficacy of AIL in vivo might not last for the whole 24 hour treatment interval time.

Figure 6F:
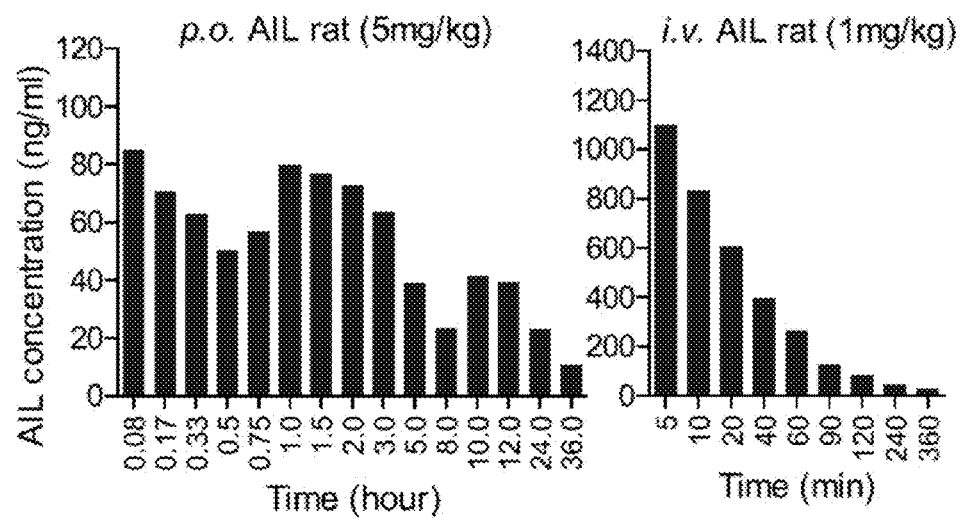
Figure 6G:
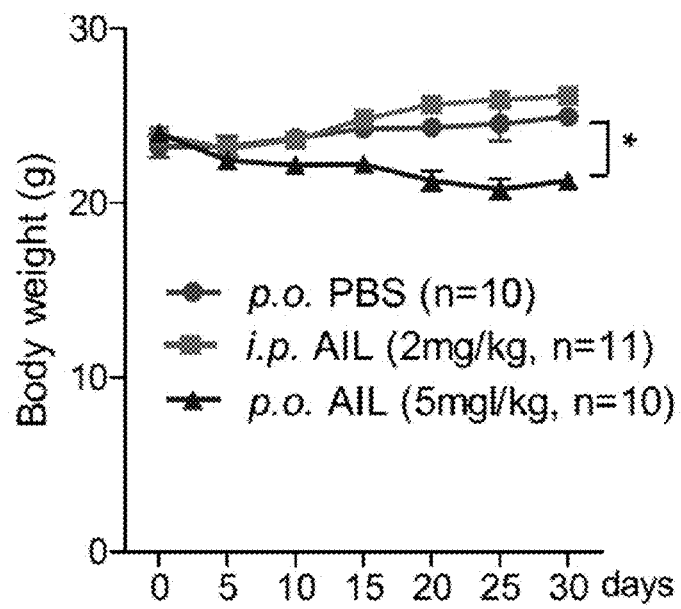
Figure 6H:
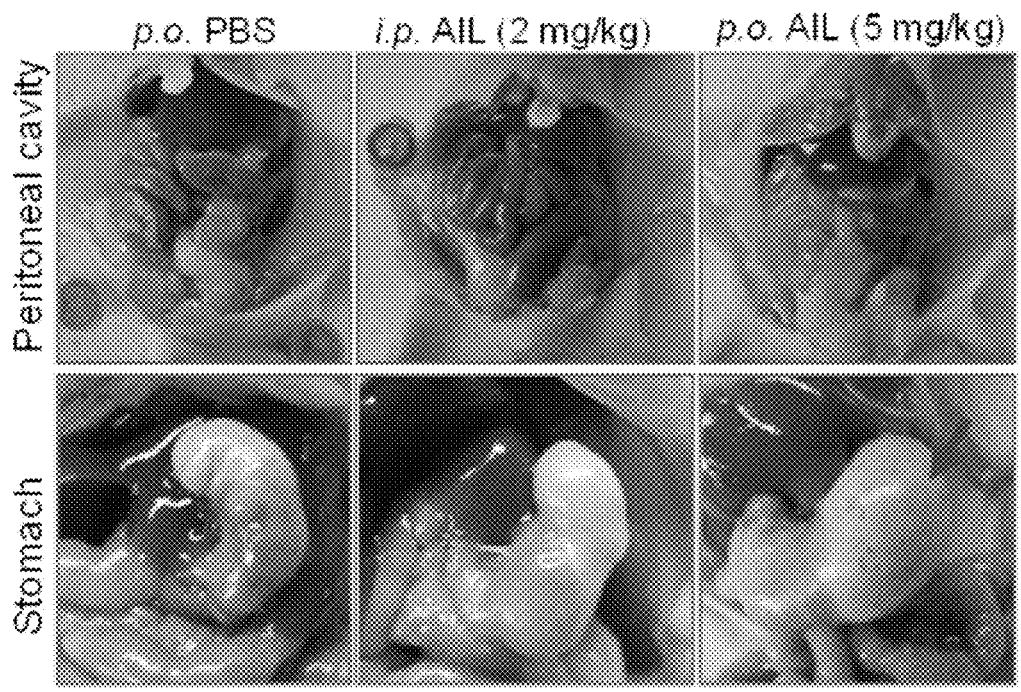

The preclinical pharmacokinetics of AIL were also evaluated in Sprague-Dawley rats. Our previous studies have shown that the pharmacokinetic profiles of AIL in rats after intravenous (i.v.) administration exhibit linear pharmacokinetics[37]. Here we found that AIL was absorbed quickly, eliminated rapidly and distributed widely in tissues after oral administration (FIG. 6F and Table 4). Moreover, the oral bioavailability of AIL was 25.7%, which was well within the range of acceptable bioavailability (>20%), suggesting that AIL could be a potential drug candidate in clinical trials.

In addition, the effect of AIL on the activity of CYP enzymes was evaluated. As shown in FIG. 6C, AIL (1.25 µM to 100 µM) had no significant inhibitory effects on the main CYP isoforms (CYP1A2, 2C9/11, 2D1/6, 2E1 and 3A1/2/4) in humans and rats. Finally, we noticed that AIL did not exert obvious hepatotoxicity or significant influence on the expression of CYP2C11, CYP3A1/2 and CYP1A2 in the livers of mice (FIGS. 6D and E).

While the invention has been described above in connection with one or more embodiments, it should be understood that the invention is not limited to those embodiments, and the description is intended to cover all alternatives, modifications, and equivalents, as may be included within the spirit and scope of the appended claims. All referenced cited herein are further incorporated by reference in their entirety.

REFERENCES CITED

1. Siegel R L, Miller K D, Jemal A. Cancer statistics, 2015. *CA: a cancer journal for clinicians* 65, 5-29 (2015).
2. Torre L A, Bray F, Siegel R L, Ferlay J, Lortet-Tieulent J, Jemal A. Global cancer statistics, 2012. *CA: a cancer journal for clinicians* 65, 87-108 (2015).
3. Dutt S S, Gao A C. Molecular mechanisms of castration-resistant prostate cancer progression. *Future oncology (London, England)* 5, 1403-1413 (2009).
4. Linja M J, Savinainen K J, Saramaki O R, Tammela T L, Vessella R L, Visakorpi T. Amplification and overexpression of androgen receptor gene in hormone-refractory prostate cancer. *Cancer research* 61, 3550-3555 (2001).
5. Chen C D, et al. Molecular determinants of resistance to antiandrogen therapy. *Nature medicine* 10, 33-39 (2004).
6. Sun S, et al. Castration resistance in human prostate cancer is conferred by a frequently occurring androgen receptor splice variant. *The Journal of clinical investigation* 120, 2715-2730 (2010).
7. Scher H I, Sawyers C L. Biology of progressive, castration-resistant prostate cancer: directed therapies targeting the androgen-receptor signaling axis. *Journal of clinical oncology: official journal of the American Society of Clinical Oncology* 23, 8253-8261 (2005).
8. Lonergan P E, Tindall D J. Androgen receptor signaling in prostate cancer development and progression. *Journal of carcinogenesis* 10, 20 (2011).
9. Koochekpour S. Androgen receptor signaling and mutations in prostate cancer. *Asian journal of andrology* 12, 639-657 (2010).
10. Bishr M, Saad F. Overview of the latest treatments for castration-resistant prostate cancer. *Nature reviews Urology* 10, 522-528 (2013).
11. Scher H I, et al. Increased survival with enzalutamide in prostate cancer after chemotherapy. *The New England journal of medicine* 367, 1187-1197 (2012).
12. Fizazi K. et al. Abiraterone acetate for treatment of metastatic castration-resistant prostate cancer: final overall survival analysis of the COU-AA-301 randomised, double-blind, placebo-controlled phase 3 study. *The Lancet Oncology* 13, 983-992 (2012).
13. Mostaghel E A, et al. Resistance to CYP17A1 inhibition with abiraterone in castration-resistant prostate cancer: induction of steroidogenesis and androgen receptor splice variants. *Clinical cancer research: an official journal of the American Association for Cancer Research* 17, 5913-5925 (2011).
14. Li Y, Chan S C, Brand L J, Hwang T H, Silverstein K A, Dehm S M. Androgen receptor splice variants mediate enzalutamide resistance in castration-resistant prostate cancer cell lines. *Cancer research* 73, 483-489 (2013).
15. Antonarakis E S, et al. AR-V7 and resistance to enzalutamide and abiraterone in prostate cancer. *The New England journal of medicine* 371, 1028-1038 (2014).
16. Francini E, Petrioli R, Roviello G. No clear evidence of a clinical benefit of a sequential therapy regimen with abiraterone acetate and enzalutamide. *Expert review of anticancer therapy* 14, 1135-1140 (2014).
17. Claessens F, et al. Emerging mechanisms of enzalutamide resistance in prostate cancer. *Nature reviews Urology* 11, 712-716 (2014).
18. Dehm S M, Schmidt L S, Heemers H V, Vessella R L, Tindall D J. Splicing of a novel androgen receptor exon generates a constitutively active androgen receptor that mediates prostate cancer therapy resistance. *Cancer research* 68, 5469-5477 (2008).
19. Guo Z, et al. A novel androgen receptor splice variant is up-regulated during prostate cancer progression and promotes androgen depletion-resistant growth. *Cancer research* 69, 2305-2313 (2009).
20. Hu R, et al. Ligand-independent androgen receptor variants derived from splicing of cryptic exons signify hormone-refractory prostate cancer. *Cancer research* 69, 16-22 (2009).
21. Hu R, et al. Distinct transcriptional programs mediated by the ligand-dependent full-length androgen receptor and its splice variants in castration-resistant prostate cancer. *Cancer research* 72, 3457-3462 (2012).
22. Yu Z, et al. Rapid induction of androgen receptor splice variants by androgen deprivation in prostate cancer. *Clinical cancer research: an official journal of the American Association for Cancer Research* 20, 1590-1600 (2014).
23. Chan S C, Li Y, Dehm S M. Androgen receptor splice variants activate androgen receptor target genes and support aberrant prostate cancer cell growth independent of canonical androgen receptor nuclear localization signal. *The Journal of biological chemistry* 287, 19736-19749 (2012).
24. Cano L Q, Lavery D N, Bevan C L. Foldosome regulation of androgen receptor action in prostate cancer. *Molecular and cellular endocrinology* 369, 52-62 (2013).

25. Azad A A, Zoubeidi A, Gleave M E, Chi K. N. Targeting heat shock proteins in metastatic castration-resistant prostate cancer. *Nature reviews Urology* 12, 26-36 (2015).
26. Kim Y S, et al. Update on Hsp90 inhibitors in clinical trial. *Current topics in medicinal chemistry* 9, 1479-1492 (2009).
27. Deckers L, Workman P. Hsp90 molecular chaperone inhibitors: are we there yet? *Clinical cancer research: an official journal of the American Association for Cancer Research* 18, 64-76 (2012).
28. Forafonov F, Toogun O A, Grad I, Suslova E, Freeman B C, Picard D. p23/Sba1p protects against Hsp90 inhibitors independently of its intrinsic chaperone activity. *Molecular and cellular biology* 28, 3446-3456 (2008).
29. Cano L Q, et al. The co-chaperone p23 promotes prostate cancer motility and metastasis. *Molecular oncology* 9, 295-308 (2015).
30. Reebye V, et al. Role of the HSP90-associated cochaperone p23 in enhancing activity of the androgen receptor and significance for prostate cancer. *Molecular endocrinology* (Baltimore, Md.) 26, 1694-1706 (2012).
31. Simpson N E, et al. High levels of Hsp90 cochaperone p23 promote tumor progression and poor prognosis in breast cancer by increasing lymph node metastases and drug resistance. *Cancer research* 70, 8446-8456 (2010).
32. Oxelmark E, Roth S M, Brooks P C, Braunstein S E, Schneider R J, Garabedian M J. The cochaperone p23 differentially regulates estrogen receptor target genes and promotes tumor cell adhesion and invasion. *Molecular and cellular biology* 26, 5205-5213 (2006).
33. Hartig P C, et al. Development of two androgen receptor assays using adenoviral transduction of MMTV-luc reporter and/or hAR for endocrine screening. *Toxicological sciences: an official journal of the Society of Toxicology* 66, 82-90 (2002).
34. Okunade A L, Bikoff R E, Casper S J, Oksman A, Goldberg D E, Lewis W H. Antiplasmodial activity of extracts and quassinoids isolated from seedlings of *Ailanthus altissima* (Simaroubaceae). *Phytotherapy research: PTR* 17, 675-677 (2003).
35. Rosati A, Quaranta E, Ammirante M, Turco M C, Leone A, De Feo V Quassinoids can induce mitochondrial membrane depolarisation and caspase 3 activation in human cells. *Cell death and differentiation* 11 Suppl 2, S216-218 (2004).
36. Hartl F U, Bracher A, Hayer-Hartl M. Molecular chaperones in protein folding and proteostasis. *Nature* 475, 324-332 (2011).
37. Chen A, Qin X, Lu J, Yi Z, Liu M, Wang X. Development of a validated LC-MS/MS method for the determination of ailanthone in rat plasma with application to pharmacokinetic study. *Journal of pharmaceutical and biomedical analysis* 102, 514-518 (2015).
38. Sharma N L, et al. The androgen receptor induces a distinct transcriptional program in castration-resistant prostate cancer in man. *Cancer cell* 23, 35-47 (2013).
39. Yuan X, Cai C, Chen S, Chen S, Yu Z, Balk S P. Androgen receptor functions in castration-resistant prostate cancer and mechanisms of resistance to new agents targeting the androgen axis. *Oncogene* 33, 2815-2825 (2014).
40. Gibbs A, Schwartzman J, Deng V, Alumkal J. Sulforaphane destabilizes the androgen receptor in prostate cancer cells by inactivating histone deacetylase 6. *Proceedings of the National Academy of Sciences of the United States of America* 106, 16663-16668 (2009).
41. Solit D B, et al. 17-Allylamino-17-demethoxygeldanamycin induces the degradation of androgen receptor and HER-2/neu and inhibits the growth of prostate cancer xenografts. *Clinical cancer research: an official journal of the American Association for Cancer Research* 8, 986-993 (2002).
42. De Leon J T, et al. Targeting the regulation of androgen receptor signaling by the heat shock protein 90 cochaperone FKBP52 in prostate cancer cells. *Proceedings of the National Academy of Sciences of the United States of America* 108, 11878-11883 (2011).
43. Hieronymus H, et al. Gene expression signature-based chemical genomic prediction identifies a novel class of HSP90 pathway modulators. *Cancer cell* 10, 321-330 (2006).
44. Shafi A A, Cox M B, Weigel N L. Androgen receptor splice variants are resistant to inhibitors of Hsp90 and FKBP52, which alter androgen receptor activity and expression. *Steroids* 78, 548-554 (2013).
45. Gillis J L, et al. Constitutively-active androgen receptor variants function independently of the HSP90 chaperone but do not confer resistance to HSP90 inhibitors. *Oncotarget* 4, 691-704 (2013).
46. Kato T, Suzumura Y, Fukushima M, Honda T, Nakanishi T, Noguchi T. Antitumor activity of novel ailanthone derivatives in vitro and in vivo. *Anticancer research* 8, 573-579 (1988).
47. Shao L, et al. Celastrol suppresses tumor cell growth through targeting an AR-ERG-NF-kappaB pathway in TMPRSS2/ERG fusion gene expressing prostate cancer. *PloS one* 8, e58391 (2013).
48. Chiang K C, et al. Celastrol blocks interleukin-6 gene expression via downregulation of NF-kappaB in prostate carcinoma cells. *PloS one* 9, e93151 (2014).
49. Chadli A, et al. Celastrol inhibits Hsp90 chaperoning of steroid receptors by inducing fibrillization of the Co-chaperone p23. *The Journal of biological chemistry* 285, 4224-4231 (2010).
50. Fu J, et al. Deleted in breast cancer 1, a novel androgen receptor (AR) coactivator that promotes AR DNA-binding activity. *The Journal of biological chemistry* 284, 6832-6840 (2009).
51. Vichai V, Kirtikara K. Sulforhodamine B colorimetric assay for cytotoxicity screening. *Nature protocols* 1, 1112-1116 (2006).
52. Tsai C H, et al. Herbal extract of *Wedelia chinensis* attenuates androgen receptor activity and orthotopic growth of prostate cancer in nude mice. *Clinical cancer research: an official journal of the American Association for Cancer Research* 15, 5435-5444 (2009).
53. Ernst J T, et al. Identification of novel HSP90alpha/beta isoform selective inhibitors using structure-based drug design. demonstration of potential utility in treating CNS disorders such as Huntington's disease. *Journal of medicinal chemistry* 57, 3382-3400 (2014).
54. Patwardhan C A, Fauq A, Peterson L B, Miller C, Blagg B S, Chadli A. Gedunin inactivates the co-chaperone p23 protein causing cancer cell death by apoptosis. *The Journal of biological chemistry* 288, 7313-7325 (2013).
55. Martinez-Yamout M A, Venkitakrishnan R P, Preece N E, Kroon G, Wright P E, Dyson H J. Localization of sites of interaction between p23 and Hsp90 in solution. *The Journal of biological chemistry* 281, 14457-14464 (2006).
56. Sun M, Tang Y, Ding T, Liu M, Wang X. Inhibitory effects of celastrol on rat liver cytochrome P450 1A2, 2C11, 2D6, 2E1 and 3A2 activity. *Fitoterapia* 92, 1-8 (2014).

What is claimed is:

1. A method for inhibiting androgen receptor signaling pathway comprising administering to a subject in need thereof a therapeutically effective amount of a pharmaceutical composition comprising a compound of Formula V

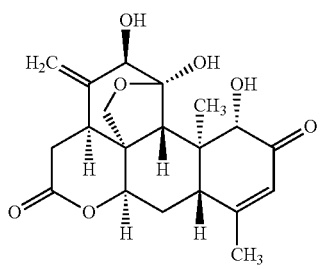

or a pharmaceutically acceptable salt, solvate, hydrate, polymorph or co-crystal, to thereby disrupt the interaction of the androgen receptor with its chaperones, and a pharmaceutically acceptable excipient,
  wherein the activity of both full-length androgen receptor (AR-FL) and constitutively active, truncated AR splice variants (AR-Vs) are inhibited, or the androgen receptor (AR) protein level is down-regulated, or the AR protein degradation is induced.

2. The method of claim 1, wherein said subject is a mammal suffering from or is at increased risk of developing prostate cancer.

3. The method of claim 2, wherein said compound inhibits the activity of androgen receptor, thereby inhibiting the proliferation, metastasis, growth, or cloning formation of prostate cancer cell, or promoting apoptosis of prostate cancer cell, or inducing the cycle arrest of prostate cancer cell.

4. The method of claim 2, wherein the prostate cancer is associated with abnormal amplification or mutation of androgen receptor, or is an androgen-dependent prostate cancer, or a castration-resistant prostate cancer, or a prostate cancer resistant to MDV3100 or bicalutamide (BIC).

5. The method of claim 1, wherein the compound of Formula (V) induces androgen receptor ubiquitination by blocking the binding between an androgen receptor and a heat shock chaperones HSP90 complex, decreasing androgen receptor stability, resulting in degradation of the androgen receptor by proteasome and inhibition of the activity of androgen receptor.

6. The method of claim 5, wherein the androgen receptor is dihydrotestosterone DHT induced androgen receptor or androgen receptor AR1-651 lacking a ligand domain.

7. A method for inhibiting the proliferation, metastasis, growth, clone formation of prostate cancer cells, or promoting apoptosis of prostate cancer cells, inducing the cycle arrest of prostate cancer cells in a subject in need thereof, comprising administering to a subject in need thereof a pharmaceutical composition comprising an effective amount of ailanthone, or a pharmaceutically acceptable salt, solvate, hydrate, polymorph, or co-crystal thereof, to disrupt the interaction of androgen receptors with their chaperones, and a pharmaceutically acceptable excipient.

8. The method of claim 7, wherein the prostate cancer cells comprises abnormal amplification or mutation of androgen receptor, or are androgen-dependent, or a castration-resistant, or resistant to MDV3100 or bicalutamide (BIC).

9. A method for treating prostate cancer comprising administering to a patient an effective amount of a pharmaceutical composition comprising ailanthone, or a pharmaceutically acceptable salt, solvate, hydrate, polymorph or co-crystal thereof, to disrupt the interaction of androgen receptors with their chaperones, and a pharmaceutically acceptable excipient.

10. The method of claim 9, wherein the prostate cancer is androgen-dependent, or a castration-resistant, or resistant to MDV3100 or bicalutamide (BIC).

* * * * *

SEQUENCE LISTING

<160> NUMBER OF SEQ ID NOS: 27

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ggtgagcaga gtgccctatc                                               20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
gaagaccttg cagcttccac                                               20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
cttgtagcct ctcgtggcag                                               20

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
gaccttcata gcatccgtga g                                             21

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
ctggtggctg atagggata                                                20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
ggacaagggg ttagggagag                                               20

<210> SEQ ID NO 7
<211> LENGTH: 21
<212> TYPE: DNA
<213> ORGANISM: Artificial Sequence

```
<220> FEATURE:
<223> OTHER INFORMATION: Primer

<400> SEQUENCE: 7
cgagacttta catggctctg t                                               21

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
tccatggagg ggtacatgta                                                 20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
agaaccaaac ggaaaggaga                                                 20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gccacatctc tgcagtcaaa                                                 20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gcagtgagga cagcctgatg                                                 20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
cggagacatc acaggcagag                                                 20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
acccagaaga ctgtggatgg                                                 20
```

```
<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
ttcagctcag ggatgacctt                                                     20

<210> SEQ ID NO 15
<211> LENGTH: 19
<212> TYPE: DNA
<213> ORGANISM: Artificial Sequence
<220> FEATURE:
<223> OTHER INFORMATION: Primer

<400> SEQUENCE: 15
gtacgccaac acagtgctg                                                      19

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
cgtcatactc ctgcttgctg                                                     20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
aaaagagccg ctgaagggaa                                                     20

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
ccaacccgga atttttctcc c                                                   21

<210> SEQ ID NO 19
<211> LENGTH: 21
<212> TYPE: RNA
<213> ORGANISM: Artificial Sequence
<220> FEATURE:
<223> OTHER INFORMATION: si-RNA

<400> SEQUENCE: 19
gaaaugauug cacuauugau u                                                   21

<210> SEQ ID NO 20
<211> LENGTH: 21
<212> TYPE: RNA
<213> ORGANISM: Artificial Sequence
<220> FEATURE:
<223> OTHER INFORMATION: si-RNA
```

```
<400> SEQUENCE: 20
cgugcagccu auugcgagau u                                              21

<210> SEQ ID NO 21
<211> LENGTH: 21
<212> TYPE: RNA
<213> ORGANISM: Artificial Sequence
<220> FEATURE:
<223> OTHER INFORMATION: si-RNA

<400> SEQUENCE: 21
gaggguguuu ggagucucau u                                              21

<210> SEQ ID NO 22
<211> LENGTH: 21
<212> TYPE: RNA
<213> ORGANISM: Artificial Sequence
<220> FEATURE:
<223> OTHER INFORMATION: si-RNA

<400> SEQUENCE: 22
aagagccgcu gaaggauuuu u                                              21

<210> SEQ ID NO 23
<211> LENGTH: 21
<212> TYPE: RNA
<213> ORGANISM: Artificial Sequence
<220> FEATURE:
<223> OTHER INFORMATION: si-RNA

<400> SEQUENCE: 23
gaugacucug ggaggauuuu u                                              21

<210> SEQ ID NO 24
<211> LENGTH: 21
<212> TYPE: RNA
<213> ORGANISM: Artificial Sequence
<220> FEATURE:
<223> OTHER INFORMATION: si-RNA

<400> SEQUENCE: 24
gcaauugcaa gcaucucaau u                                              21

<210> SEQ ID NO 25
<211> LENGTH: 21
<212> TYPE: DNA
<213> ORGANISM: Artificial Sequence
<220> FEATURE:
<223> OTHER INFORMATION: si-RNA

<400> SEQUENCE: 25
agcuuaauug gcuuagugut t                                              21

<210> SEQ ID NO 26
<211> LENGTH: 21
<212> TYPE: DNA
<213> ORGANISM: Artificial Sequence
<220> FEATURE:
<223> OTHER INFORMATION: si-RNA

<400> SEQUENCE: 26
acacuaagcc aauuaagcut t                                              21

<210> SEQ ID NO 27
```

```
<211> LENGTH: 23
<212> TYPE: DNA
<213> ORGANISM: Artificial Sequence
<220> FEATURE:
<223> OTHER INFORMATION: si-RNA

<400> SEQUENCE: 27
aattctccga acgtgtcacg ttt                                              23
```